United States Patent
Blumberg, Jr.

(10) Patent No.: US 10,126,267 B2
(45) Date of Patent: Nov. 13, 2018

(54) SYSTEM, METHOD, AND APPARATUS FOR BUBBLE DETECTION IN A FLUID LINE USING A SPLIT-RING RESONATOR

(71) Applicant: DEKA Products Limited Partnership, Manchester, NH (US)

(72) Inventor: David Blumberg, Jr., Deerfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 15/629,933

(22) Filed: Jun. 22, 2017

(65) Prior Publication Data

US 2017/0284968 A1     Oct. 5, 2017

Related U.S. Application Data

(62) Division of application No. 14/341,207, filed on Jul. 25, 2014, now Pat. No. 9,719,964.

(60) Provisional application No. 61/860,398, filed on Jul. 31, 2013.

(51) Int. Cl.
  *G01N 22/00*     (2006.01)
  *G01N 29/02*     (2006.01)

(52) U.S. Cl.
  CPC .............. *G01N 29/02* (2013.01); *G01N 22/00* (2013.01)

(58) Field of Classification Search
  CPC .................................................. G01N 22/00
  See application file for complete search history.

(56) References Cited

U.S. PATENT DOCUMENTS

| | | |
|---|---|---|
| 5,594,950 A | 1/1997 | D'Amico et al. |
| 5,950,200 A | 9/1999 | Sudai et al. |
| D599,307 S | 9/2009 | Blumberg, Jr. |
| D599,308 S | 9/2009 | Blumberg, Jr. |
| 8,314,740 B2 | 11/2012 | Blumberg, Jr. |
| 8,325,045 B2 | 12/2012 | Dattolo |
| 8,610,577 B2 | 12/2013 | Blumberg, Jr. |
| 8,784,364 B2 | 7/2014 | Kamen et al. |
| D728,779 S | 5/2015 | Sabin et al. |

(Continued)

FOREIGN PATENT DOCUMENTS

| | | |
|---|---|---|
| EP | 0511651 A2 | 11/1992 |
| WO | WO2013095459 A9 | 6/2013 |

(Continued)

OTHER PUBLICATIONS

International Search Report & Written Opinion, dated Oct. 24, 2014, received in International patent application No. PCT/US2014/048227 10 pgs.

(Continued)

*Primary Examiner* — Manish S Shah
*Assistant Examiner* — Alex Devito
(74) *Attorney, Agent, or Firm* — James D. Wyninegar, Jr.

(57) ABSTRACT

A system, method, and apparatus for detecting at least one condition of interest relating to a tube, e.g. the presence of an air bubble. In some embodiments, the sensor includes antennas, a split-ring resonator, a frequency generator capable of generating frequencies in the microwave range, and a detection component. The detection component may estimate at least one parameter of received microwave energy in order to determine if a condition of interest exists.

15 Claims, 54 Drawing Sheets

(56) References Cited

U.S. PATENT DOCUMENTS

| | | | |
|---|---|---|---|
| D735,319 S | 7/2015 | Sabin et al. |
| D736,370 S | 8/2015 | Sabin et al. |
| 9,151,646 B2 | 10/2015 | Kamen et al. |
| D745,661 S | 12/2015 | Collins et al. |
| D749,206 S | 2/2016 | Johnson et al. |
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| D756,386 S | 5/2016 | Kendler et al. |
| D758,399 S | 6/2016 | Kendler et al. |
| D760,288 S | 6/2016 | Kendler et al. |
| D760,289 S | 6/2016 | Kendler et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| D767,756 S | 9/2016 | Sabin |
| 9,435,455 B2 | 9/2016 | Peret et al. |
| D768,716 S | 10/2016 | Kendler et al. |
| 9,465,919 B2 | 10/2016 | Kamen et al. |
| 9,488,200 B2 | 11/2016 | Kamen et al. |
| D789,516 S | 6/2017 | Gill et al. |
| 9,675,756 B2 | 6/2017 | Kamen et al. |
| 9,677,555 B2 | 6/2017 | Kamen et al. |
| 2009/0069925 A1 | 3/2009 | Dattolo et al. |
| 2009/0289796 A1 | 11/2009 | Blumberg, Jr. et al. |
| 2009/0295659 A1 | 12/2009 | Blumberg, Jr. et al. |
| 2010/0185142 A1 | 7/2010 | Kamen et al. |
| 2010/0185175 A1 | 7/2010 | Kamen et al. |
| 2010/0191186 A1 | 7/2010 | Blumberg, Jr. et al. |
| 2011/0144574 A1 | 6/2011 | Kamen et al. |
| 2011/0205134 A1 | 8/2011 | Blumberg, Jr. et al. |
| 2011/0257765 A1 | 10/2011 | Evans et al. |
| 2011/0313789 A1 | 12/2011 | Kamen et al. |
| 2011/0319813 A1 | 12/2011 | Kamen et al. |
| 2012/0101440 A1 | 4/2012 | Kamen et al. |
| 2012/0185267 A1 | 7/2012 | Kamen |
| 2012/0236895 A1* | 9/2012 | Miles ........................ H01P 7/08 372/55 |
| 2012/0238851 A1 | 9/2012 | Kamen et al. |
| 2013/0177455 A1 | 7/2013 | Kamen |
| 2013/0182381 A1 | 7/2013 | Gray |
| 2013/0184676 A1 | 7/2013 | Kamen |
| 2013/0188040 A1 | 7/2013 | Kamen |
| 2013/0191513 A1 | 7/2013 | Kamen |
| 2013/0197693 A1 | 8/2013 | Kamen |
| 2013/0204188 A1 | 8/2013 | Kamen |
| 2013/0272773 A1 | 10/2013 | Kamen |
| 2013/0281965 A1 | 10/2013 | Kamen |
| 2013/0297330 A1 | 11/2013 | Kamen et al. |
| 2013/0310990 A1 | 11/2013 | Peret et al. |
| 2013/0317753 A1 | 11/2013 | Kamen |
| 2013/0317837 A1 | 11/2013 | Ballantyne |
| 2013/0328740 A1 | 12/2013 | Blumberg, Jr. |
| 2013/0334317 A1 | 12/2013 | Dattolo |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0104131 A1 | 4/2014 | Blumberg, Jr. |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0227021 A1 | 8/2014 | Kamen |
| 2014/0318639 A1 | 10/2014 | Peret |
| 2014/0343492 A1 | 11/2014 | Kamen |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0033823 A1 | 2/2015 | Blumberg, Jr. |
| 2015/0045767 A1 | 2/2015 | Kamen et al. |
| 2015/0314083 A1 | 4/2015 | Blumberg, Jr. et al. |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0303563 A1 | 10/2015 | Blumberg, Jr. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo et al. |
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0262977 A1 | 9/2016 | Demers et al. |
| 2016/0319850 A1 | 11/2016 | Kamen et al. |

FOREIGN PATENT DOCUMENTS

| | | |
|---|---|---|
| WO | WO2013096713 A2 | 6/2013 |
| WO | WO2013096718 A2 | 6/2013 |
| WO | WO2013096722 A2 | 6/2013 |
| WO | WO2013096909 A2 | 6/2013 |
| WO | WO2013176770 A2 | 11/2013 |
| WO | WO2013177357 A1 | 11/2013 |
| WO | WO2014100557 A2 | 6/2014 |
| WO | WO2014100571 A2 | 6/2014 |
| WO | WO2014100658 A1 | 6/2014 |
| WO | WO2014100687 A2 | 6/2014 |
| WO | WO2014100736 A2 | 6/2014 |
| WO | WO2014100744 A2 | 6/2014 |
| WO | WO2014144557 A2 | 9/2014 |
| WO | WO2015017275 A1 | 2/2015 |

OTHER PUBLICATIONS

International Preliminary Report on Patentability, dated Feb. 2, 2016, received in International patent application No. PCT/US2014/048227 7 pgs.

A Masood et al: "Split Ring Resonator Technique for Compositional Analysis of Solvents in Microcapillary Systems" Oct. 16, 2008, http://www.rsc.org/binaries/loc/2008/pdfs/papers/549_0729.pdf, pp. 1636-1637.

Abidi M et al.: "Sensing Liquid Properties Using Split-Ring Resonator in Mm-wave band", IECON 2010—36th Annual Conference on IEEE Industrial Electronics Society, IEEE, Piscataway, NJ, USA, Nov. 7, 2010 pp. 1298-1301 ISBN: 978-1-4244-5225-5.

U.S. Appl. No. 61/860,398, filed Jul. 31, 2013.

PCT/US2014/48227, Jul. 25, 2014, WO2015017275A1.

U.S. Appl. No. 14/341,207, filed Jul. 25, 2014, US20150033823A1.

U.S. Appl. No. 14/341,207, filed Jul. 25, 2014.

* cited by examiner

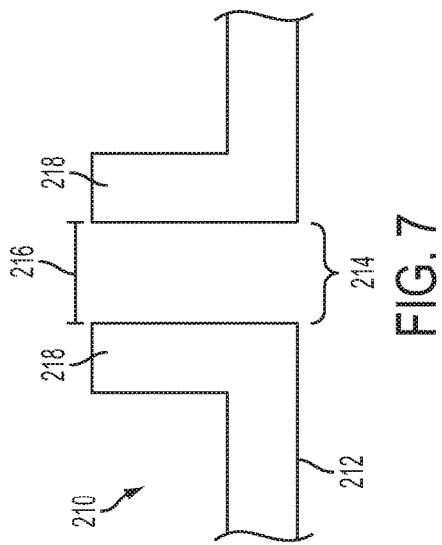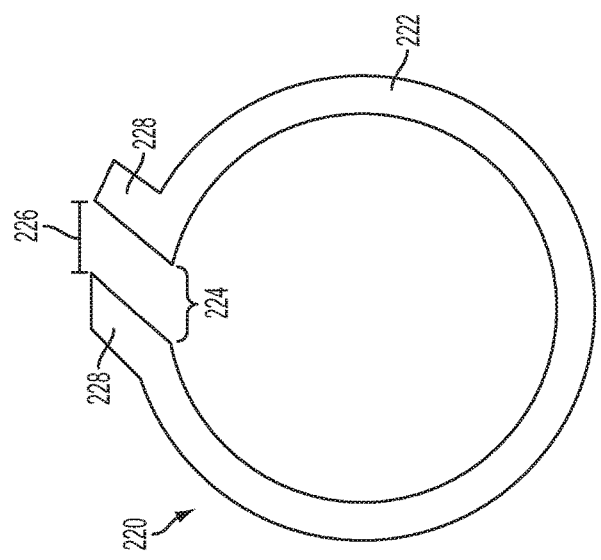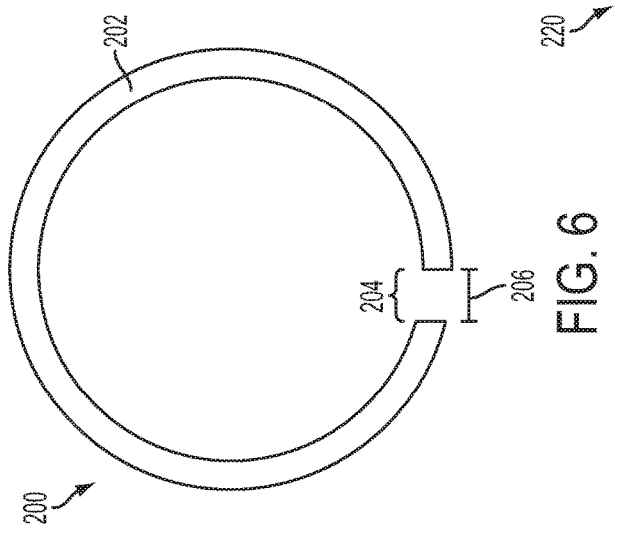

SYSTEM, METHOD, AND APPARATUS FOR BUBBLE DETECTION IN A FLUID LINE USING A SPLIT-RING RESONATOR

CROSS REFERENCE TO RELATED APPLICATIONS

This application is a divisional application of U.S. patent application Ser. No. 14/341,207, entitled: System, Method, and Apparatus for Bubble Detection in a Fluid Line Using a Split-Ring Resonator, filed on Jul. 25, 2014, now U.S. Publication No. US-2015-0033823-A1, published on Feb. 5, 2015, which claims the benefit of U.S. Provisional Application Ser. No. 61/860,398 filed Jul. 31, 2013 and entitled System, Method, and Apparatus for Bubble Detection in a Fluid Line Using a Split-Ring Resonator, which is hereby incorporated herein by reference in its entirety.

BACKGROUND

Relevant Field

The present disclosure relates to detecting the presence or absence of materials with differing dielectric properties or a material change. More particularly, the present disclosure relates to a system, method and apparatus for said detection. Some embodiments relate to detection of air bubbles in a fluid line using a split-ring resonator, e.g., air bubble detection in an intravenous fluid line using a split-ring resonator. Some embodiments relate to the detection of the coagulation time of blood samples using a split-ring resonator.

Description of Related Art

Providing patient care in a hospital generally necessitates the interaction of numerous professionals and caregivers (e.g., doctors, nurses, pharmacists, technicians, nurse practitioners, etc.) and any number of medical devices/systems needed for treatment of a given patient. Despite the existence of systems intended to facilitate the care process, such as those incorporating electronic medical records ("EMR") and computerized provider order entry ("CPOE"), the process of providing comprehensive care to patients including ordering and delivering medical treatments, such as medications, is associated with a number of non-trivial issues. One such medical treatment involves the insertion of fluid into a patient. The insertion of fluid into the patient may be accomplished by using a bag of fluid that is positioned above a patient and an intravenous fluid from the bag to a needle that is inserted into the patient. The tubing between the bag and the patient may include various devices, such as an infusion pump to control to flow of fluid between the bag and the patient. Another device may be an air detector.

Detection of air bubbles during the insertion of fluid into a patient maybe desirable for a number of reasons. Depending on the volume of air and the insertion site, insertion of air into a patient can cause a fatal air embolism. Additionally, a volume of air which is inserted into a patient is inserted in place of an equal volume of the fluid. This may also cause serious concern with some medicaments. For this reason, it is desirable to monitor a fluid line for the presence of air.

Known solutions monitor for air in a fluid line often utilize ultrasonic sensors or sensors monitoring the electric impedance of the fluid line. While such sensors may detect the presence of an air bubble in a fluid, these sensors tend to be expensive. For some applications, such sensors are prohibitively expensive. Additionally, the resolution of these sensors is generally less than ideal. A need therefore exists for a sensor which may accurately and consistently detect the presence of an air bubble in a fluid line at lower cost. Additionally, a need exists for a sensor with resolution high enough to detect the presence of smaller volumes of air. An air bubble sensor using at least one split ring resonator satiates this need by providing a higher resolution sensor at a price approximately ten times lower than conventional sensor technologies.

SUMMARY

In accordance with one embodiment of the present disclosure a system for detecting an at least one condition of interest relating to a tube may comprise a split-ring resonator component configured to interface with the tube. The system may comprise a detection component operatively coupled to the split-ring resonator component. The detection component may be configured to detect the at least one condition of interest.

In some embodiments, a system for detecting at least one condition of interest relating to a tube may comprise a split-ring resonator component including a split-ring resonator. In some embodiments, the detection component may detect at least one condition of interest by estimating at least one parameter corresponding to the split-ring resonator. In some embodiments, the at least one parameter may be selected from the group consisting of a group delay caused by an inner volume of the tube, a propagation delay caused by the inner volume of the tube, a group delay caused by the split-ring resonator, a phase shift caused by the split-ring resonator, a resonance frequency of the split-ring resonator, a phase angle of a test signal applied the split-ring resonator, an amplitude of the test signal applied to the split-ring resonator, a frequency response of the split-ring resonator, a frequency response within a predetermined frequency range of the split-ring resonator, a Q of the split-ring resonator, a bandwidth of a split-ring resonator, a peak of a bandwidth response of the split-ring resonator, an anti-resonance of the split-ring resonator, a phase response of the split-ring resonator, an impedance of the split-ring resonator, a propagation delay of split-ring resonant, an S11 parameter of the split-ring resonator, an S12 parameter of the split-ring resonator, an S21 parameter of the split-ring resonator, and an S22 parameter of the split-ring resonator. In some embodiments, the detection component may apply a test signal to the split-ring resonator to estimate the at least one parameter. The split-ring resonator may include at least one gap disposed adjacent to the tube and at least one parameter may correspond to an impedance of the at least one gap. In some embodiments, the split-ring resonator may include at least one gap, and at least one parameter may correspond to dielectric loading of the at least one gap. In some embodiments, the detection component may detect at least one condition of interest by detecting a change in the at least one parameter.

In some embodiments, the split-ring resonator component may include a split-ring resonator comprising a conductor ring with a gap defined therein. The conductor ring may be disposed on a dielectric backing. In some embodiments, the split-ring resonator component may include a split ring resonator comprising at least one conductor defining at least one gap. The at least one conductor may include one or more capacitive extensions.

In some embodiments, the split-ring resonator component may include a split-ring resonator comprising a first conductor defining a first gap. The split-ring resonator may include a second conductor disposed adjacent to an inner periphery of the first conductor. The second conductor may define a second gap. The first conductor and said second conductor may be concentric and define a common center point. In some embodiments, The center of the first gap is at a radial angle from the common center that is about 180 degrees from the center of the second gap.

In some embodiments, at least one of the at least one condition of interest is selected from a group consisting of: the tube is full, the tube is empty, an air bubble exists in the tube, an air bubble of an estimated volume exists in the tube, the tube is not present, the tube is improperly inserted, the tube is properly inserted, the tube is primed, and the tube is unprimed.

In some embodiments, the split-ring resonator component may comprise a transmitting antenna configured to transmit microwave energy. The split-ring resonator component may include a receiving antenna configured to receive the microwave energy. The split-ring resonator component may include a split-ring resonator positioned between the transmitting and receiving antennas and positioned adjacent to the tube. The split-ring resonator may be adapted to vary at least one parameter of the microwave energy in response to the existence of the at least one condition of interest.

In some embodiments, the transmitting antenna, the receiving antenna, and the split-ring resonator may be adapted to encourage a tunneling effect between the transmitting and receiving antennas when the microwave energy is transmitted from the transmitting antenna to the receiving antenna. In some embodiments, at least one of the transmitting antenna and the receiving antenna is a loop antenna.

In accordance with another embodiment of the present disclose an apparatus may comprise a raceway configured to receive a tube. The apparatus may also include a shield configured to at least partially shield the raceway. The apparatus may include at least one split-ring resonator disposed within the shield and adjacent to the raceway. The apparatus may include a first antenna disposed within the shield and a second antenna disposed within the shield.

In some embodiments, the apparatus may further comprise a microwave generating circuit coupled to the first antenna. The microwave generating circuit may be configured to generate microwave energy for transmission from the first antenna. A receiver circuit coupled to the second antenna may also be included. The microwave receiver circuit may be configured to receive the microwave energy. In some embodiments, a bubble detecting circuit operatively coupled to the microwave generating circuit and the receiver circuit may be included to compare the microwave energy from the microwave generating circuit to the microwave energy received from the receiver circuit to detect a bubble within the tube.

In some embodiments, the apparatus may further comprise a circuit board disposed on an outer surface of the shield. The circuit board may comprise the microwave generating circuit, the receiver circuit, and the bubble detecting circuit. In some embodiments, the bubble detecting circuit may detect the bubble by using the microwave energy to determine at least one of a group delay caused by an inner volume of the tube, a propagation delay caused by the inner volume of the tube, a group delay caused by the split-ring resonator, a phase shift caused by the split-ring resonator, a resonance frequency of the split-ring resonator, a phase angle of a test signal applied the split-ring resonator, an amplitude of the test signal applied to the split-ring resonator, a frequency response of the split-ring resonator, a frequency response within a predetermined frequency range of the split-ring resonator, a Q of the split-ring resonator, a bandwidth of a split-ring resonator, a peak of a bandwidth response of the split-ring resonator, an anti-resonance of the split-ring resonator, a phase response of the split-ring resonator, an impedance of the split-ring resonator, a propagation delay of split-ring resonant, an S11 parameter of the split-ring resonator, an S12 parameter of the split-ring resonator, an S21 parameter of the split-ring resonator, and an S22 parameter of the split-ring resonator.

In accordance with another embodiment of the present disclosure, a method for detecting a bubble may comprise generating microwave energy. The method may comprise transmitting the microwave energy from an antenna. The method may comprise applying the transmitted microwave energy to a split-ring resonator said split ring resonator adjacent a tube. The method may comprise receiving the microwave energy from the antenna and the split-ring resonator. The method may comprise detecting a bubble adjacent to the split-ring resonator using the received microwave energy.

In accordance with an embodiment of the present disclosure a system may comprise a split-ring resonator component configured to interface with a raceway. The system may also comprise a detection component operatively coupled to the split-ring resonant component. The detection component may be configured to detect a state of the raceway. The detection component may be configured to detect a state of the raceway including at least one of an absence of a tube within the raceway, a presence of the tube within the raceway, a presence of the tube within the raceway having liquid wholly disposed therein, a presence of the tube within the raceway having liquid and a bubble disposed therein, and a presence of the tube within the raceway have no liquid disposed therein.

In some embodiments, the split-ring resonator component includes a split-ring resonator. The split-ring resonator may include at least one capacitive extension. In some embodiments, the detection component may detect the state of the raceway by estimating at least one parameter corresponding to the split-ring resonator. The at least one parameter may be selected from the group consisting of a group delay caused by an inner volume of the tube, a propagation delay caused by the inner volume of the tube, a group delay caused by the split-ring resonator, a phase shift caused by the split-ring resonator, a resonance frequency of the split-ring resonator, a phase angle of a test signal applied the split-ring resonator, an amplitude of the test signal applied to the split-ring resonator, a frequency response of the split-ring resonator, a frequency response within a predetermined frequency range of the split-ring resonator, a Q of the split-ring resonator, a bandwidth of a split-ring resonator, a peak of a bandwidth response of the split-ring resonator, an anti-resonance of the split-ring resonator, a phase response of the split-ring resonator, an impedance of the split-ring resonator, a propagation delay of split-ring resonant, an S11 parameter of the split-ring resonator, an S12 parameter of the split-ring resonator, an S21 parameter of the split-ring resonator, and an S22 parameter of the split-ring resonator.

In some embodiments, the detection component may apply a test signal to the split-ring resonator to estimate the at least one parameter. In some embodiments, the split-ring resonator may include at least one gap disposed adjacent to the tube. The at least one parameter corresponds to an impedance of the at least one gap. The split-ring resonator may include at least one gap. The at least one parameter may correspond to dielectric loading of the at least one gap. The detection component may detect the state of the raceway by detecting a change in the least one parameter.

In some embodiments, the split-ring resonator component may include a split-ring resonator comprising a conductor ring defining a gap. The conductor ring may be disposed on a dielectric backing.

In some embodiments, the split-ring resonator component may include a split-ring resonator comprising a first conductor defining a first gap. The split-ring resonator may comprise a second conductor disposed adjacent to an inner periphery of the first conductor. The second conductor may define a second gap. The first conductor and second conductor may be concentric and define a common center point. In some embodiments the center of the first gap may be at a radial angle from the common center that is about 180 degrees from the center of the second gap from the common center. In some embodiments at least one of the first conductor and second conductor may include at least one capacitive extension.

In some embodiments, the split-ring resonator component may comprise a transmitting antenna configured to transmit microwave energy. In some embodiments, the split-ring resonator component may comprise a receiving antenna configured to receive the microwave energy. In some embodiments, a split-ring resonator may be positioned between the transmitting and receiving antennas and positioned adjacent to the tube. The split-ring resonator may be adapted to vary at least one parameter of the microwave energy depending on the state of the raceway.

In some embodiments, the transmitting antenna, the receiving antenna, and the split-ring resonator may be adapted to encourage tunneling between the transmitting and receiving antennas when the microwave energy is transmitted from the transmitting antenna to the receiving antenna. In some embodiments at least one of the transmitting antenna and the receiving antenna may be a loop antenna.

In accordance with an embodiment of the present disclosure a system for detecting an at least one condition of interest relating to at least one material of interest may comprise a split-ring resonator component configured to interface with the at least one material of interest. The system may also comprise a detection component operatively coupled to the split-ring resonator component. The detection component may be configured to detect the at least one condition of interest. The split-ring resonator component may include a split-ring resonator. The detection component may detect the at least one condition of interest by estimating at least one parameter corresponding to the split-ring resonator. The at least one parameter is selected from the group consisting of a group delay caused by an inner volume of a tube, a propagation delay caused by the inner volume of a tube, a group delay caused by the split-ring resonator, a phase shift caused by the split-ring resonator, a resonance frequency of the split-ring resonator, a phase angle of a test signal applied the split-ring resonator, an amplitude of the test signal applied to the split-ring resonator, a frequency response of the split-ring resonator, a frequency response within a predetermined frequency range of the split-ring resonator, a Q of the split-ring resonator, a bandwidth of a split-ring resonator, a peak of a bandwidth response of the split-ring resonator, an anti-resonance of the split-ring resonator, a phase response of the split-ring resonator, an impedance of the split-ring resonator, a propagation delay of split-ring resonant, an S11 parameter of the split-ring resonator, an S12 parameter of the split-ring resonator, an S21 parameter of the split-ring resonator, and an S22 parameter of the split-ring resonator.

In some embodiments the detection component may apply a test signal to the split-ring resonator to estimate the at least one parameter. The split-ring resonator may include at least one gap disposed adjacent to the at least one material of interest, wherein the at least one parameter corresponds to an impedance of the at least one gap. The split-ring resonator may include at least one gap. The at least one parameter may correspond to dielectric loading of the at least one gap. In some embodiments, the detection component may detect the at least one condition of interest by detecting a change in the at least one parameter.

In some embodiments, the split-ring resonator component may include a split-ring resonator comprising a conductor ring with a gap defined therein. The conductor ring may be disposed on a dielectric backing. In some embodiments, the split-ring resonator component may include a split ring resonator comprising at least one conductor defining at least one gap. The at least one conductor may include one or more capacitive extensions.

The split-ring resonator component may include a split-ring resonator comprising a first conductor defining a first gap. The split-ring resonator may comprise a second conductor disposed adjacent to an inner periphery of the first conductor. The second conductor may define a second gap. The first conductor and said second conductor may be concentric and define a common center point. In some embodiments, the center of the first gap may be at a radial angle from the common center that may be about 180 degrees from the center of the second gap.

In some embodiments, the split-ring resonator component may comprise a transmitting antenna configured to transmit microwave energy. The split-ring resonator component may comprise a receiving antenna configured to receive the microwave energy. The split-ring resonator component may comprise a split-ring resonator positioned between the transmitting and receiving antennas and positioned adjacent to the at least one material of interest. The split-ring resonator may be adapted to vary at least one parameter of the microwave energy in response to the existence of the at least one condition of interest.

In some embodiments, the transmitting antenna, the receiving antenna, and the split-ring resonator may be adapted to encourage a tunneling effect between the transmitting and receiving antennas when the microwave energy is transmitted from the transmitting antenna to the receiving antenna. The at least one of the transmitting antenna and the receiving antenna is a loop antenna.

In some embodiments, the at least one condition of interest may relate to the coagulation time of a blood sample.

BRIEF DESCRIPTION OF THE DRAWINGS

These and other aspects will become more apparent from the following detailed description of the various embodiments of the present disclosure with reference to the drawings wherein:

FIG. 6 shows an example split ring resonator in accordance with an embodiment of the present disclosure;

FIG. 7 shows a capacitor formed in a split of a split ring resonator in accordance with an embodiment of the present disclosure;

FIGS. 8-14 show a number of example split ring resonators in accordance with an embodiment of the present disclosure;

FIG. 34 shows an alternate specific detailed example of the part of the system shown in FIG. 35 in accordance with an embodiment of the present disclosure;

FIG. 35 depicts an example rectifier circuit for use in a system for detecting a bubble in accordance with an embodiment of the present disclosure;

DETAILED DESCRIPTION

Figure 1:
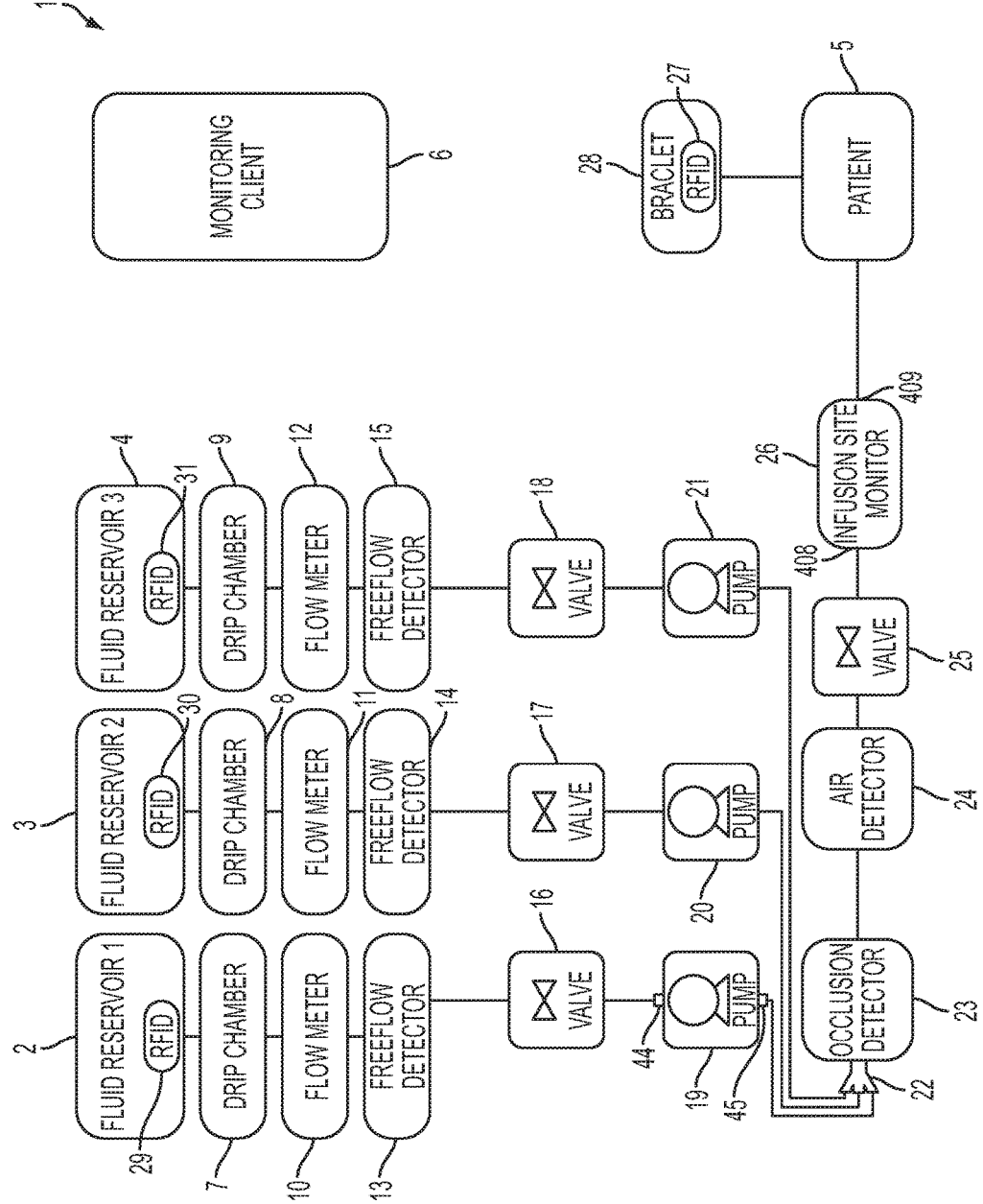
FIG. 1 shows block diagram of a system for infusing liquid in accordance with an embodiment of the present disclosure.

FIG. 1 shows a block diagram of a system 1 for infusing fluid. System 1 in FIG. 1 includes fluid reservoirs 2, 3, and 4 for infusing the fluid contained therein into a patient 5. The fluid reservoirs 2, 3, and 4 may be gravity fed into drip chambers 7, 8, and 9, respectively. The drip chambers 7, 8, and 9 are respectively fed into flow meters 10, 11, and 12. From the flow meters 10, 11, and 12, the fluid is fed into free-flow detectors 13, 14, and 15, respectively.

The system 1 in FIG. 1 also includes valves 16, 17, and 18. Each of the valves 16, 17, and 18 are coupled respectively to free-flow detectors 13, 14, and 15. Pumps 19, 20, and 21 receive fluid from the valves 16, 17, and 18, and combine the fluid using a connector 22. Fluid from the connector 22 is fed into an occlusion detector 23. Fluid may then be fed into an air detector 24. The occlusion detector 23 can detect when an occlusion exists within tubing of the system 1. The air detector 24 detects if air is present in the tubing, e.g., when flowing towards the patient 5. Prior to entering into an infusion site monitor 26, the fluid passes through a valve 25.

The monitoring client 6, in some embodiments, monitors operation of the system 1. For example, when the monitoring client 6 receives notice an occlusion is detected by the occlusion detector 23 and/or a predetermined threshold of air is detected by the air detector 24 (e.g., a bubble), the monitoring client 6 may wirelessly communicate a signal to the valve 25 to shut-off fluid flow to the patient 5.

The monitoring client 6 may also remotely send a prescription to a pharmacy. The prescription may be a prescription for infusing a fluid using a fluid pump. The pharmacy may include one or more computers connected to a network, e.g., the internet, to receive the prescription and queue the prescription within the one or more computers. The pharmacy may use the prescription to compound the drug (e.g., using an automated compounding device coupled to the one or more computers or manually by a pharmacists viewing the queue of the one or more computers), pre-fill a fluid reservoir associated with an infusion pump, and/or program the infusion pump (e.g., a treatment regime is programmed into the infusion pump 19) at the pharmacy in accordance with the prescription. The fluid reservoir 2 may be automatically filled by the automated compounding device and/or the infusion pump 19 may be automatically programmed by the automated compounding device. The automated compounding device may generate a barcode, RFID tag 29 and/or data. The information within the barcode, RFID tag 29, and/or data may include the treatment regime, prescription, and/or patient information. The automated compounding device may: attach the barcode to the fluid reservoir 2 and/or the infusion pump 19; attach the RFID tag 29 to the fluid reservoir 2 and/or the infusion pump 19; and/or program the RFID tag 29, or memory within the fluid reservoir 2 or the infusion pump 19 with the information or data. The data or information may be sent to a database (e.g., electronic medical records) that associates the prescription with the fluid reservoir 2 and/or the infusion pump 19, e.g., using a serial number or other identifying information within the barcode, RFID tag 29, or memory.

The infusion pump 19 may have a scanner, e.g., an RFID interrogator that interrogates the RFID tag 29 or a barcode scanner that scans a barcode of the fluid reservoir 2, to determine that it is the correct fluid within the fluid reservoir 2, it is the correct fluid reservoir 2, the treatment programmed into the infusion pump 19 corresponds to the fluid within the fluid reservoir 2 and/or the fluid reservoir 2 and infusion pump 19 are correct for the particular patient (e.g., as determined from a patient's barcode, RFID 27, or other patient identification). For example, the infusion pump 19 may scan the RFID tag 29 of the fluid reservoir 2 and check if the serial number or fluid type encoded within the RFID tag 29 is the same as indicated by the programmed treatment within the infusion pump 19. Additionally or alternatively, the infusion pump 19 may interrogate the RFID tag 29 of the fluid reservoir 2 for a serial number and the RFID tag 27 of the patient 5 for a patient serial number, and also interrogate the electronic medical records to determine if the serial number of the fluid reservoir 19 within the RFID tag 29 matches a patient's serial number within the RFID tag 27 as indicated by the electronic medical records. Additionally or alternatively, the monitoring client 6 may scan the RFID tag 29 of the fluid reservoir 2 and an RFID tag of the infusion pump 19 to determine that it is the correct fluid within the fluid reservoir 2, it is the correct fluid reservoir 2, the treatment programmed into the infusion pump 19 corresponds to the fluid within the fluid reservoir 2, and/or the fluid reservoir 2 and infusion pump 19 are correct for the particular patient (e.g., as determined from a patient's barcode, RFID tag 27, electronic medical records, or other patient identification or information). Additionally or alternatively, the monitoring client 6 or the infusion pump 19 may interrogate an electronic medical records database and/or the pharmacy to verify the prescription or download the prescription, e.g., using a barcode serial number on the infusion pump 19 or fluid reservoir 2. Though the above discussion relates to infusion pump 19, its related components, and its interaction with the system 1, it should be noted that infusion pumps 20 and 21 may be similarly configured.

Additionally or alternatively, the flow from the pumps 19, 20, and 21 may be monitored and/or controlled by the monitoring client 6 to ensure safe drug delivery. The monitoring client 6 may scan a RFID tag 27 on a bracelet 28, and also RFID tags 29, 30, and 31 on the fluid reservoirs, 2, 3, and 4, respectively. The monitoring client 6 may download electronic medical records ("EMR") associated with the RFID tag 27 on the patient's 5 bracelet, and compare it to one or more prescriptions found in the EMR of the patient 5. If the EMR indicates that the fluid reservoirs 2, 3, and 4 contain the correct medication, a user can input into the monitoring client 6 a command to start pumping fluid through pumps 19, 20, and/or 21 into the patient 5.

Figure 2:
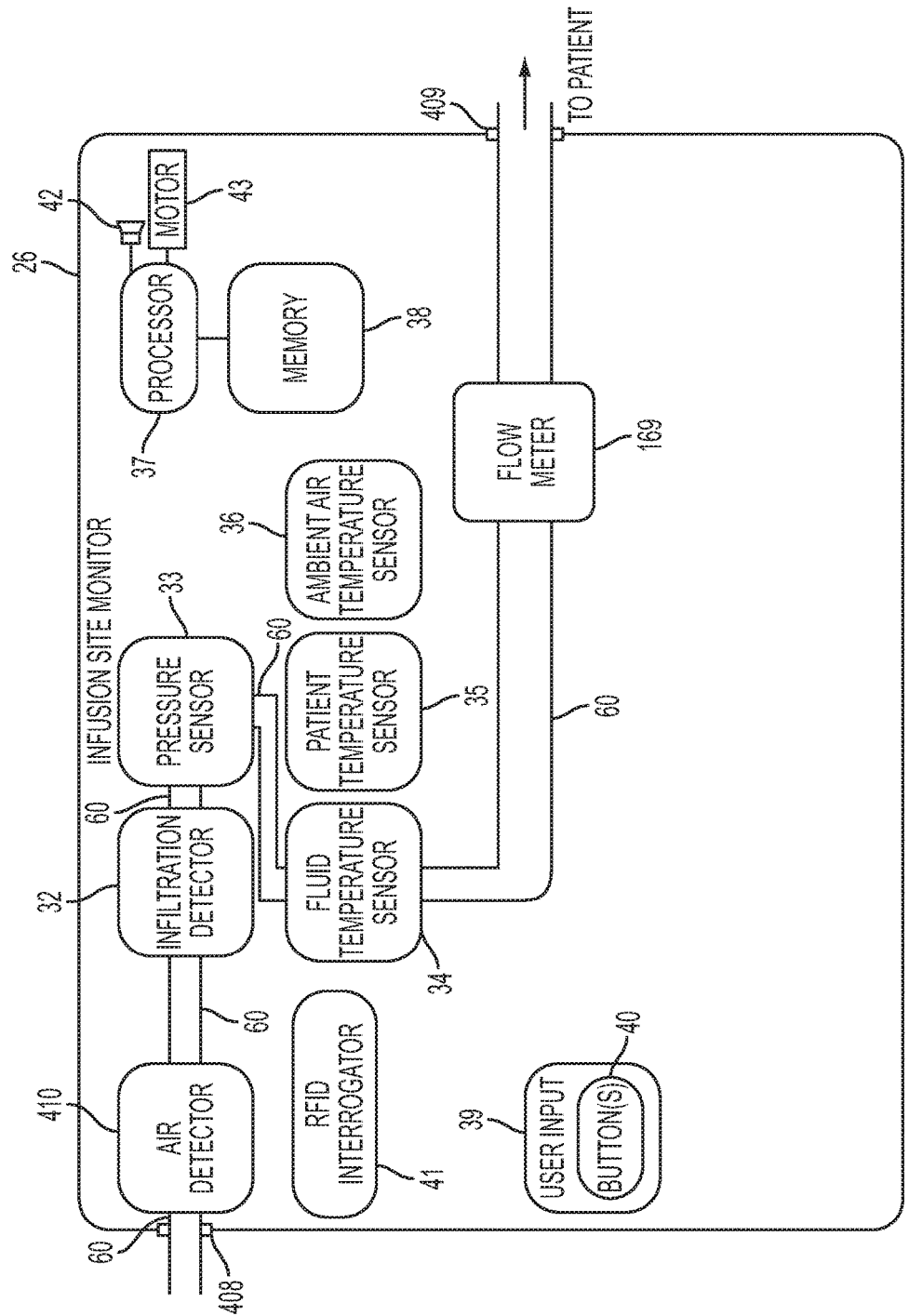
FIG. 2 shows a block diagram of an infusion site monitor of the system of FIG. 1 in accordance with an embodiment of the present disclosure.

The infusion site monitor 26 monitors the site at which the fluid is fed into the patient 5. The infusion site monitor 26 receives the fluid through an input port 408 and feeds the fluid to the patient 5 through an output port 409. As shown in FIG. 2, in some embodiments, the infusion site monitor 5 optionally includes an air detector 410, and infiltration detector 32, a pressure sensor 33, a fluid-temperature sensor 34, and/or a patient temperature sensor 35. In some embodiments, the infusion site monitor 26 optionally includes an ambient air temperature sensor 35 and an RFID interrogator 41.

The infusion site monitor 26 also includes a processor 37 and a memory 38. The memory 38 may include processor executable instructions configured for execution on the processor 37. The processor 37 is in operative communication with the air detector 410, the infiltration detector 32, the pressure sensor 33, the fluid-temperature sensor 34, the patient temperature sensor 35, the ambient air temperature sensor 36, the RFID interrogator 41, the user input 39, and the buttons 40. For example, the processor 37 may be coupled to a bus, a parallel communication link, a serial communication link, a wireless communication link, and/or the like, which is connected to the other components (e.g., the components 410, 32, 33, 34, 35, 36, 41, 39, 40). Referring to FIGS. 1 and 2, information from the various circuitry 410, 32, 33, 34, 35, 36, 39, 40, and/or 41 may be communicated to the monitoring client 6 via a wired or wireless communication link, e.g., WiFi, USB, serial, WiMax, Bluetooth, Zigbee, and the like.

In FIG. 1, In an each of pumps 19, 20, and 21, or the fluid reservoirs 2, 3, and 4 may include a upstream and/or downstream pressure generating source (e.g., an occluder, speaker, etc) to generate a pressure "signature" that would travel along the line and into the other devices, e.g., pumping, monitoring, or metering devices. These pressure signatures may indicate the pressure in each of the lines, may be used to identify each line and coordinate the flow rates of the lines, and/or indicate what the measured flow rate of the line should be.

For example, each of the pumps 19, 20, and 21 may transmit sound pressure down the IV line to the infusion site monitor 26 (which may include a transducer to detect these pressure waves) indicating to the infusion site monitor 26 the expected total flow rate therethrough. A flow rate meter 169 (see FIG. 2) may measure the liquid flow rate, and if the measured liquid flow rate deviates by a predetermined amount, the infusion site monitor 26 may issue an alarm and/or alert, e.g., the alarm may signal the valves 16, 17, 18, and 25 to close, and/or the monitoring client 6 may use the information for logging purposes and/or to cause the valves 16, 17, 18, and 25 to close.

Referring again to FIG. 2 and as previously mentioned, the processor 37 is in operative communication with user input 39 and one or more buttons 40. The infusion site monitor 26 may receive various user inputs 39 to signal the processor 37 to start monitoring treatment of the patient 5. Additionally or alternatively, the infusion site monitor 26 may interrogate the RFID 27 of the patient's 5 bracelet (see FIG. 1) to determine if the infusion site monitor 26 is coupled to the correct patient 5.

The air detector 410 is in operative communication with the processor 37. The air detector 410 can measure, estimate, and/or determine the amount of air entering into the infusion site monitor 26 via the input port 29. In some embodiments, when the processor 37 determines that air within the tube 60 exceeds a predetermined threshold, the processor 37 communicates an alarm or alert to the monitoring client 6 (see FIG. 1) which can signal valve 25 to shut off fluid flow to the patient 5. The air detector 410 may be an ultrasonic air detector, an impedance-based air detector, or one that utilizes split-ring resonators.

The infiltration detector 32 is in operative communication with the processor 37. The air detector 410 can measure, estimate, and/or determine the amount of blood entering into the infusion site monitor 26 via the output port 30. In some embodiments, when the processor 37 determines that blood within the tube 60 exceeds a predetermined threshold, the processor 37 communicates an alarm or alert to the monitoring client 6 (see FIG. 1) which can signal the valve 25 to shut off fluid flow to the patient 5. The infiltration detector 32 may be CCD based, camera based, optical based, and the like.

The pressure sensor 33 is in operative communication with the processor 37. The pressure sensor 33 can measure, estimate, and/or determine the amount of pressure entering, exiting and/or flowing through the infusion site monitor 26 via the ports 29 and 30. In some embodiments, when the processor 37 determines that pressure in the tube 60 exceeds a predetermined threshold and/or is below a predetermined threshold, the processor 37 communicates an alarm or alert to the monitoring client 6 (see FIG. 1) which can signal the valve 25 to shut off fluid flow to the patient 5. The pressure sensor 33 may be a resistive element that changes in resistance as a force is applied to the resistive element, the resistive element is stretched, and/or the resistive element is pulled. The resistive element may be wrapped around the tube 60 such that as the pressure of the fluid causes the tube 60 to expand, the resistance of the resistive element is measured and is associated with a pressure within the tube 60, e.g., the resistance may be measured and a look-up table may be used to look up an estimated pressure within the tube 60 using the resistance.

The fluid-temperature sensor 34 is in operative communication with the processor 37. The fluid-temperature sensor 34 can measure, estimate, and/or determine the temperature of the fluid within the tube 60. In some embodiments, when the processor 37 determines that temperature of the fluid within the tube 60 exceeds a predetermined threshold and/or is below a predetermined threshold, the processor 37 communicates an alarm or alert to the monitoring client 6 (see FIG. 1) which can signal valve 25 to shut off fluid flow to the patient 5. The fluid-temperature sensor 34 may utilize a temperature sensitive material, a positive temperature-coefficient material, a negative temperature-coefficient material, or other temperature sensor technology.

The patient temperature sensor 35 is in operative communication with the processor 37. The patient temperature sensor 35 can measure, estimate, and/or determine the temperature of the patient 5 (see FIG. 1). The temperature of the patient 5 may be used to determine the condition of the patient 5, compliance with a temperature affecting medication, or effect of a temperature affecting medication. The temperature of the patient 5 (a patient-condition parameter) may be communicated to the monitoring client 6 (see FIG. 1). In some embodiments, when the processor 37 determines that the temperature of the patient 5 exceeds a predetermined threshold or is below a predetermined threshold, the processor 37 communicates an alarm or alert to the monitoring client 6 (see FIG. 1) which can signal valve 25 to shut off fluid flow to the patient 5, send an alert to a remote communicator, and/or notify a caregiver of the condition via an internal speaker 42 or vibration motor 43 within the infusion site monitor 26. The patient temperature sensor 35 may utilize a temperature sensitive material, a positive temperature-coefficient material, a negative temperature-coefficient material, or other temperature sensor technology.

The ambient air temperature sensor 36 is in operative communication with the processor 37. The ambient air temperature sensor 36 can measure, estimate, and/or determine the temperature of the ambient air within the infusion site monitor 26, or in other embodiments, the temperature of the air outside of the infusion site monitor 26. In some embodiments, when the processor 37 determines that the temperature from the ambient air temperature sensor 36 exceeds a predetermined threshold or is below a predetermined threshold, the processor 37 communicates an alarm or alert to the monitoring client 6 (see FIG. 1) which can signal valve 25 to shut off fluid flow to the patient 5. The ambient air temperature sensor 36 may utilize a temperature sensitive material, a positive temperature-coefficient material, a negative temperature-coefficient material, or other temperature sensor technology.

Figure 3:
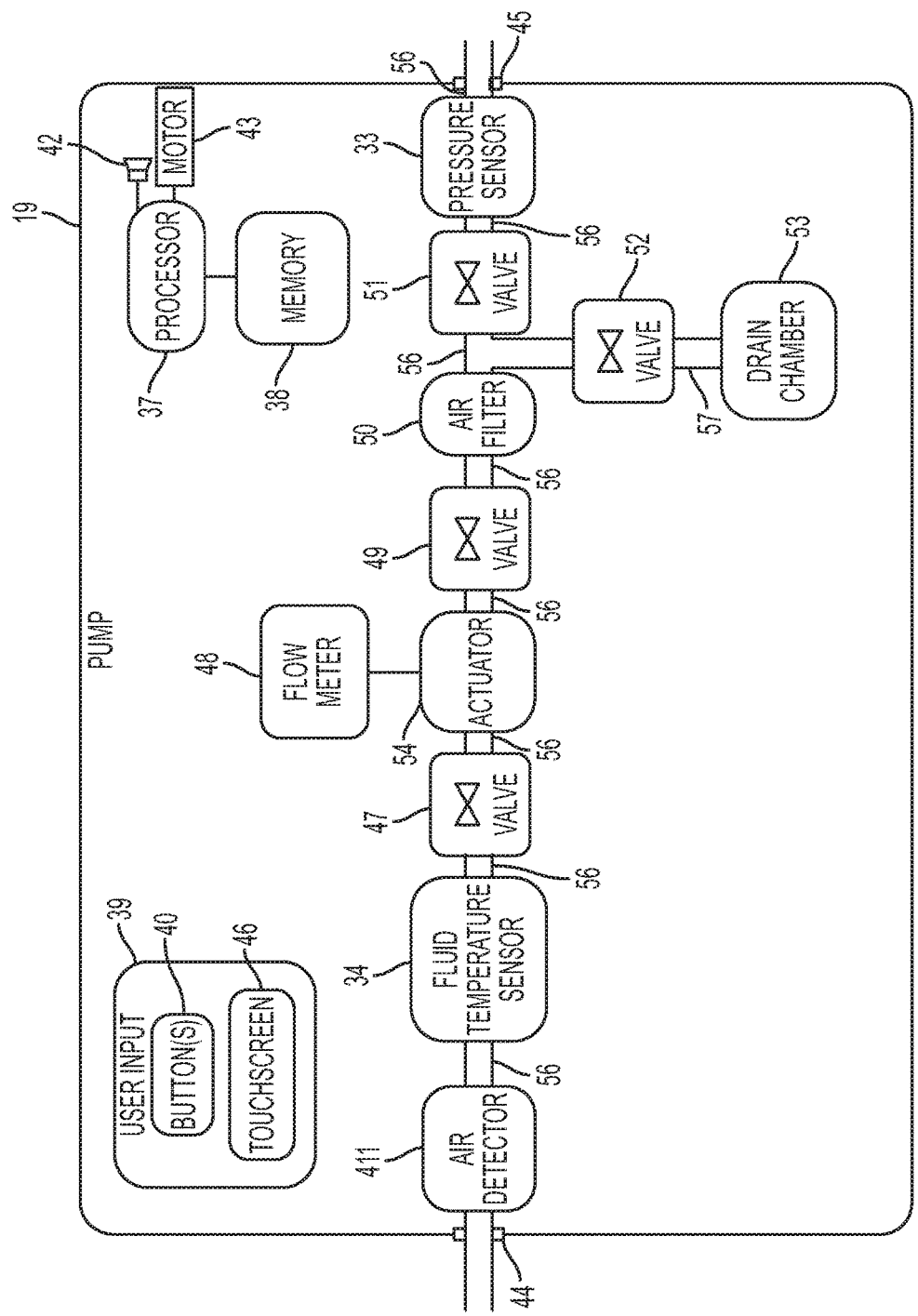
FIG. 3 shows a block diagram of a pump for infusing liquid of the system of FIG. 1 in accordance with an embodiment of the present disclosure.

Referring to the drawings, FIG. 3 shows a block diagram of a pump 19 for infusing liquid of the system 1 of FIG. 1 in accordance with an embodiment of the present disclosure. Although the pump 19 of FIG. 3 is described as being one of the pumps 19, 20, and 21 of FIG. 1, the pump 19 of FIG. 3 may be one or more of the pumps 19, 20, and 21 of FIG. 1.

Pump 19 includes a processor 37 coupled to a memory 38. The processor 37 is in operative communication with the memory 38 to receive processor executable instructions configured for execution on the processor 37. In some embodiments, the processor 37 is, optionally, in operative communication with the user input 39, the air detector 411, the fluid temperature sensor 34, valves 47, 49, 51 and 52, a flow meter 48, an actuator 54, an air filter 50, a drain chamber 53, and/or a pressure sensor 33.

The pump 19 in FIG. 3 includes an actuator 54 which operates on fluid contained within the tubing 56 flowing through the pump. The actuator 54 may directly operate on the tube 56, or may actuate against one or more membranes contained within the actuator 54. In some embodiments, the valves 47 and 49 cooperate with the actuator 54 to pump fluid, e.g., liquid, from the input port 44 to the output port 45 through the tube 56. In some embodiments of the present disclosure, the pump 19 contains no internal tubing and may interface with external tubing.

The air filter 50 filters out air from the tube 56. In alternative embodiments, the air filter 50 is upstream from the air detector 411. Valve 52 can activate to allow air to enter in from the tube 56 into a drain chamber 53 via a diversion tube 57.

Figure 4:
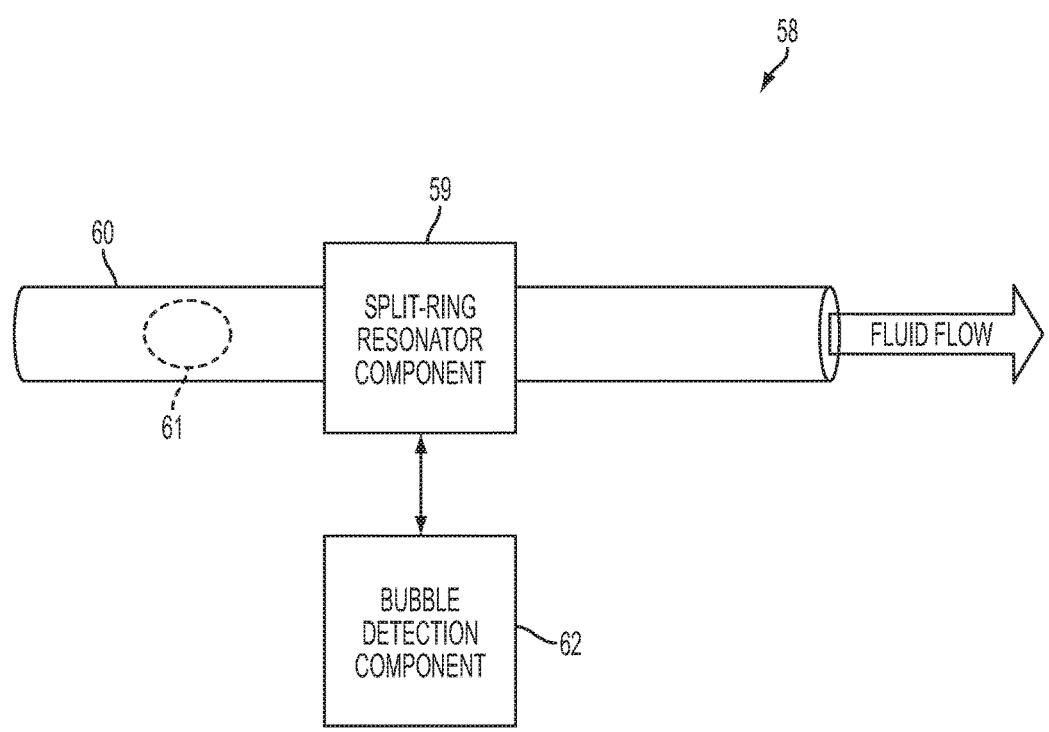
FIG. 4 shows a block diagram of a system for detecting a bubble within a fluid line in accordance with an embodiment of the present disclosure.

FIG. 4 shows a block diagram of a system 58 for detecting a bubble 61 within a fluid line 60 (herein used interchangeably with "tube") in accordance with an embodiment of the present disclosure. The system 58 for detecting a bubble may be the air detector 24 of FIG. 1, the air detector 410 of FIG. 2, and/or the air detector 411 of FIG. 3. The system 58 for detecting a bubble 61 may also be a component in any number of other systems, processes, applications, etc. including an air detector or device which would benefit from the use of such a detector. The system 58 may be used more broadly in applications to determine the presence, absence, or change in state of various materials or substances in or proximal to the system 58.

Relating specifically to the medical field for exemplary purposes only, the system 58 for detecting a bubble 61 may be used in a dialysis pump, an infusion pump, or other fluid delivery device. In specific embodiments, the system 58 may be used for detecting a primed vs. an unprimed tube 60 and/or may be used to facilitate automated-priming of the tube 60. In other specific embodiments, the system 58 may be used for detection of an unfilled tube 60 (e.g., detecting the presence of an air- vs. a fluid-filled tube 60). In some example embodiments, the system 58 may be used for detection of an air bubble 61 and or size of an air bubble 61 in a fluid line 60. In yet other specific embodiments, the system 58 may be used for determining whether or not a tube 60 has been inserted or is properly inserted into a larger medical device, such as an infusion pump. In other embodiments, the system 58 may be used to detect a multiplicity of scenarios, such as, but not limited to, any combination of those listed above.

The system 58 shown in FIG. 4 includes a split-ring resonator component 59 operatively coupled to a fluid line 60 (e.g., an intravenous fluid line) and a bubble detection component 62. The split-ring resonator component 59 and the bubble detection component 62 are operatively coupled together.

The split-ring resonator component 59 includes at least one split-ring resonator (often abbreviated herein as "SRR"). The split-ring resonator component 59 may also include a transmitting antenna configured to transmit energy (e.g., electromagnetic energy, such as microwave energy) into the at least one SRR and a receiving antenna configured to receive the energy from the transmitting antenna and/or the one or more SRRs. The split-ring resonator component 59 may be arranged such that the one or more SRRs cause a tunneling effect or increased frequency selective coupling to occur between the antennas.

The one or more SRRs of the split-ring resonator component 59 each have at least one gap that is affected by properties of the surrounding materials. Properties of the surrounding material may cause the behavior of the SRR within the split-ring resonator component 59 to change. For example, surrounding materials of differing dielectric properties will alter the behavior of the SRR. The resonant frequency of the SRR within the split-ring resonator component 59, for example, will change as a function of the dielectric properties of the surrounding material. The split-ring resonator component 59 and bubble detector component 62 may be used in any system where a dielectric change may correlate to a condition of interest beyond only in the detection of bubbles.

Referring specifically to FIG. 4, the bubble 61 has different dielectric properties than the surrounding fluid in the fluid line 60. Differences in the dielectric properties of the bubble 61 as compared to the fluid affects the one or more SRRs within the split-ring resonator component 59 by, for example, altering the capacitance of the one or more SRRs and therefore shifting the resonant frequency of the one or more SRRs when the bubble 61 is located near the split-ring resonator component 59. This shift may be observed and utilized by a bubble detection component 62 to determine the presence of the air bubble 61 within the fluid line 60.

This effect may also be used to determine a variety of other information about a fluid line 60 as mentioned above. For non-limiting exemplary purposes, this effect may be used to determine the presence of one or more bubbles 61 or the approximate size of a bubble or bubbles 61 within the fluid line 60. The effect, for example, may also be used to sense the presence or the absence of liquid within the tube 60. In some embodiments, the effect may indicate the absence of a tube 60 within a raceway 86 (see FIG. 20). In some embodiments, the effect may indicate the presence of a tube 60 within a raceway 86 or may be used to determine if a tube 60 has been correctly inserted into a raceway 86.

The bubble detection component 62 may be operatively coupled to the split-ring resonator component 59. The bubble detection component 62 may generate energy (e.g., electromagnetic energy such as microwave energy), apply the energy to a transmitting antenna of the split-ring resonator component 59, and receive the energy from a receiving antenna within the split-ring resonator component 59. The bubble detection component 62 may measure parameters of the energy to detect information about the fluid line 60, for instance, whether or not a bubble 61 is present in the fluid line 60. In some embodiments, the bubble detector component 62 may measure only a single parameter, or in other embodiments, the bubble detector component 62 may measure a plurality of parameters. The bubble detector component 62 may measure one or any combination of parameters, such as, but not limited to, those described below. The measured parameter or parameters may be analyzed to determine whether or not the parameter or parameters correlate to the existence of one or more conditions of interest. The parameters may be affected by the dielectric properties surrounding one or more SSRs within the split-ring resonator component 59. Some parameters may be calculated by a processor using directly-measured parameters.

In some embodiments, the bubble detection component applies a test signal to the split-ring resonator component 59 having one or more frequencies to the split-ring resonator component to determine one or more parameters correlated to, related to, or of one or more SSRs within the split-ring resonator component 59.

The bubble detector component 62 may measure a parameter such as a group delay caused by an SRR within the split-ring resonator component 59. In such embodiments, the group delay may be measured as the electromagnetic signal imparted on or applied to the SRR in time over a range of frequencies. The measured parameter of group delay may correlate to one or more conditions of interest, e.g. a condition where an air bubble 61 is present in the tube 60. The bubble detector component 62 may be configured to recognize such a correlation between the group delay and the condition of interest to determine when a bubble 61 is near or within the split-ring resonator component 59. The frequency at which the peak group delay occurs within a frequency range may be used to determine whether or not a bubble 61 is near or within the split-ring resonator component 59. Predetermined ranges may be used to determine if a bubble is present in the tube 60.

For example, if the peak group delay occurs within a first predetermined range of frequencies, the bubble 61 may be determined to exist at or near the split-ring resonator component 59; likewise, if peak group delay occurs within a second predetermined range of frequencies, the bubble 61 is determined to not exist at or near the split-ring resonator component 59. In some embodiments, the minimum group delay is used.

The bubble detector component 62 may measure a parameter such as a propagation delay cause by an SSR within the split-ring resonator component 59. The measured parameter of propagation delay may correlate to one or more conditions of interest, e.g. a condition where an air bubble 61 is present in the tube 60. The bubble detector component 62 may be configured to recognize such a correlation between the propagation delay and the condition of interest to determine when a bubble 61 is near or within the split-ring resonator component 59. The frequency at which the peak propagation delay (or minimum propagation delay) occurs within a frequency range may be used to determine whether or not a bubble 61 is near or within the split-ring resonator component 59. That is, predetermined ranges may be used to determine if a bubble 61 is present in the tube 60 at or near the split-ring resonant or component 59.

In some embodiments, the bubble detector component 62 may measure a parameter such as the phase angle of a test signal which is applied to an SRR and received by a receiving antenna of the split-ring resonator component 59. In some embodiments the bubble detection component 62 may compare the phase angle of the applied test signal to the test signal received by a receiving antenna of the split-ring resonator component 59. The measured parameter of phase angle may be checked to determine if it corresponds to one or more conditions of interest (e.g., whether the bubble 61 is present). That is, predetermined ranges may be used to determine if a bubble 61 is present in the tube 60 at or near the split-ring resonant or component 59.

In some embodiments, the bubble detector component 62 may measure a parameter such as the phase response of an SRR within the split-ring resonator component 59. In some embodiments, the bubble detector component 62 may measure the phase response of an SRR over a predetermined range of frequencies (e.g. microwave frequencies or a specified range of microwave frequencies). The measured parameter of phase response may then be interpreted to determine if at least one condition of interest exists. Predetermined ranges may be used to determine if a bubble 61 is present in the tube 60 at or near the split-ring resonant or component 59.

In some embodiments, the bubble detector component 62 may measure a parameter such as the amplitude of a test signal which is applied to an SRR and received by a receiving antenna of the split-ring resonator component 59. In some embodiments, the bubble detection component 62 may compare the amplitude of the applied test signal to the test signal received by a receiver antenna of the split-ring resonator component 59. The measured parameter of amplitude may be scrutinized to determine if it correlates to one of more conditions of interest by using predetermines ranges, e.g., using predetermined ranges to determine if a bubble 61 is present in the tube 60 at or near the split-ring resonant or component 59.

In some embodiments, the bubble detector component 62 may measure a parameter such as the resonant frequency of an SRR. In some embodiments the bubble detector component 62 may monitor for a shift in the resonant frequency of an SRR. The measured parameter of resonant frequency may be used to determine if it correlates to one or more conditions of interest.

In some embodiments, the bubble detector component 62 may measure a parameter such as the anti-resonance of an SRR. In some embodiments, the bubble detector component 62 may monitor for a shift in the anti-resonant frequency of an SRR. The measured parameter of anti-resonance may then be considered to determine if it correlates to one or more condition of interest, e.g., using predetermined ranges to determine if a bubble 61 is present in the tube 60 at or near the split-ring resonant or component 59.

In some embodiments, the bubble detector component 62 may measure a parameter such as the frequency response an SRR. In some embodiments, the frequency response may be measured over a predefined frequency range (e.g. the microwave spectrum or a specific frequency range within the microwave spectrum). The measured parameter of frequency response may then be analyzed to determine if it correlates to the existence of one or more conditions of interest, e.g., using predetermined ranges to determine if a bubble 61 is present in the tube 60 at or near the split-ring resonant or component 59.

In some embodiments, the bubble detector component 62 may measure a parameter such as the impedance of an SRR. In such embodiments, the measured impedance of the SRR may be used to determine if it correlates to at least one condition of interest, e.g., using predetermined ranges to determine if a bubble 61 is present in the tube 60 at or near the split-ring resonant or component 59.

In other embodiments, the bubble detector component 62 may measure a parameter such as the quality factor (hereafter "Q") of an SRR. Similarly, the bubble detector component 62 may measure a parameter such as the bandwidth of an SRR. Again the measured parameter of Q and/or bandwidth may be evaluated to determine if it correlates to one or more conditions of interest, e.g., using predetermined ranges to determine if a bubble 61 is present in the tube 60 at or near the split-ring resonant or component 59.

In some embodiments, the bubble detector component 62 may measure one or any combination of the S11, S12, S21, or S22 parameters of the SRR component 59. The S11 parameter is the input port voltage reflection coefficient. The S12 parameter is the reverse voltage gain. The S21 parameter is the forward voltage gain. The S22 parameter is the output port voltage reflection coefficient. In such embodiments the measured S-parameter or S-parameters may be analyzed to determine whether or not they correlate to one or more conditions of interest.

Additionally or alternatively, in some exemplary embodiments, the bubble detection component 62 may monitor for a change in one or more of these parameters to detect the bubble 61. In some embodiments, the bubble detector component 62 may monitor for a change greater than a predetermined threshold or a change beyond a predetermined initial measurement. In other embodiments, the bubble detection component 62 may detect a state of a raceway 86 (see FIG. 28) adjacent to an SRR using one or more parameters of an SRR or any other condition of interest.

Figure 5A:
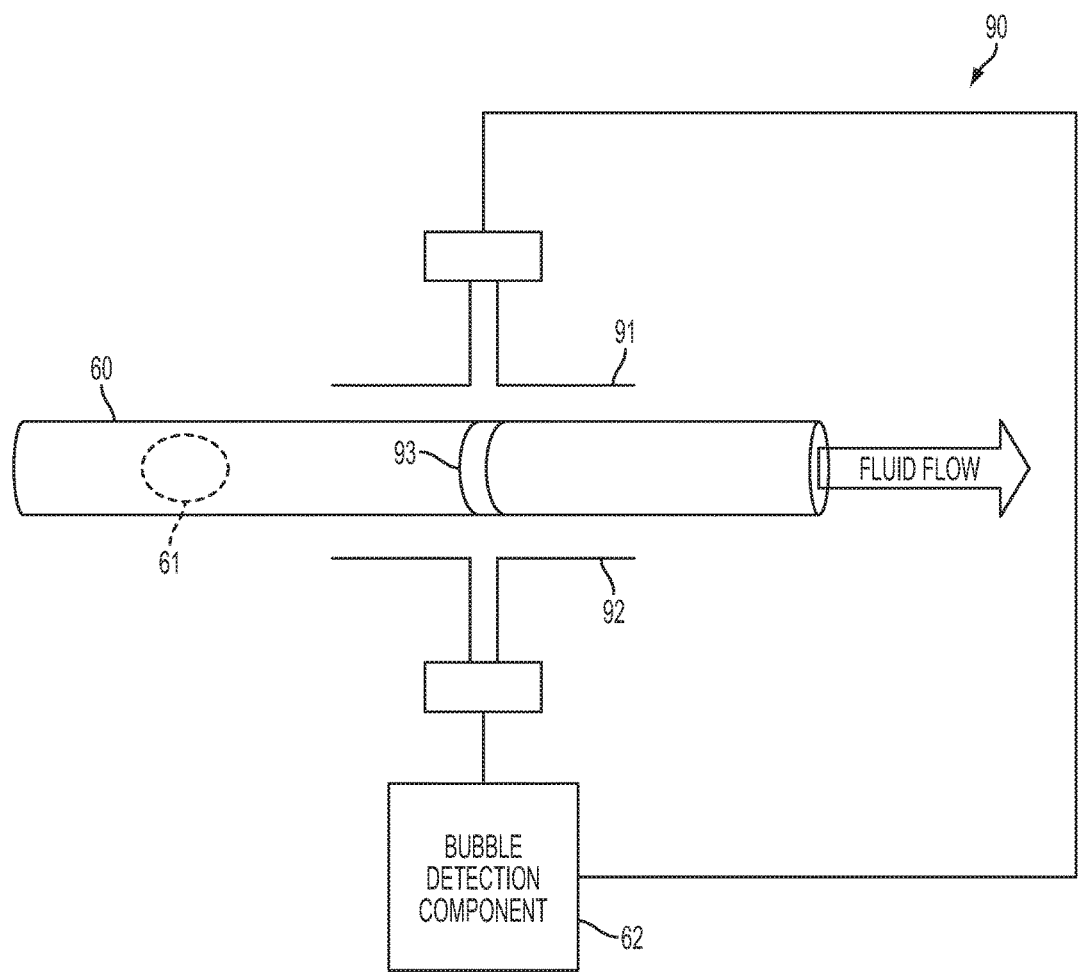
FIG. 5a shows a diagram of a system for detecting a bubble within a fluid line using two dipole antennas in accordance with an embodiment of the present disclosure.

FIG. 5*a* shows a diagram of a system 90 for detecting a bubble 61 within a fluid line 60 using two dipole antennas 91 and 92 in accordance with an embodiment of the present disclosure. The diagram of the system 90 in FIG. 5*a* may be one specific example embodiment of the system 58 shown in FIG. 4. The dipole antennas 91 and 92 in combination with an SRR 93 may form an SRR component, such as the SRR component 59 shown in FIG. 4; a housing may also be included as part of the SRR component 59. Some embodiments may include more SRRs than just the single SRR 93 shown in FIG. 5*a*.

In the example embodiment, the dipole antenna 92 transmits microwave energy. The microwave energy transmitted from the dipole antenna 92 is received by the SRR 93. As shown in the exemplary embodiment in FIG. 5*a*, the SRR 93 is arranged such that the tube 60 is within its center.

The microwave energy is received by the receiving antenna 91 after passing through the SRR 93. The bubble detection component 62 may detect a bubble 61 or other condition of interest by measuring one or more parameters corresponding to the SRR 93. This is so because the properties of the bubble 61 may alter the parameter when the bubble 61 is at or near the SRR 93. In other embodiments, the bubble detection component 62 may detect a state of a raceway 86 (see FIG. 20) adjacent to the SRR 93 using one or more parameters of the SRR 93.

Figure 5B:
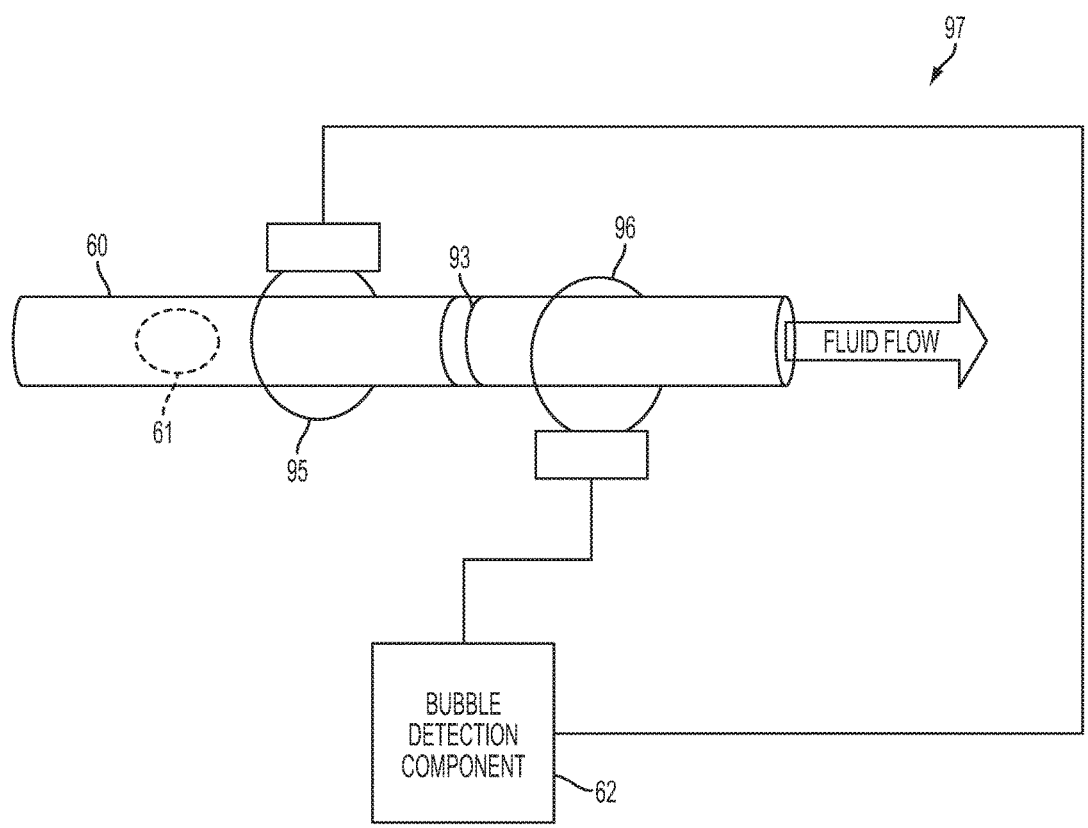
FIG. 5b shows a diagram of a system for detecting a bubble within a fluid line using two loop antennas in accordance with an embodiment of the present disclosure.

FIG. 5*b* shows a diagram of a system 97 for detecting a bubble 61 within a fluid line 60 using two loop antennas 95 and 96 in accordance with an embodiment of the present disclosure. The diagram of the system 97 in FIG. 5*b* may be another specific example embodiment of the system 58 shown in FIG. 4. The transmitting loop antenna 96 and receiving loop antenna 95 in combination with the SRR 93 may form an example SRR component such as the SRR component 59 shown in FIG. 4. Some embodiments may include one or more SRRs in addition to the single SRR 93 shown in FIG. 5*b*.

In the example embodiment in FIG. 5*b*, the transmitting loop antenna 96 transmits microwave energy which may be absorbed by the SRR 93. The receiving loop antenna 95 receives the microwave energy after it passes the SRR 93. The bubble detection component 62 may detect a bubble 61, for example, by measuring one or more parameters corresponding to the SRR 93. This is because the properties of the bubble 61 may alter the measured or estimated parameter when the bubble 61 is at or near the SRR 93.

The bubble detection component 62 may measure one of more parameters using the microwave energy to determine when a bubble 61 affects one or more parameters of the microwave energy. For example, the dielectric loading of a gap of the SRR 93 alters the transmission of the microwave energy between the loop antennas 95 and 96. Thus a parameter or parameters relating to the transmission of energy may be used to determine the presence of the bubble 61. As mentioned above, this is because the bubble 61 would cause differing dielectric loading than that created when only fluid is present in the fluid line 60. In other embodiments, the bubble detection component 62 may detect other conditions of interest such as a state of a raceway 86 (see FIG. 28) adjacent to the SRR 93 using one or more parameters of the SRR 93.

Figure 5C:
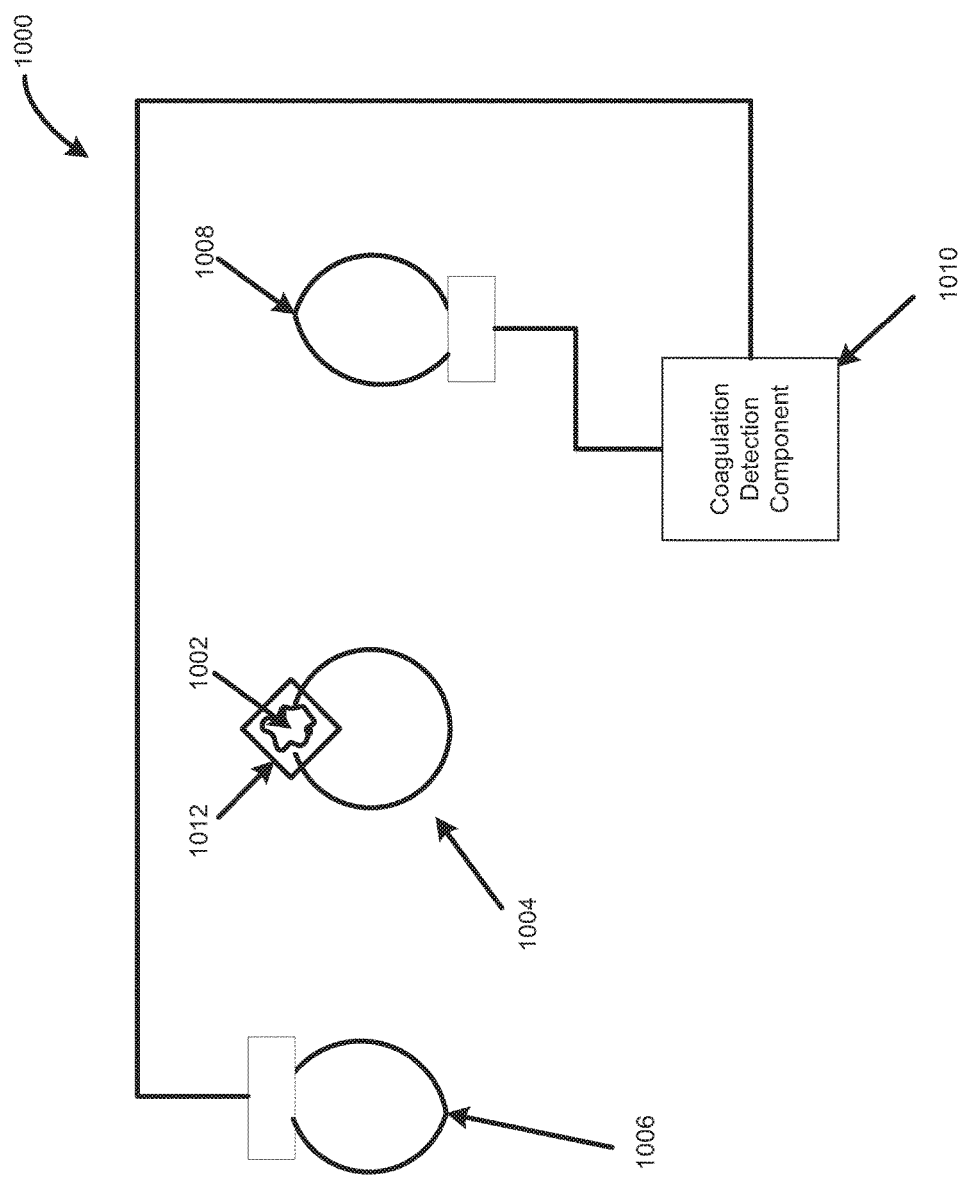
FIG. 5c shows a diagram of a system for monitoring the coagulation of blood using to loop antennas in accordance with an embodiment of the present disclosure.

In some embodiments, blood coagulation may be monitored by a similar system. An example blood coagulation monitoring system 1000 is shown in FIG. 5c. In such a system 1000, a sample of blood 1002 may be brought into proximity of an SRR component 1004. In such embodiments, the fluid line 60 (shown in FIGS. 5a-5b) may not be included. In such embodiments, the transmission of energy will be similarly altered by changing dielectric loading as the sample of blood 1002 coagulates. The example system 1000 includes a transmitting loop antenna 1006 which transmits microwave energy that may be absorbed by the SRR component 1004. The example system 1000 also includes a receiving loop antenna 1008 which receives the microwave energy after it passes the SRR component 1004.

By monitoring one or more parameters of the transmitted microwave energy with a coagulation detection component 1010 which performs a role analogous to the bubble detection component 62, coagulation time may be determined. This may be used to report PT-INR. For example, as the sample of blood 1002 coagulates and its dielectric properties change, a parameter such as the resonant frequency of the SRR component 1004 may change. Using the example of resonant frequency of the SRR component 1004, the resonant frequency of the SRR component 1004 may be monitored by a coagulation detection component 1010 and analyzed to determine if it correlates to a state in which the sample of blood 1002 has coagulated.

In some embodiments, the sample of blood 1002 may be hermetically sealed after it is drawn. This may help to ensure that dielectric changes in the sample of blood 1002 are due to coagulation and not, for example, due to the drying of the sample of blood 1002. This may help to ensure more accurate and consistent results. In some embodiments, such as the embodiment in FIG. 5c, the sample of blood 1002 may be placed on a disposable 1012 which may be placed in proximity to an SRR component 1004. After the coagulation time for sample of blood 1002 has been measured, the disposable 1012 may be discarded. When it is desirable to measure a subjects blood coagulation time again another sample of blood 1002 may be drawn and placed on a new disposable 1012 for analysis. This may allow the system 1000 to be easily reusable. It may also make the system 1000 easy to use in a non-clinical environment such as a home or residence.

FIGS. 6 and 8-14 and show examples of a number of various possible SRR embodiments. FIG. 6 shows an example embodiment of a single ring, single split SRR 200. As shown, the SRR 200 includes a single conductive ring 202 which includes a single split 204. The conductive ring 202 is roughly circular and roughly of uniform width and thickness along its entire arc. The conductive ring 202 may act as an inductor. The single split 204 defines a gap 206. The edges of the gap 206 may be approximately parallel as is shown in FIG. 6. The single split 204 may act as a parallel plate capacitor. As such, the SRR 200 in FIG. 6 may be considered to form a simple LC circuit. The SRR 200 has a resonant frequency which may be determined as follows:

$$f_0 = \frac{1}{2\pi\sqrt{LC}},$$

where f is the resonant frequency in hertz, L is the inductance in henries, and C is the capacitance in farads. As delineated by this equation, the resonant frequency f is dependent upon the inductance L and the capacitance C. Any change in either of these values will result in a change of the resonant frequency f.

FIG. 7 shows a close-up view of a split 214 in the conductive ring 212 of an SRR 210. In the view shown in FIG. 7, only a portion of the conductive ring 212 of the SRR 210 is visible. The portion of the conductive ring 212 shown is not arced, but rather is essentially straight. The split 214 defines a gap 216. As in the embodiment in FIG. 6, the edges of the gap 216 are generally parallel to one another. Thus the split 214 may act as a parallel plate capacitor.

The embodiment of the SRR 210 shown in FIG. 7 additionally includes two capacitive extensions 218. In the example embodiment, the capacitive extensions 218 extend substantially perpendicularly from the conductive ring 212. One edge of each capacitive extension 218 may be continuous with a respective edge of the gap 216. These capacitive extensions 218 serve to increase the overall capacitance of the SRR 210. The capacitance of a parallel plate capacitor may be determined as follows:

$$C = \varepsilon_0 \frac{A}{d}$$

where C is capacitance, $\varepsilon_0$ is the permittivity of empty space, A is the area of one of the plates, and d is width the gap 216.

As indicated above, the capacitance C increases linearly with area A. The capacitive extensions 218 serve to increase the area A of the parallel plate capacitor created in the SRR 210. In alternate embodiments, the capacitive extensions 218 may be longer or shorter. The capacitive extensions 218 and gap 214 may also be otherwise manipulated in any number of other ways, some of which are described herein, to achieve a desired capacitive value. In other embodiments, the width of the gap 214 may be changed to vary capacitance. In some embodiments a surface mount capacitor such as a voltage controlled varactor diode may be placed in the gap 216 to alter the capacitance as well.

FIG. 8 shows another exemplary SRR 220 which is similar to the SRR 200 shown in FIG. 6, but includes capacitive extensions 228. The SRR 220 includes a single conductive ring 222 which includes a single split 224. The single conductive ring 222 is roughly circular and roughly of uniform width and thickness along its entire arc. The conductive ring 222 may act as an inductor. As in FIG. 6 and FIG. 7, the single split 224 defines a gap 226 whose edges are generally parallel to one another. Thus, the single split 224 may act as a parallel plate capacitor.

As above, the capacitive extensions 228 serve to increase the overall capacitance of the SRR 220. In the example embodiment, the capacitive extensions 228 extend substantially from the conductive ring 222. The parallel edges of the single split 224 are also oriented at an angle away from the conductive ring 222. The angle at which the single split 224 and capacitive extensions 228 are oriented may be selected to tailor the area A to a desired value.

By enlarging the total capacitance of an SRR, such as by using the extensions 228 of the SRR 220 shown in FIG. 8, the dielectric properties of the surrounding material will have more effect on the resonant frequency of the SRR. Consider the following equation to calculate capacitance of a capacitor with a dielectric material completely filling the space between its two plates:

$$C = \kappa_e C_0$$

where $C_0$ is the initial capacitance with nothing between the plates, $\kappa_e$ is the dielectric constant of the material placed between the plates, and C is the resulting capacitance with the dielectric present. If the dielectric constant remains the same, the higher the initial capacitance $C_0$, the larger the resulting capacitance value C will be. It should be noted that this equation is given for the sake of simplicity and demonstration and should not be construed to mean that the fluid line must completely fill or be at all disposed with the gap created by the split in an SRR. Since the electrical field created by a capacitor will "spill" beyond the gap between two plates, a dielectric placed outside of this gap may still have an effect on the capacitance of a capacitor.

As the dielectric properties of the surrounding material changes, the capacitance value C will also change. For example, the dielectric constant $\kappa_e$ of water (e.g. fluid in a fluid line) is 80, while that of air (e.g. a bubble in a fluid line) is 1.00059. The capacitance value C will be greater in the presence of water and lower in the presence of air. This is exaggerated when the initial capacitance $C_0$ is large. Consequentially, the resonant frequency will be different when an air bubble is performing the role of the dielectric relative to when the fluid is performing the role of the dielectric.

Figure 9:
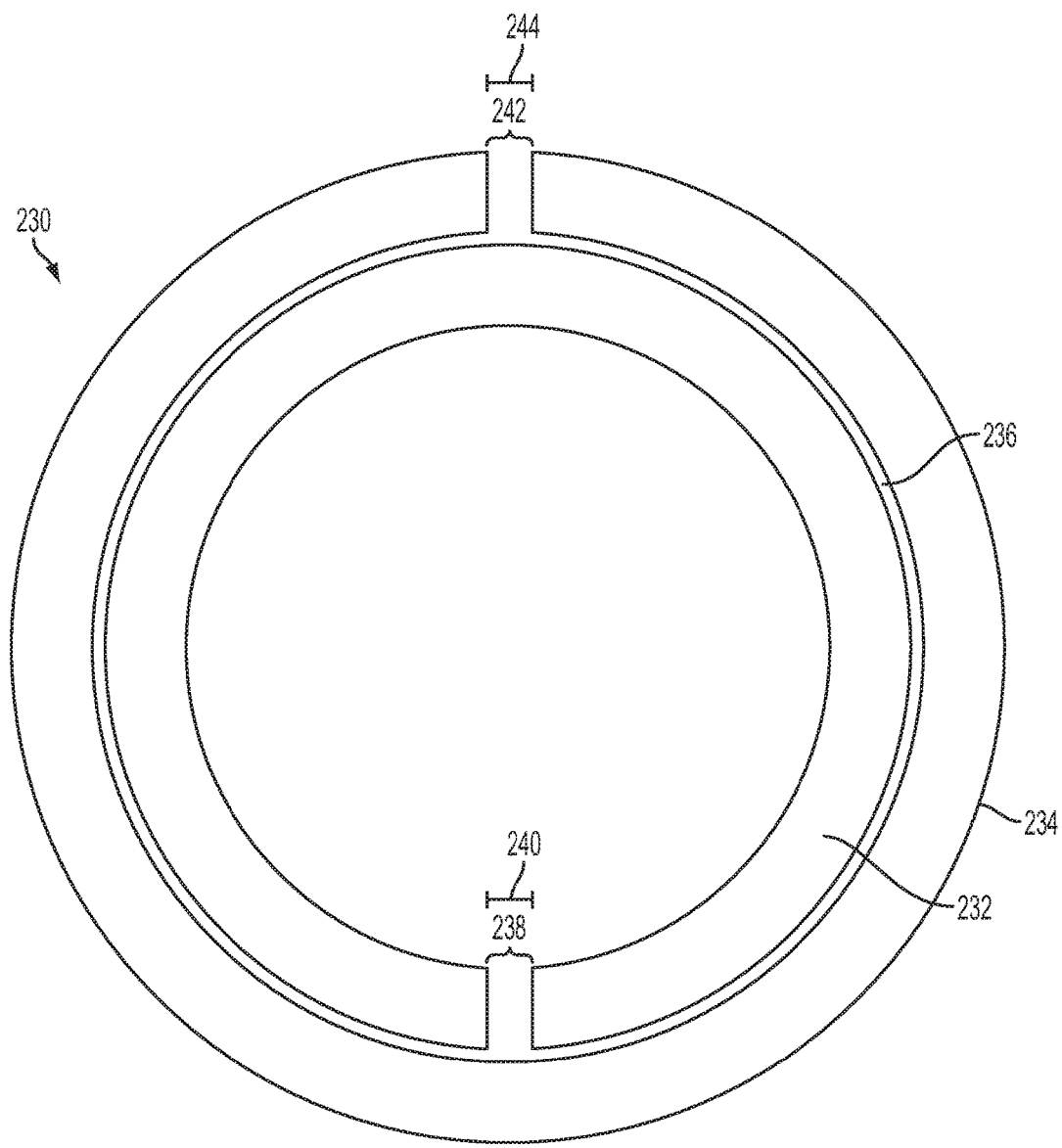

FIG. 9 depicts another example embodiment of an SRR 230. The SRR 230 includes an inner conductive ring 232 and an outer conductive ring 234 which are concentric. In the example embodiment in FIG. 9, the diameter of the inner conductive ring 232 is chosen such that there is an inner-outer ring gap 236 between the inner conductive ring 232 and the outer conductive ring 234. Inductance in the SRR 230 arises from the inner conductive ring 232, the outer conductive ring 234, and the inner-outer ring gap 236.

The inner conductive ring 232 includes a single inner ring split 238 which defines the edges of a gap 240. The edges of the gap 240 are roughly parallel to one another and thus form a parallel plate capacitor. Additionally, the outer conductive ring 234 includes a single outer ring split 242 which defines the edges of a gap 244. The gaps 240, 244 are disposed substantially 180° from one another to maximize capacitance by ensuring the charges induced by one ring is opposite that of the other. As would be understood by one skilled in the art, the inner-outer ring gap 236 also adds to the overall capacitance.

Figure 10:
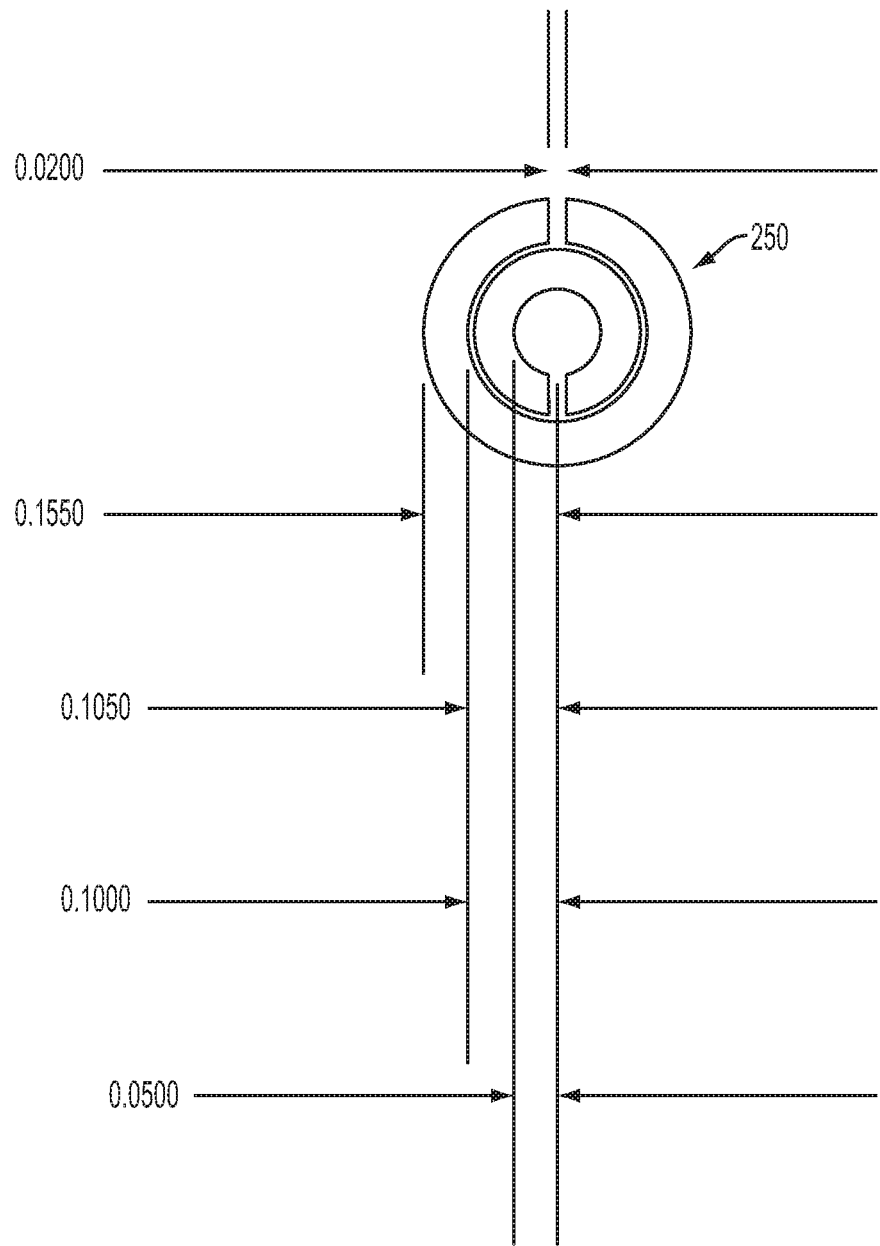

FIG. 10 shows a specific embodiment of an example SRR 250 similar to the SRR 230 shown in FIG. 9. FIG. 10 details specific dimensions for the SRR 250. In alternate embodiments, these dimensions may differ. As shown, the SRR 250 in FIG. 10 includes two concentric conductive rings which each have a single split. The inner conductive ring and the outer conductive ring of the SRR 250 are both approximately 0.0500 inches in width. The inner-outer ring gap is roughly 0.0050 inches in width. The split in the outer conductive ring is approximately 0.0200 inches in width while the split in the inner conductive ring is somewhat smaller in width. The distance from the inner edge of the inner conductive ring to the center point of the two conductive rings is approximately 0.0500 inches.

Figure 11:
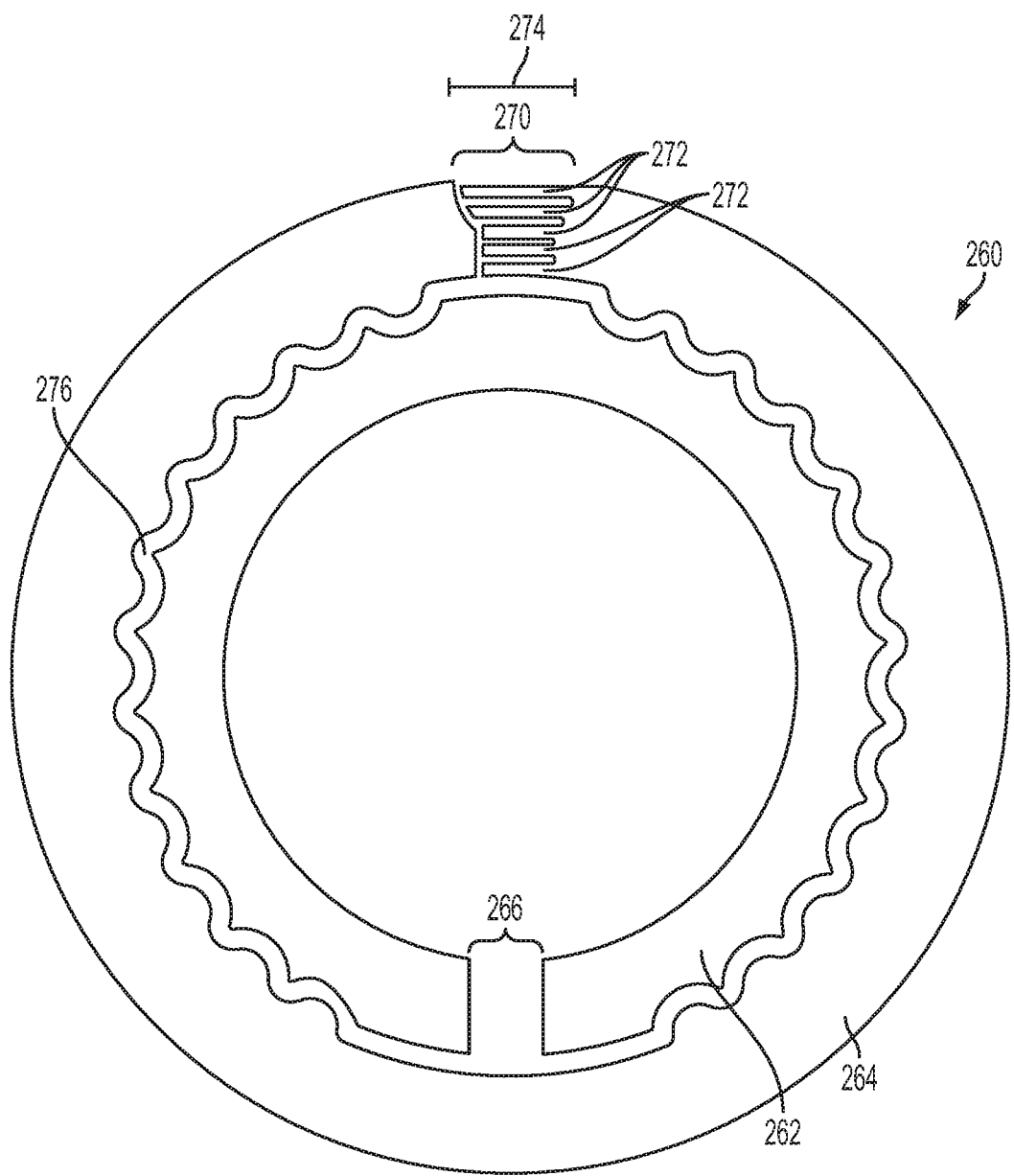

FIG. 11 depicts yet another exemplary embodiment of an SRR 260. As shown, the SRR 260 is similar to the SRR 230 shown in FIG. 9. The SRR 260 includes an inner conductive ring 262 and an outer conductive ring 264 which are concentric. The inner conductive ring 262 includes an inner ring split 266. The outer conductive ring 264 includes an outer ring split 270. The outer ring split 270 includes a number of capacitive extensions 272. As shown, the capacitive extensions 272 resemble fingers which protrude into the gap 274 created by the outer ring split 270. The capacitive extensions 272 project into the gap 274 in a fashion substantially parallel to one another and are continuous with the outer conductive ring 264. As is additionally shown, the edges of the gap 274 are not entirely straight. The tips of the capacitive extensions 272 in the example embodiment are oriented such that they are substantially parallel to the edge of the gap 274 they are most proximal to.

The capacitive extensions 272 shown in FIG. 11 serve to increase the capacitance of the SRR 260. In alternate embodiments, spacing, width, length, number, etc. of capacitive extensions 272 may differ. In some embodiments, the inner ring split 266 may include finger-like capacitive extensions (not shown), similar to the capacitive extensions 272 in the outer ring split 270. In such embodiments, the capacitive extensions 272 in the outer ring split 270 may or may not be present. Additionally, in some embodiments, a second set of capacitive extensions (not shown) may extend into the outer ring split 270 from the opposite side of the outer ring split 270 such that they may interdigitate with the capacitive extensions 272. Again, this would serve to increase the overall capacitance of the SRR 260.

The example SRR 260 shown in FIG. 11 also includes an inner-outer ring gap 276. The edges of the inner conductive ring 262 and outer conductive ring 264 defining the inner-outer ring gap 276 are ruffled. This ruffling may be created by varying the width of the inner conductive ring 262 and outer conductive ring 264.

As in FIG. 9 inductance in the SRR 260 arises from the inner conductive ring 262, the outer conductive ring 264 and the inner-outer ring gap 276. The ruffling increases the overall inductance of the SRR 260. The inner-outer ring gap 276 also adds capacitance to the SRR 260.

Figure 12:
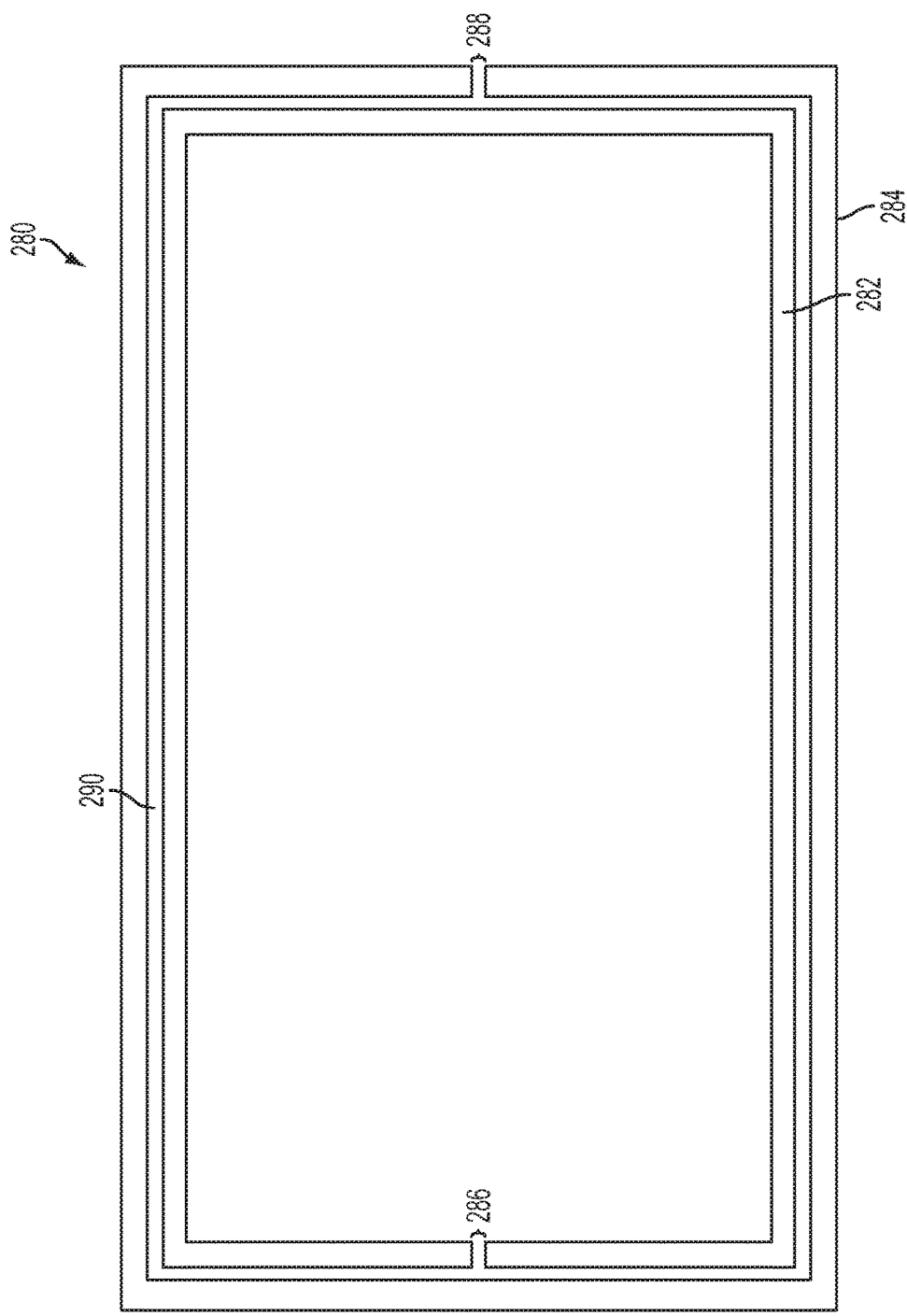

FIG. 12 depicts another example embodiment of an SRR 280 in accordance with an embodiment of the present disclosure. As in FIG. 12, the term "ring" may be used loosely herein to refer to structures which are not necessarily classically ring-like in shape, but when used in the place of a classic ring-like shape behave equivalently or similarly. The SRR 280 shown in FIG. 12 includes an inner conductive ring 282 and an outer conductive ring 284 both of which are rectangular in the example embodiment. The inner conductive ring 282 includes an inner ring split 286. The outer conductive ring 284 includes an outer ring split 288. The inner conductive ring 282 and outer conductive ring 284 are separated by an inner-outer ring gap 290. As shown in the example embodiment depicted in FIG. 12, the inner-outer ring gap 290 is of uniform width along its entire span. The inner-outer ring gap 290, inner conductive ring 282, and outer conductive ring 284 bring about the inductance in the SRR 280.

Figure 13:
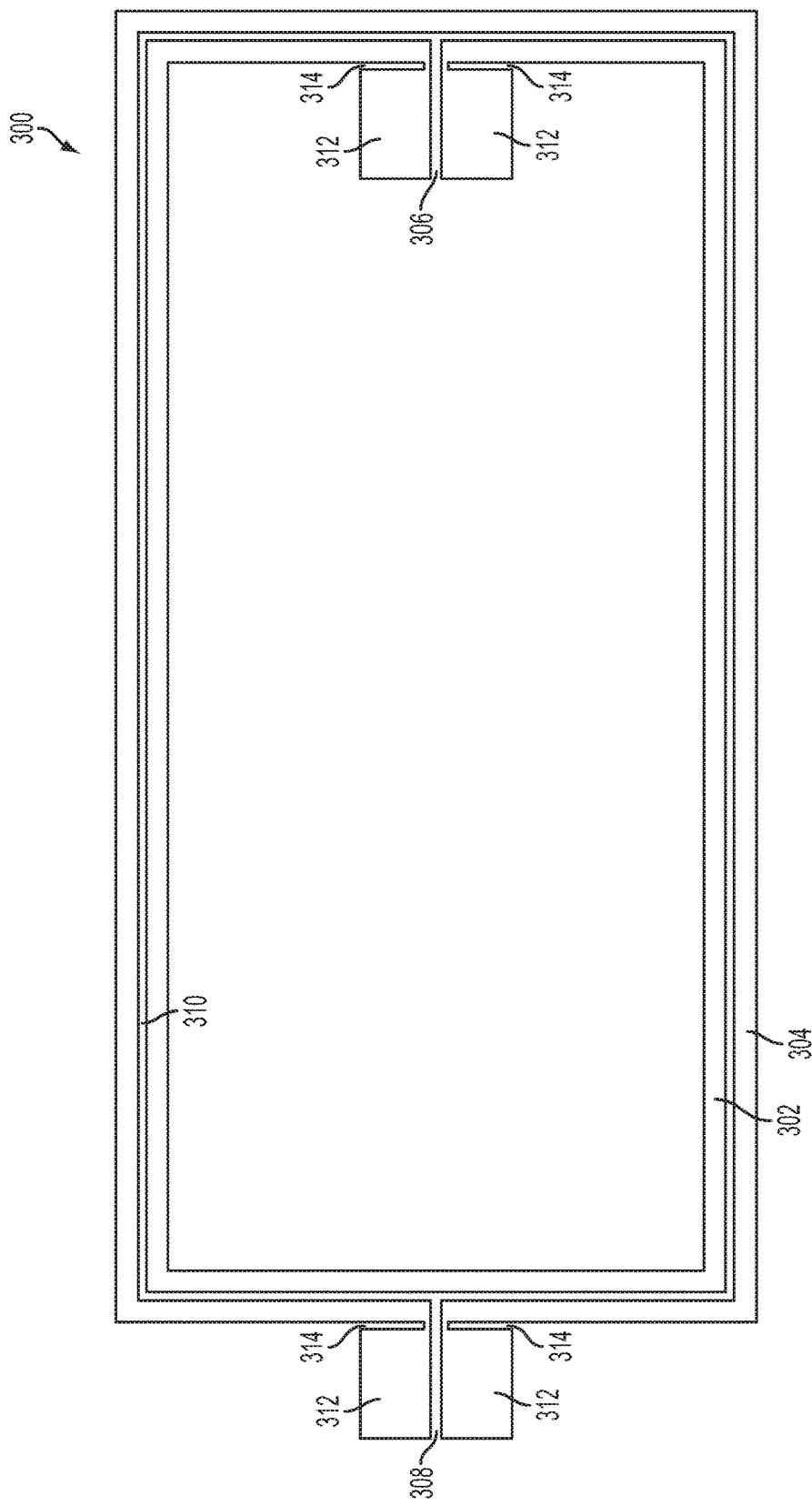

FIG. 13 depicts yet another SRR 300 embodiment. The SRR 300 shown in FIG. 13 includes an inner conductive ring 302 and an outer conductive ring 304. The inner conductive ring 302 and the outer conductive ring 304 are each rectangular similar to the SRR 280 shown in FIG. 12. The inner conductive ring 302 includes an inner ring split 306. The outer conductive ring 304 includes an outer ring split. 308. The inner conductive ring 302 and the outer conductive ring 304 are separated by an inner-outer ring gap 310 which is of uniform width along its entire expanse. As in FIG. 12, inductance arises from the inner conductive ring 302, outer conductive ring 304, and the inner-outer ring gap 310.

The inner ring split 306 and outer ring split 308 of the SRR 300 include capacitive extensions 312 in FIG. 13. As shown, the capacitive extensions 312 are similar to the capacitive extensions 218 shown in FIG. 7. The capacitive extensions 312 extend in a direction substantially perpendicular to the edges of the inner conductive ring 302 and the outer conductive ring 304. Differing from FIG. 7, however, the capacitive extensions 312 are only connected to the inner conductive ring 302 and outer conductive ring 304 by a thin bridge of material. This leaves a void 314 between the edges of the inner conductive ring 302 and the outer conductive ring 304 and each of their respective capacitive extensions 312. As in FIG. 7, the capacitive extensions 312 in FIG. 13 serve to increase the capacitance of the gap created by the splits 306, 308. The voids 314 also act as a capacitive gap increasing the overall capacitance of the SRR 300. Some capacitance is also introduced by the inner-outer ring gap 310.

Figure 14:
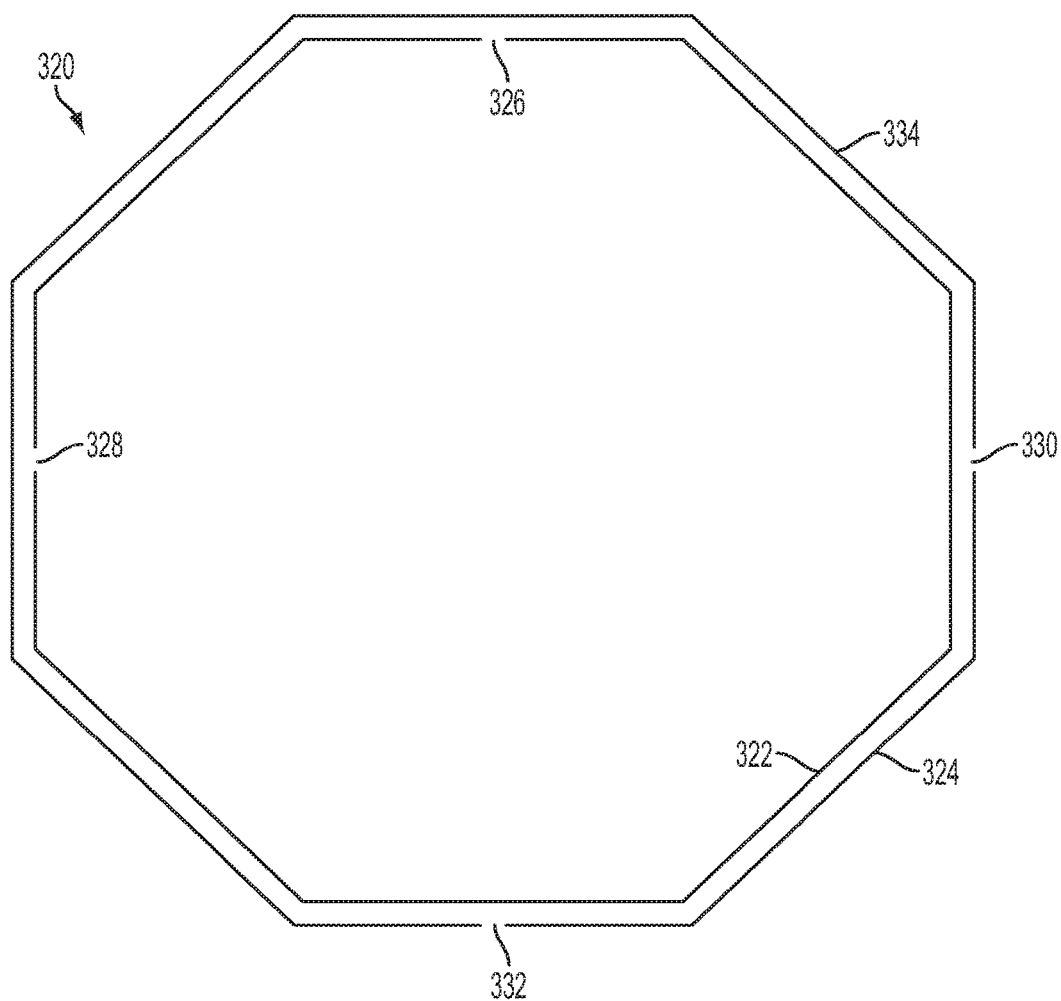

FIG. 14 depicts yet another example embodiment of an SRR 320. As shown, the SRR 320 includes an inner conductive ring 322 and an outer conductive ring 324. In the example embodiment, the inner conductive ring 322 and the outer conductive ring 324 are octagonal. In other embodiments, the inner conductive ring 322 and outer conductive ring 324 may be square, pentagonal, hexagonal, heptagonal, nonagonal, decagonal, undecagonal, dodecagonal, or any other suitable shape. The inner conductive ring 322 and the outer conductive ring 324 are separated by an inner-outer ring gap 334. The inductance arises from the inner conductive ring 322, outer conductive ring 324, and the inner-outer ring gap 334.

The inner conductive ring 322 includes two inner ring splits 326, 328. The outer conductive ring 324 includes two outer ring splits 330, 332. As is shown, the two inner ring splits 326, 328 are disposed opposite the two outer ring splits 330, 332. Alternate embodiments may include additional splits on each ring. Preferably, the splits of one ring are not oriented in line with the splits in the other ring. The additional splits increase the capacitance of the SRR 320. As mentioned above, the larger the initial capacitance value, the more the dielectric properties of surrounding materials will affect the overall capacitance of the SRR 320.

Figure 15:
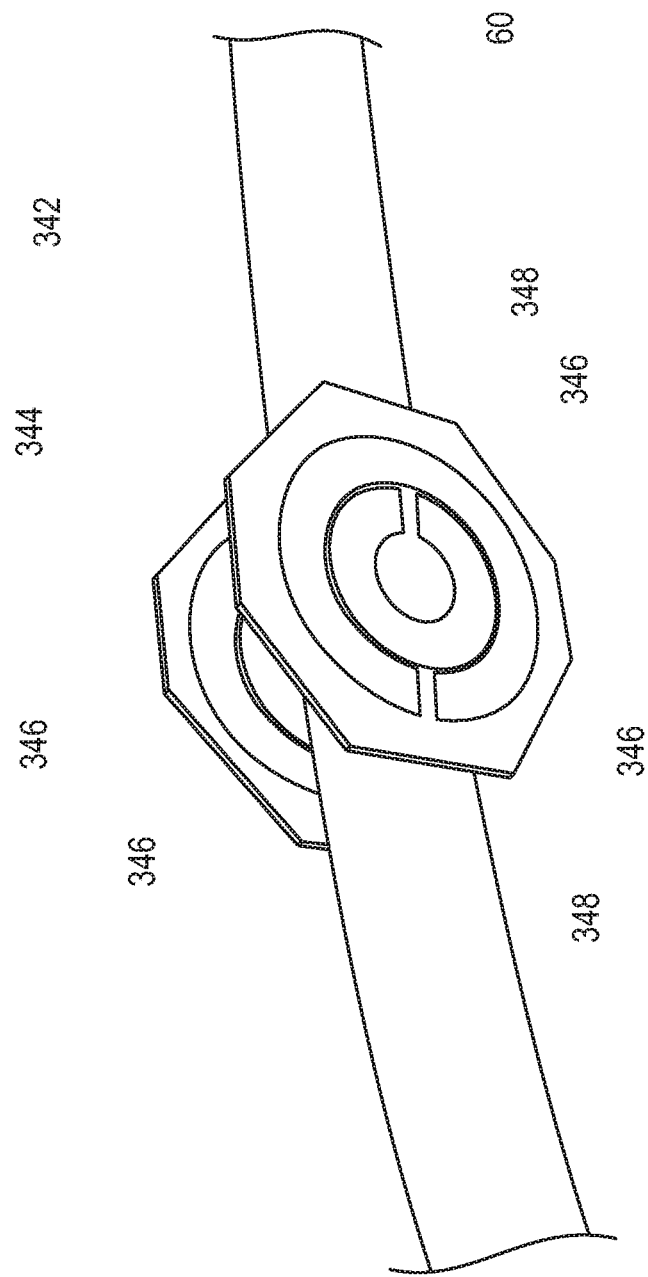
FIG. 15 shows an example transmitting antenna and an example receiving antenna in place on either side of a fluid line.

FIG. 15 shows an example transmitting antenna 342 and receiving antenna 344 positioned near a fluid line 60. The transmitting antenna 342 and the receiving antenna 344 each include two concentric conductive rings 346 with a single split 348 in each ring. In other embodiments the transmitting antenna 342 and the receiving antenna 344 may be any other suitable type of antenna. The transmitting antenna 342 and the receiving antenna 344 are arranged in a preferred orientation where flank both sides of the fluid line 60.

A split ring resonator component including a split-ring resonator (not shown in FIG. 15) such as any of those described herein may be placed near the fluid line 60 and between the transmitting antenna 342 and the receiving antenna 344. Energy, e.g. microwave energy, may be supplied to the transmitting antenna 342. This energy may then be transmitted by the transmitting antenna 342. The energy received by the receiving antenna 344 may pass to a bubble detection component (not shown).

As mentioned above, depending on the dielectric properties of the surrounding materials, e.g. the tube 60 and its contents, various parameters of the transmitted energy will change. The capacitance of a gap in an SRR, for example, will change depending on the dielectric properties of the surrounding materials. If, for example, an air bubble is traveling through the fluid line 60, the gap capacitance would be different than when only fluid is traveling through the fluid line 60. Since the capacitance of an SRR alters the transmission of energy in a split ring resonator component as described above, the capacitance change may indicate the existence of an air bubble. These changes may be used by a bubble detection component to determine, for example, the state of the tube 60.

Some embodiments of the system for detecting a bubble (see FIG. 4) may include a housing. The housing may house, hold, include attachment sites, etc. for a number or all of the components which are included in the system. The housing may for example hold a split ring resonator component and a bubble detecting component. The housing may also include a feature in which a fluid line may be seated.

FIGS. 16-19 show an example embodiment of a housing 370 for a split ring resonator component (see, for example, FIG. 4). As shown, the housing 370 includes a substantially rectangular block 372 having a U-shaped valley 374. In other embodiments, the housing 370 may be any other suitable shape. The U-shaped valley 374 is recessed into the rectangular block 372 along the longitudinal centerline of the rectangular block 372. The U-shaped valley 374 is recessed into the rectangular block 372 a distance slightly smaller than the height of the rectangular block 372. The "U" shaped valley 374 is recessed into the rectangular block 372 at an angle substantially perpendicular to the plane of the top face of the rectangular block 372. The bottom of the "U" shaped valley 374 defines a raceway 86 for a fluid line.

Figure 16:
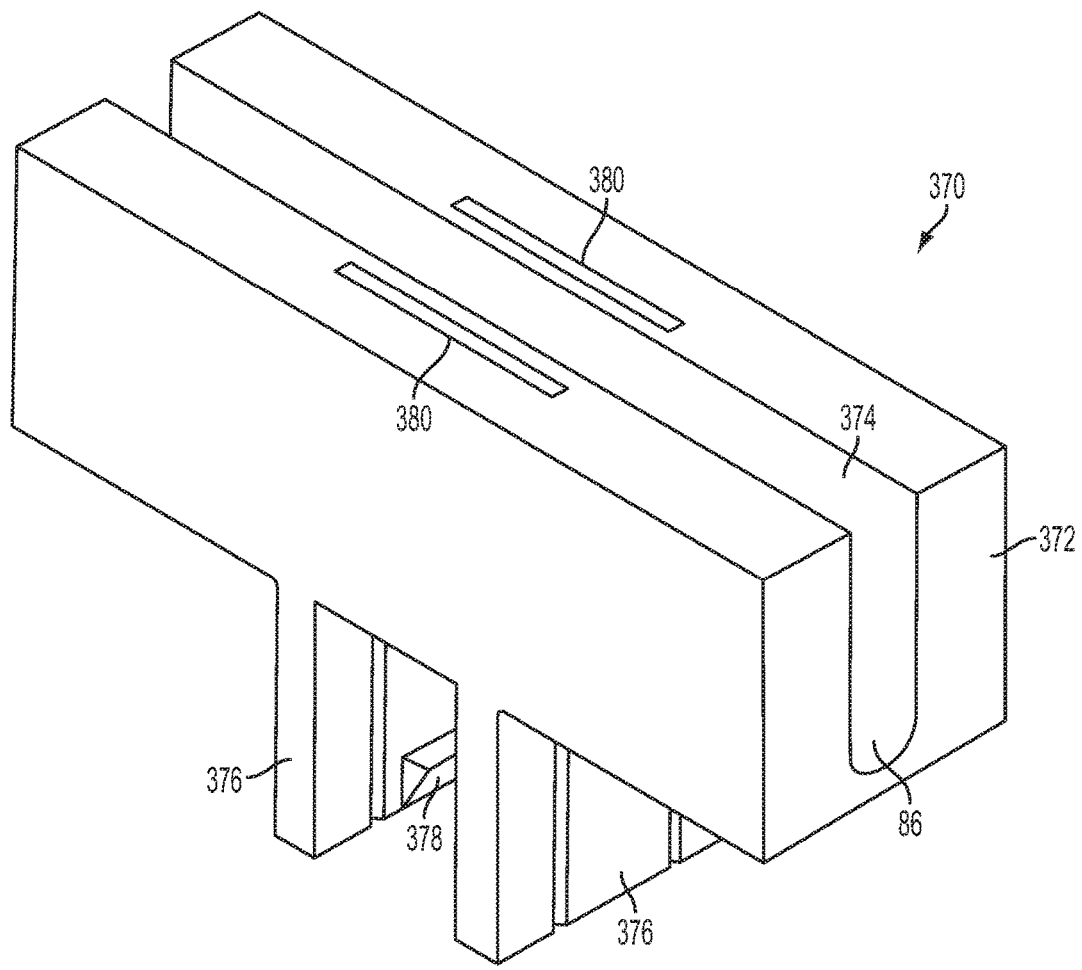
FIGS. 16-19 show an example of a housing for a split ring resonator component in accordance with an embodiment of the present disclosure.

Two leg-like members 376 may extend roughly perpendicularly from the bottom face of the rectangular block 372. The two leg-like members 376 in the example embodiment are oriented approximately perpendicularly to the longitudinal axis of the rectangular block 372. The two leg-like members 376 may be disposed symmetrically about the lateral centerline of the rectangular block 372 as is shown in FIG. 16. As in the example embodiment, snap fit features 378 may be included on each the two leg-like members 376 (only one is visible in FIG. 16). The snap fit features 378 may be disposed such that they extend from the center of the bottom edge of each of the two leg-like members 376. In the example embodiment, the snap fit features 378 extend from the edges most proximal to the lateral centerline of the rectangular block 372. The snap features 378 may allow energy couplers for the antennas of a split ring resonator component to interface with to be snapped into place on the housing 370. In some embodiments, the housing 370 may include snap fit features 378 to help to hold a bubble detection component (see FIG. 4) in place on the housing 370. In some embodiments, the snap fit features 378 may allow the housing 370 to be snap fit into a larger device.

Figure 26:
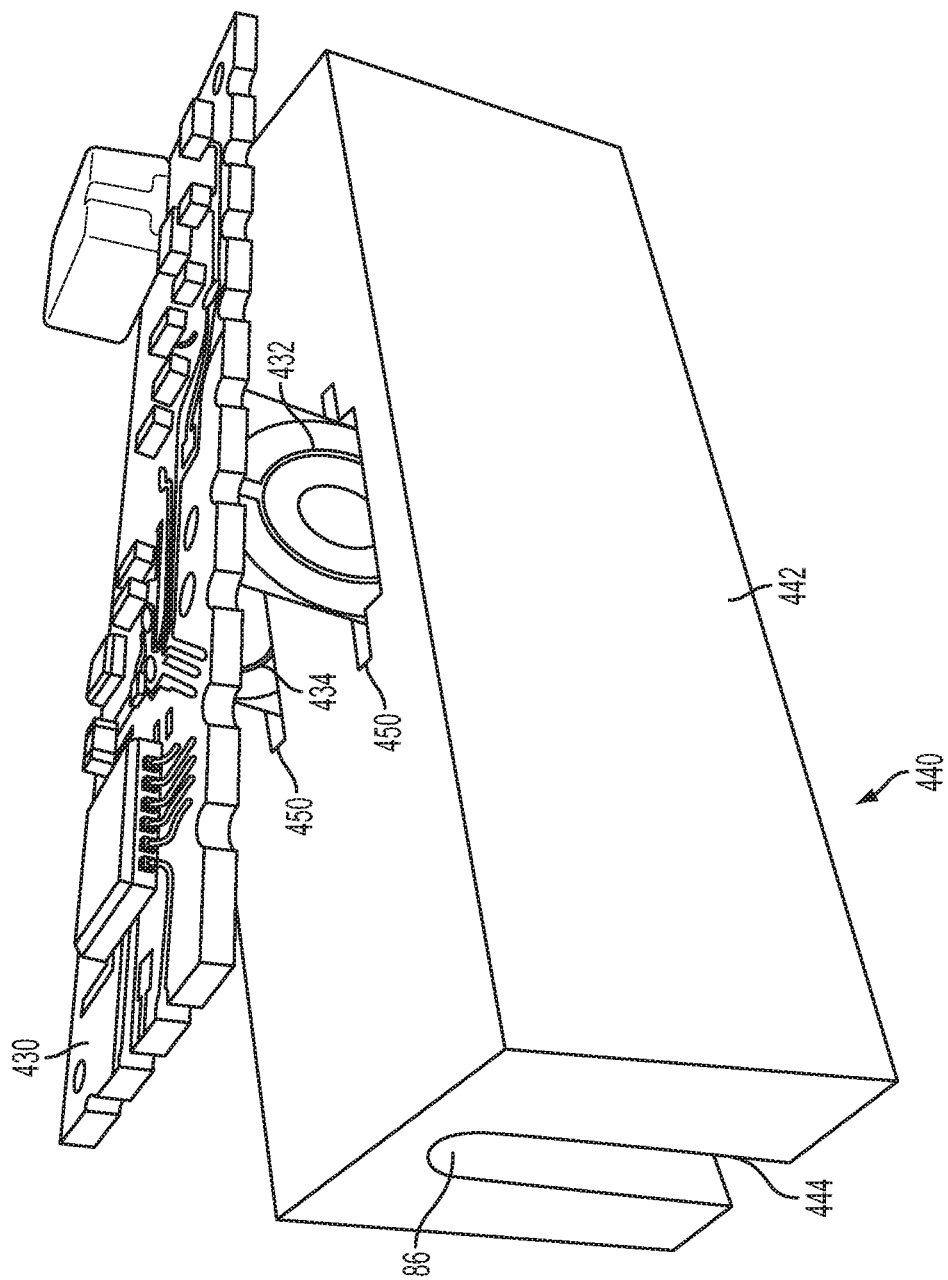
FIG. 26 shows an example PCB including two antennas being inserted into an example split ring resonator component housing in accordance with an embodiment of the present disclosure.

Some embodiments of the housing 370 may not include the two leg-like members 376 and snap fit features 378 (see FIG. 26).

Flanking the U-shaped valley 374 may be two antenna slits 380. As shown in the example embodiment, the two antenna slits 380 may extend all the way through the rectangular block 372 and continue all the way through the two leg-like members 376. The two antenna slits 380 may extend through the rectangular block 372 and the two leg-like members 376 at an angle substantially perpendicular to the top face of the rectangular block 372. Additionally, as shown in FIG. 16, the two antenna slits 380 may have a slit width which extends an equal distance longitudinally from each side of the lateral centerline of the rectangular block 372.

The housing 370 may be made from any number of suitable materials. In some embodiments, the housing 370 may be made from plastic, nylon, a polymer, etc. The housing 370 may include a shield which may be, for instance, a coating. In such embodiments the housing 370 may be coated with a conductive material, such as copper, another metal, etc. The coating may help to protect the SRR component from spurious signals. In some specific embodiments, the housing 370 may be approximately 1.500 inches long, 0.480 inches wide, and 0.930 inches in height (including the leg-like members 376).

Figure 17:
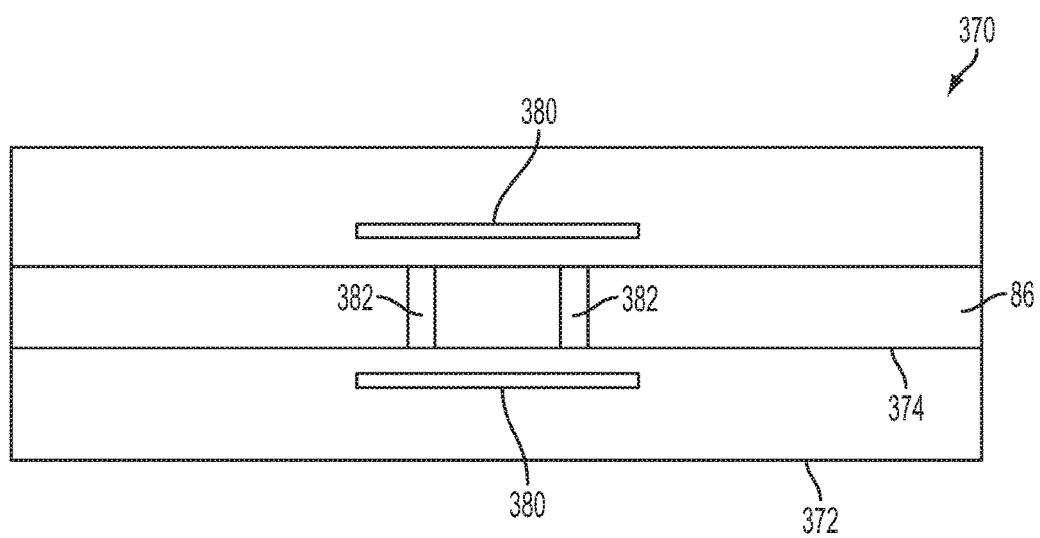

FIG. 17 shows a top view of the exemplary housing 370 depicted in FIG. 16. In FIG. 17, the top face of the rectangular block 372, U-shaped valley 374, raceway 86, and the antenna slits 380 are visible. The embodiment shown in FIG. 17 also includes two spacer members 382. The two spacer members 382 may project from the raceway 86 and up the walls of the U-shaped valley 374 toward the top face of the rectangular block 372. The two spacer members 382 are disposed perpendicular to the longitudinal axis of the housing 370 and are located between the two antenna slits 380.

When a fluid line (see FIG. 18) is in place in the housing 370, the two spacer members 382 may serve to ensure proper and consistent positioning of the fluid line in relation to the SRR component (see FIG. 4). In the example embodiment, the two spacer members 382 may position the fluid line such that it is substantially level with the antennas (see FIG. 5a or FIG. 5b) when the antennas are in place in the antenna slits 380. In some embodiments, the top face of the two spacer members 382 may be flat. In some embodiments, the two spacer members 382 may include a contour in their top faces to better and more securely locate a fluid line. In some embodiments, an SRR, such as any of those described herein, may also be supported by the two spacer members 382.

Figure 18:
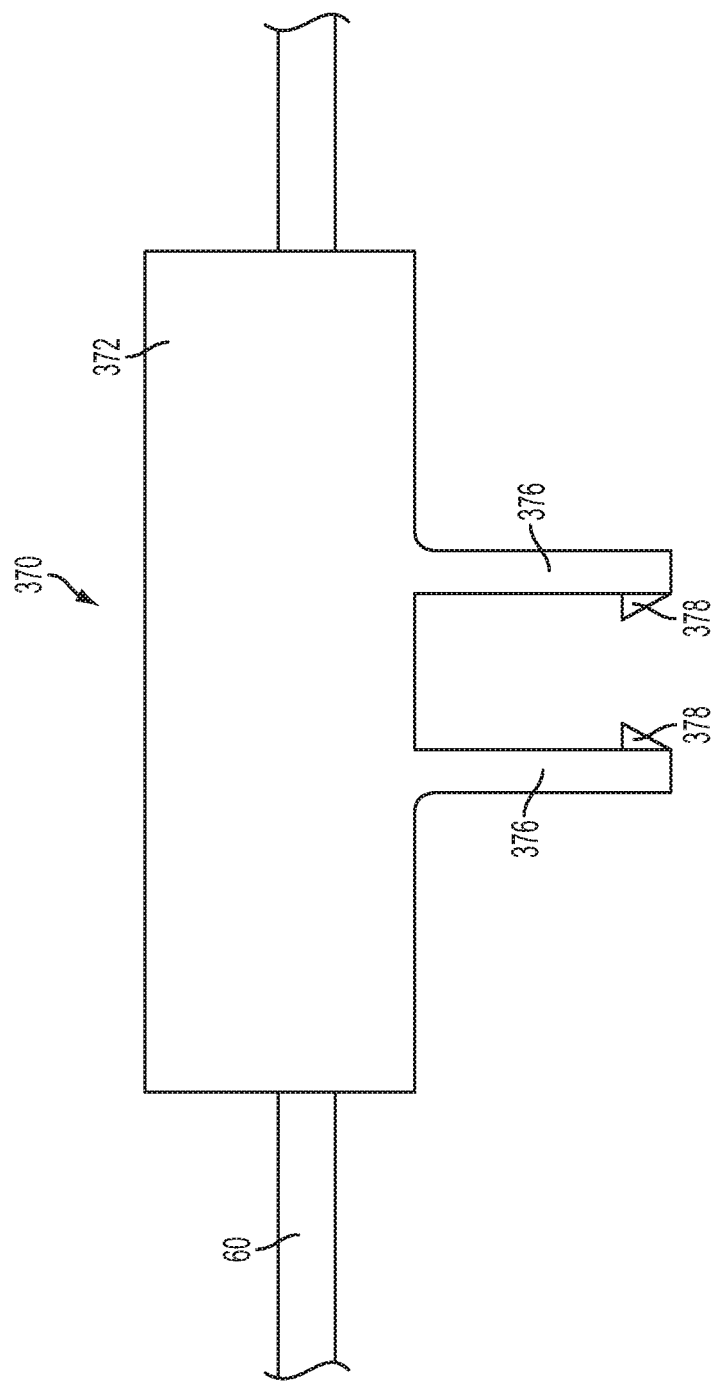

FIG. 18 depicts a side view of the example housing 370 shown in FIG. 16. As shown, the rectangular block 372, two leg-like members 376, and both of the snap fit features 378 are visible in FIG. 18. Additionally, a fluid line 60 is shown in place in the housing 370.

Figure 19:
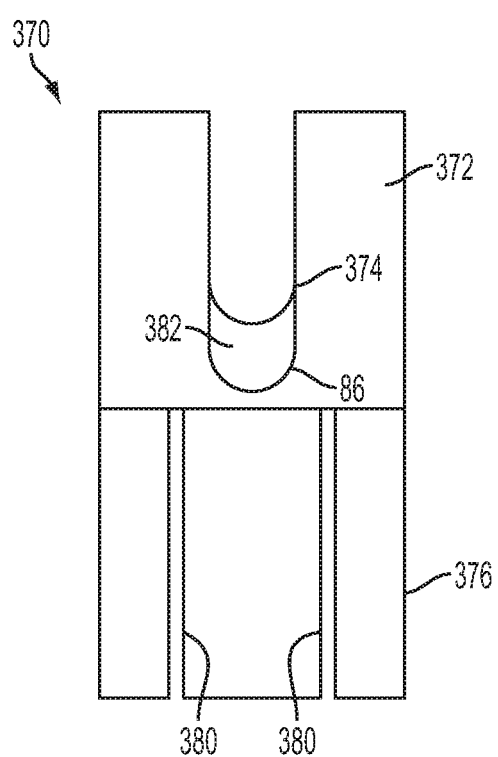

FIG. 19 depicts another side view of the example housing 370 shown in FIG. 16. The rectangular block 372, U-shaped valley 374, raceway 86, one of the leg-like members 376, the antenna slits 380, and one of the two spacer members 382 are visible in FIG. 19.

Figure 20:
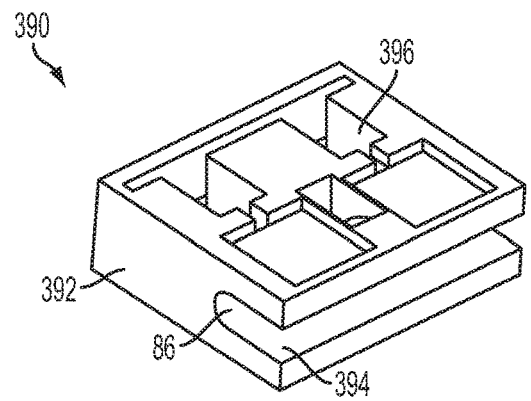
FIGS. 20 and 21 show an embodiment of another split ring resonator component housing in accordance with an embodiment of the present disclosure.
Figure 21:
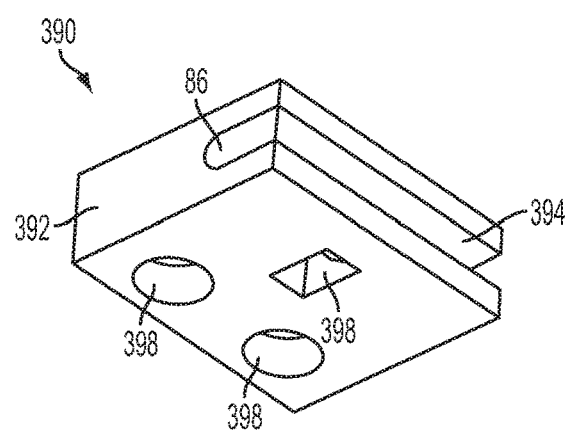
Figure 22:
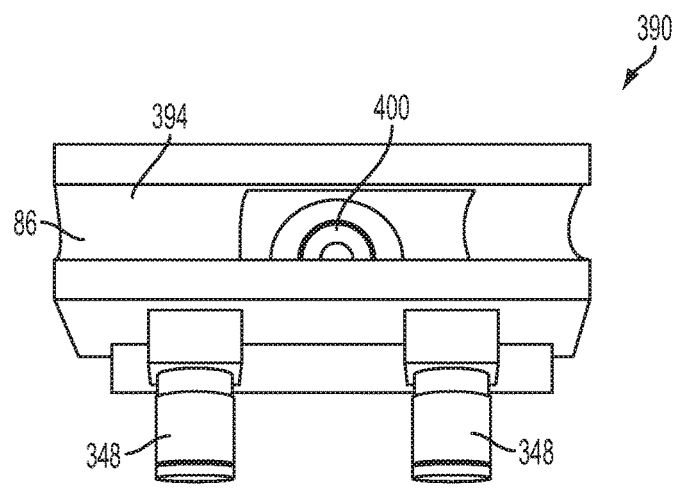
FIG. 22 shows an embodiment of the split ring resonator component housing of FIGS. 20 and 21 with an example split ring resonator, antennas, and energy couplers in place on the housing in accordance with an embodiment of the present disclosure.

Another example embodiment of a housing 390 is shown in FIGS. 20-22. A perspective view of this housing 390 is shown in FIG. 20. The housing 390 includes a block 392. The block 392 may be substantially rectangular. A valley 394 is recessed into a face of the block 392. The valley 394 may be "U" shaped. In the example embodiment, the valley 394 is recessed perpendicularly into a side of the block 392 roughly along the longitudinal centerline of the block 392. The valley 394 may be approximately 0.125 inches wide. In other embodiments, the valley 394 may be dimensioned in any suitable way. The bottom of the valley 394 may define a raceway 86 for a tube (not shown).

The block 392 may also include at least one housing depression. A first housing depression 396 is shown in FIG. 20. The first housing depression 396 is dimensioned such that one or a number of components of a system for detecting a bubble (see FIG. 4) may be seated in the housing 390. The first housing depression 396 may be recessed into a face of the housing 390. In the example embodiment, the first housing depression 396 is recessed into the housing 390 at an angle perpendicular to the top face (relative to FIG. 20) of the housing 390. Certain parts of the first housing depression 396 may be recessed deeper into the housing 390 than others.

FIG. 21 shows another perspective view of the housing 390. The block 392, valley 394, and raceway 86 are visible. Also visible are a number of additional housing depressions 398. The additional housing depressions 398 may be dimensioned such that one or a number of components of a system for detecting a bubble (see FIG. 4) may be seated in the housing 390.

FIG. 22 depicts an example top view of the housing 390 with a number of components in place in and on the housing 390. As shown, an SRR 400 is placed into the valley 394 and contoured such that it conforms to the shape of the raceway 86. Two energy couplers 348 are also shown partially housed within the first housing depression 396 (best shown in FIG. 20). The energy couplers 348 transmit and receive energy respectively to and from a transmitting antenna and receiving antenna which are not visible in FIG. 22. The transmitting antenna and the receiving antenna may be housed at least partially within the first housing depression 396.

Figure 23:
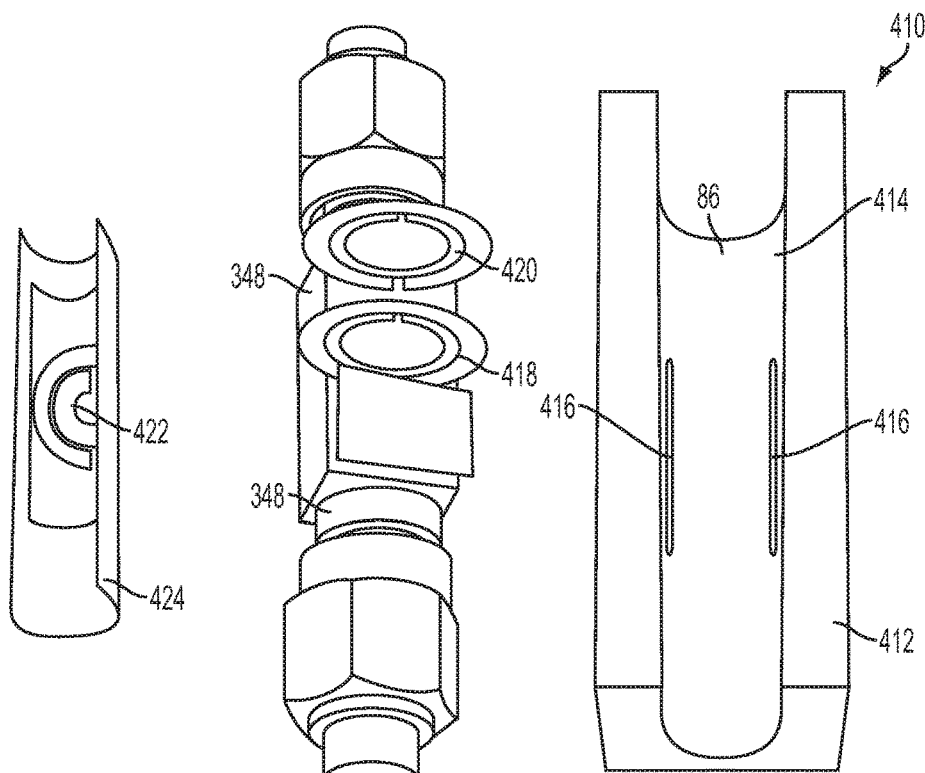
FIG. 23 shows an unassembled example split ring resonator component having a split ring resonator component housing in accordance with an embodiment of the present disclosure.
Figure 24:
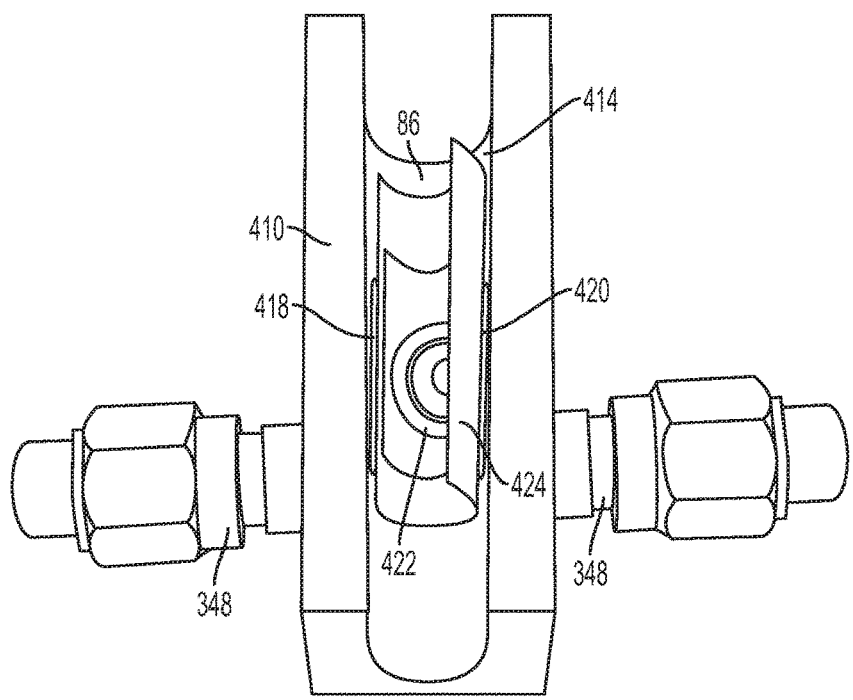
FIG. 24 shows an assembled view of the example split ring resonator component having the split ring resonator component housing of FIG. 23 in accordance with an embodiment of the present disclosure.

FIG. 23 shows an unassembled example split ring resonator component and split ring resonator component housing 412, and FIG. 24 shows an assembled view of the example split ring resonator component and split ring resonator component housing in accordance with an embodiment of the present disclosure. Referring to FIG. 23, the housing 410 includes a block 412. A valley 414 is recessed into a face of the block 412. A raceway is defined at the bottom of the valley 414. Two antenna slits 416 are also cut through the block 412 and flank each side of the raceway 86.

A number of components of the system for detecting a bubble are also shown in FIG. 23. A transmitting antenna 418 and a receiving antenna 420 are shown attached to two energy couplers 348. The transmitting antenna 418 and the receiving antenna 420 are each loop antennas. Specifically, they each include two concentric conductive rings which include splits and appear substantially identical to some of the SRR embodiments disclosed herein. By attaching an SRR to a coaxial cable, energy coupler, etc., the SRR may be utilized as a loop antenna. Additionally, an SRR 422 is shown in place in an SRR housing 424 in FIG. 23. Alternate embodiments may not include the SRR housing 410.

In FIG. 24, the components shown in FIG. 23 are in place in the housing 410. As shown, the SRR 422 and SRR housing 424 are in place in the raceway 86 of the valley 414. In some embodiments, the SRR housing 424 may be fixedly coupled to a particular spot on the raceway 86 to ensure optimal energy transmission. The transmitting antenna 418 and the receiving antenna 420 are in place in the antenna slits 416 (best shown in FIG. 23) of the housing 410. The housing 410 is configured such that it may sit atop the energy couplers 348.

When in use, a tube (not shown) would be placed in the raceway 86. The SRR housing 424 may wrap around the tube or a portion of the tube to hold the tube in place. Energy may be transmitted from the transmitting antenna 418 to the receiving antenna 420 and through the SRR 422. A parameter of the energy may then be measured to determine, for example, if an air bubble exists in the tube.

In some embodiments, a choke may also be included to block noise from being transmitted by a transmitting antenna such as the transmitting antenna 418. In various embodiments, the choke may be an RF choke, or specifically a ferrite bead choke.

Figure 25:
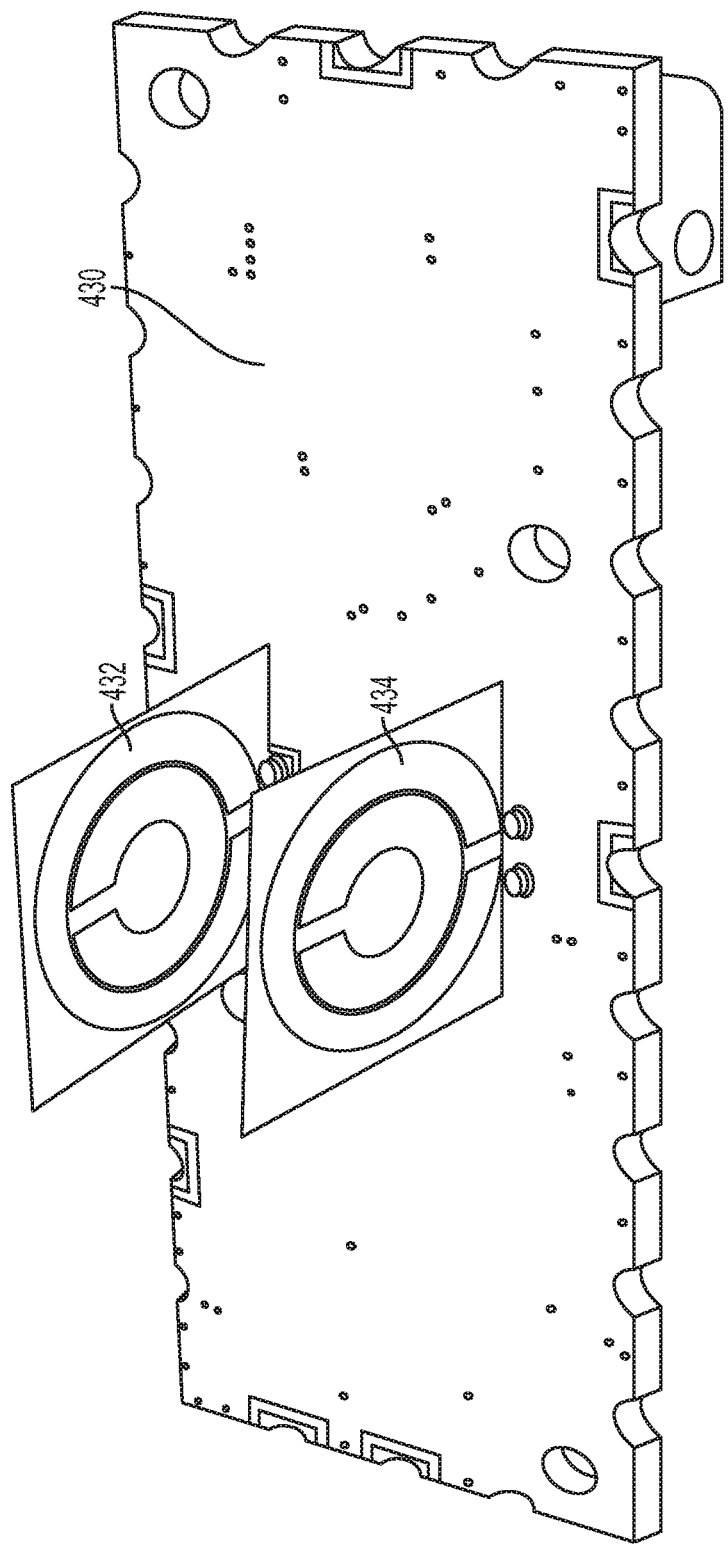
FIG. 25 shows an example PCB including two antennas in accordance with an embodiment of the present disclosure.

Referring now to FIG. 25, a PCB 430 and two antennas 432, 434 are shown. The two antennas 432, 434 may be operatively coupled to the PCB 430. The PCB 430 may be designed such that it may cause one of the antennas 432, 434 to transmit at any suitable frequency or number of different frequencies. The PCB 430 may also include, for example, circuitry for the bubble detection component 62 shown in FIG. 4.

FIG. 26 depicts an example embodiment of an example PCB 430 with antennas 432, 434 being placed into an example housing 440. The housing 440 shown is similar to that shown in FIGS. 16-19. The housing 440 in FIG. 26, includes a rectangular block 442 with a U-shaped valley 444, a raceway 86, and antenna slits 450. The housing 440, however, does not include the leg-like members 346 and snap fit features 348 shown in FIGS. 16-19. Instead the PCB 430 may be coupled directly to a face of the rectangular block 442. As shown, the antennas 432, 434 may be slid into their respective antenna slits 450. After the antennas 432, 434 are completely within their respective antenna slits 450, the PCB 430 may be coupled to the rectangular block 442 via any suitable fastener or combination of fasteners, such as for example, screws, bolts, glue, adhesive, etc.

Figure 27:
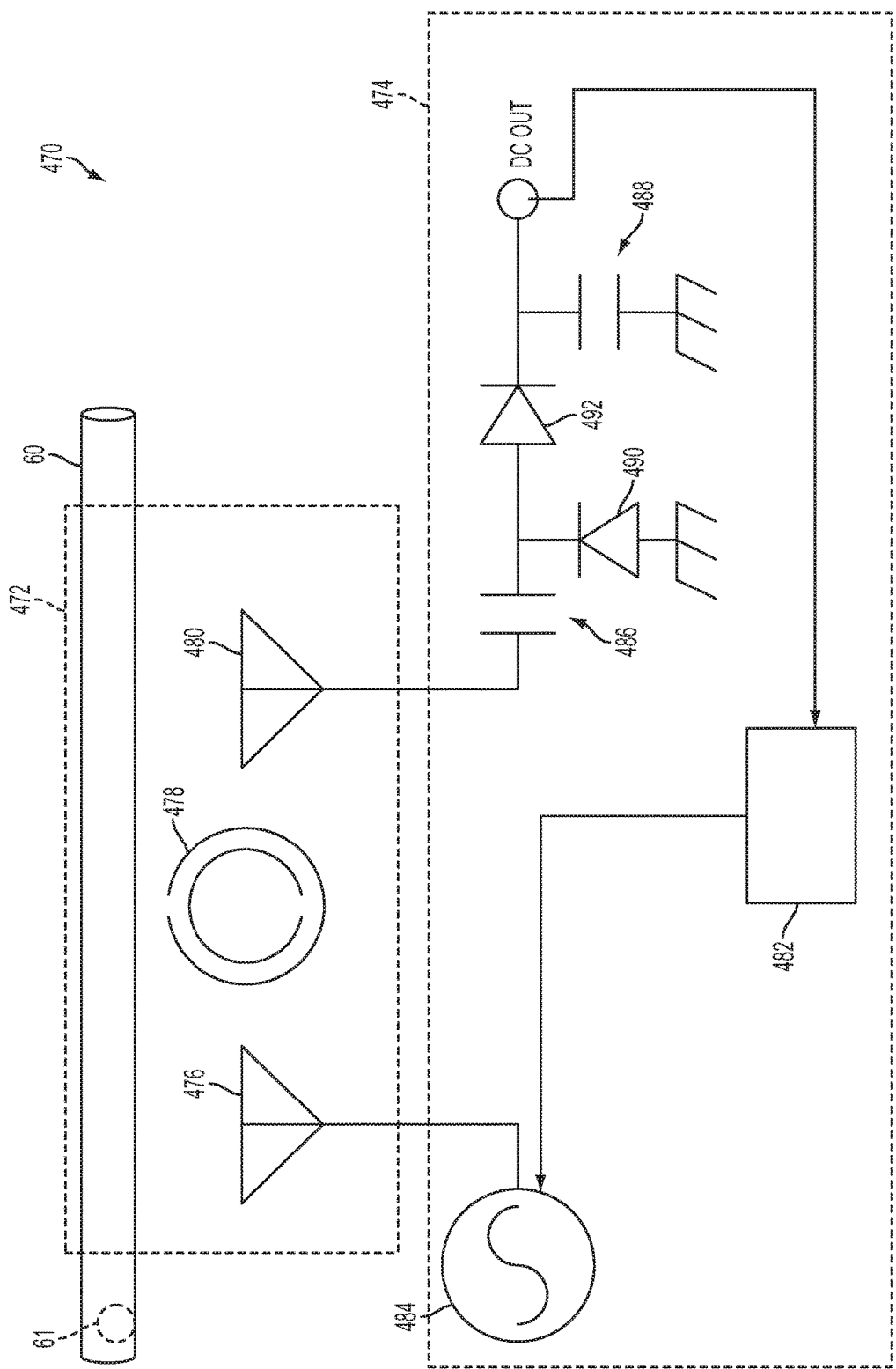
FIG. 27 shows an example schematic diagram of a system for detecting a bubble within a fluid line in accordance with an embodiment of the present disclosure.

FIG. 27 shows a schematic 470 illustration of an embodiment of the system 58 of FIG. 4 in accordance with an embodiment of the present disclosure. The schematic 470 includes a split-ring resonator component 472 and a bubble detection component 474. The bubble detection component 474 is coupled to the split-ring resonator component 472 to measure or estimate one or more parameters of the energy transmitted through the split-ring resonator component 472. The bubble detection component 474 may use the one or more parameters to detect the existence of a condition of interest, e.g., the presence of a bubble 61 within a tube 60. In other embodiments, the bubble detection component 474 may, for example, detect the state of a raceway 86 (see, for example, FIG. 16) adjacent to the split ring resonator component 472 using the one or more parameters.

The split-ring resonator component 472 includes a transmitting antenna 476, an SRR 478, and a receiving antenna 480. The transmitting antenna 476 and the receiving antenna 480 may be loop antennas. In additional embodiments, the transmitting antenna 476 and the receiving antenna 480 may be any other suitable type of antenna, such as monopole antennas and/or dipole antennas. The SRR 478 may be one of the example SRRs shown and described in reference to FIGS. 6-14. The SRR 478 may have a resonance frequency of about 4.3 GHz in some embodiments. A tube 60 may be positioned near the SRR 478, near a gap of the SRR 478, or through the center void of the SRR 478 such that one or more of the conductors of the SRR 478 surround the tube 60. In some embodiments of the present disclosure, multiple SRRs (see FIG. 28) may be used.

The bubble detection component 474 may include a processor 482 coupled to a Voltage Controlled Oscillator (abbreviated herein often as VCO) 484 that generates microwave energy as in shown in FIG. 27. The processor 482 may select one or more frequencies for generation by the VCO 484 which will then be transmitted via the transmitting antenna 476. In some specific embodiments, the VCO 484 may have a range of 3.9-4.4 GHz. The processor 482 includes a digital-to-analog converter (not explicitly shown) to apply the voltage to the VCO 484. The voltage applied to the VCO 484 is converted to an electromagnetic signal such as microwave energy in accordance with a predetermined formula, e.g., the voltage supplied from the processor 482 to the VCO 484 is converted to a frequency in accordance with a predetermined specification of the VCO 484. Appropriate buffer circuitry, amplifiers, and/or isolators may be used between the processor 482 and the VCO 484 and/or between the VCO 484 and the transmitting antenna 476, in some embodiments.

As shown in FIG. 27, the bubble detection component 474 receives a signal from a receiving antenna 480 which is electrically coupled to capacitors 486 and 488, and to diodes 490 and 492 to rectify the signal. The diodes 490 and 492 may be a Schottky Diode pair such as a Microwave Schottky Mixer Diodes circuit having the part number HSMS-8202-TR1, manufactured by Avago Technologies Inc. of 350 West Trimble Road, Building 90, San Jose, Calif., United States, 95131. In the example embodiment, the DC out signal (i.e., the rectified signal) is fed into the processor 482. The processor 482 may include an analog-to-digital converter (not explicitly shown) to determine the DC value of the signal from the diode 492 and capacitor 488. The processor 482 may use the DC value to measure one or more parameters of the SRR 478. In some embodiments, the processor 482 may be in communication with additional circuitry coupled to the receiving antenna 480 to measure or estimate one or more parameters associated with the SRR 478, e.g., the phase angle, resonance frequency, etc.

In some embodiments, the processor 482 may instruct the VCO 484 to perform a frequency sweep (e.g., linearly or non-linearly) to output one or more frequencies. The processor 482 may receive a DC signal from the capacitor 488 which may then used to determine one or more parameters, e.g., a bandpass response, frequency response, phase response, etc.

The processor 482 may also receive additional feedback information; for example, the processor 482 may receive feedback about the signal applied to the antenna 486 from the VCO 484, such as a measured frequency, a measured amplitude, a variance, a power, etc. In some embodiments, this feedback may be compared to the signal from the capacitor 488 to determine a condition of interest.

Figure 28:
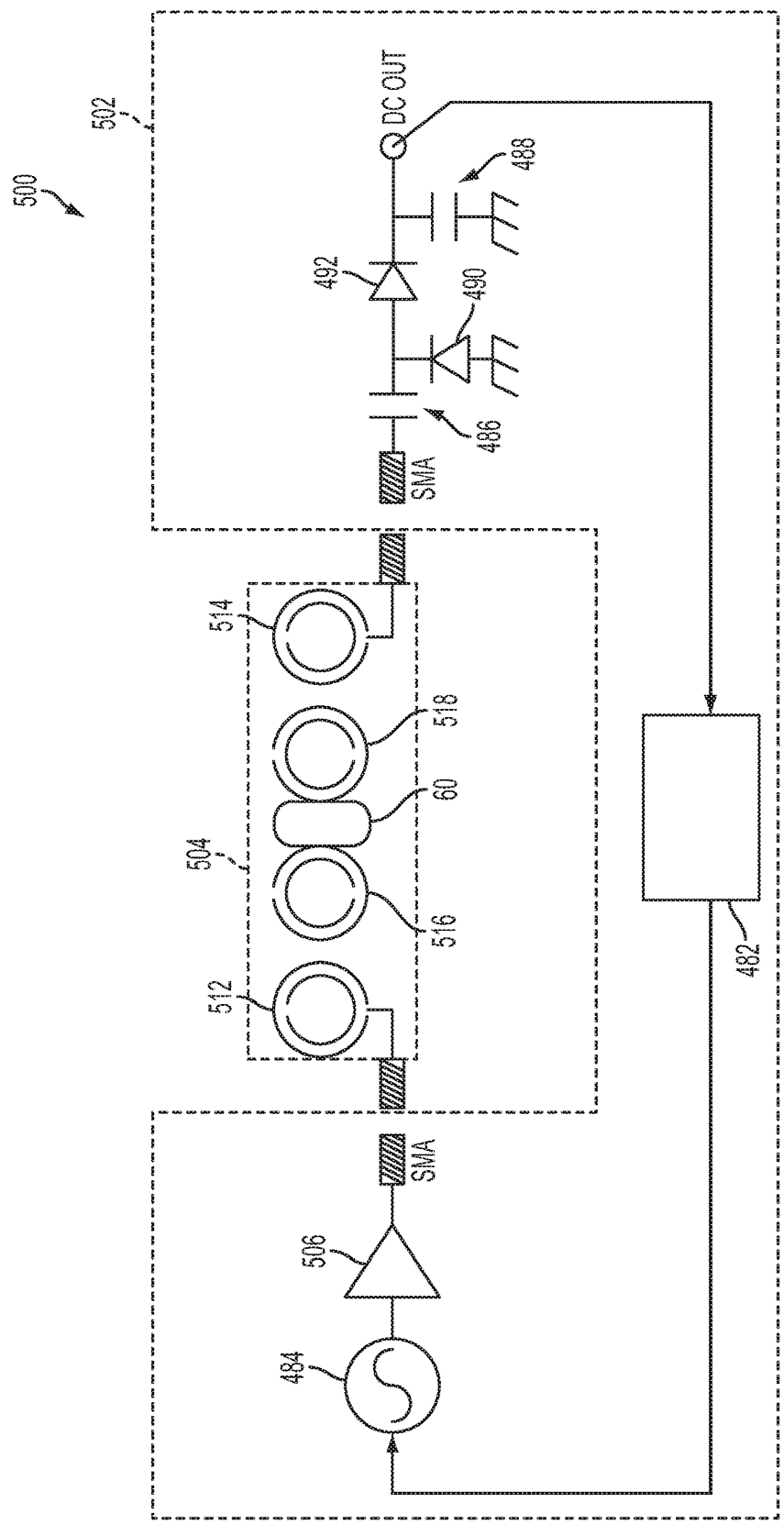
FIG. 28 shows another example schematic diagram of a system for detecting a bubble within a fluid line in accordance with an embodiment of the present disclosure.

FIG. 28 shows a diagram of a system 500 for detecting a bubble within a fluid line 60 in accordance with an embodiment of the present disclosure. The system 500 includes a bubble detection component 502 and an SRR component 504.

The bubble detection component 502 includes a processor 482 coupled to a VCO 484. The VCO 484 may be coupled to an amplifier 506 as shown in FIG. 28. The amplifier 506 applies the amplified microwave energy to the transmitting antenna 512 of the SRR component 504 via SMA connectors. The processor 482 may select one or more frequencies to be transmitted via the VCO 484. The selected one or more frequencies may then pass through the amplifier 506 and be transmitted by the transmitting antenna 512.

In the example embodiment shown in FIG. 28, the bubble detection component 502 receives the transmitted microwave energy through a receiving antenna 514 of the SRR component 504. The bubble detection component 502 may rectify the signal using the capacitors 486 and 488, and the diodes 490 and 492. The rectified signal may then be received by the processor 482. The processor 482 may use the received signal to measure one or more parameters corresponding to the SRRs 516 and 518 to detect a condition of interest, for example, the presence of a bubble within the tube 60.

As shown in FIG. 28, the bubble detection component 504 may include two SRRs 516 and 518. The two SRRs 516, 518 are positioned next to the tube 60. The two SRRs 516, 518 may have a resonant frequency of 4.3 GHz in some specific embodiments. The SRR component 504 also includes a transmitting and a receiving loop antenna 512 and 514. The transmitting loop antenna 512 and receiving loop antenna 514 may specifically be 8 GHz loop antennas each including an inner conductor having a gap and outer conductor having a gap.

As in FIG. 27, the processor 482 of FIG. 28 may instruct the VCO 484 to perform a frequency sweep (e.g., linearly or non-linearly) over one or more frequencies. In some embodiments, the processor 484 may receive various feedback about the signal applied to the antenna 512. In such embodiments, this may help the processor 482 to determine whether or not one or more conditions of interest exist.

Figure 29:
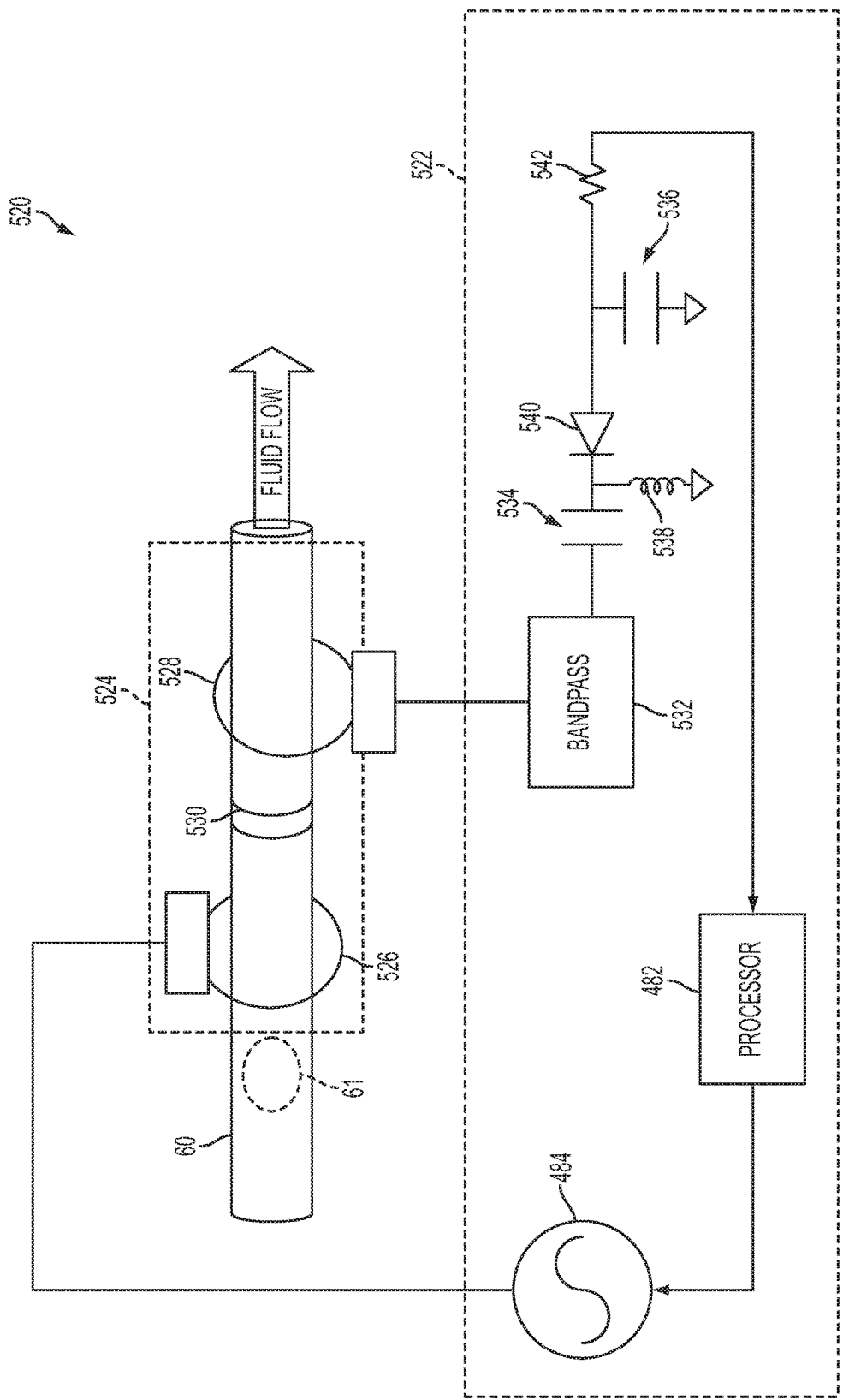
FIG. 29 shows yet another example schematic diagram of a system for detecting a bubble within a fluid line in accordance with an embodiment of the present disclosure.

FIG. 29 shows a diagram of a system 520 for detecting a bubble 61 within a fluid line 60 in accordance with an embodiment of the present disclosure. The system 520 includes a bubble detection component 522 and a split ring resonator component 524.

The split ring resonator component 524 includes a transmitting loop antenna 526 and a receiving loop antenna 528. The transmitting loop antenna 526 and the receiving loop antenna 528 are disposed such that the fluid line 60 is encircled by each of the transmitting loop antenna 526 and the receiving loop antenna 528. The split ring resonator component 524 in FIG. 29 also includes a single SRR 530. The fluid line 60 extends through the center of the SRR 530. The SRR 530 is disposed between the transmitting loop antenna 526 and the receiving loop antenna 528. As in the embodiments in FIGS. 27 and 28, the system 520 includes a processor 482 and a VCO 484. The processor 482 may select one or more frequencies to be generated by the VCO 484 and transmitted by the transmitting loop antenna 526.

The bubble detection component 522 may be operatively coupled to the transmitting loop antenna 526 and the receiving loop antenna 528 which surround the fluid line 60 in FIG. 29. As mentioned above, the bubble detection component 522 in FIG. 29 includes a processor 482 coupled to a VCO 484 to transmit one or more microwave energy frequencies via the transmitting loop antenna 526. The bubble detection component 522 receives the microwave energy via a bandpass 532. The bandpass 532 may filter out frequencies other than the transmitting frequency of the transmitting loop antenna 526. The processor 482 may be coupled to the bandpass 532 to tune the frequency of the bandpass 532.

In the example embodiment in FIG. 29, the bandpass 532 is coupled to capacitors 534 and 536, an inductor 538, a diode 540, and a resistor 542. The circuit components 534, 536, 538, 540, and 542 rectify the signal which is sent to an analog-to-digital converter (not explicitly shown) of the processor 482.

The signal received by the processor 482 from the analog-to-digital converter (not explicitly shown) may be used to measure or estimate one or more parameters of the SRR 530. The measured or estimated one or more parameters of the SRR 530 may then be used to determine if one or more conditions of interest, for instance, the presence of an air bubble 61 in a tube 60 exist.

As mentioned above in reference to other embodiments, the processor 482 may also receive various feedback regarding the signal applied to the transmitting loop antenna 526. The processor 482 may, in some embodiments, instruct the VCO 484 to sweep one or more frequencies. In such embodiments, the processor 482 may then, for example, determine a frequency response of the SRR 530 over the one or more frequencies.

Figure 30:
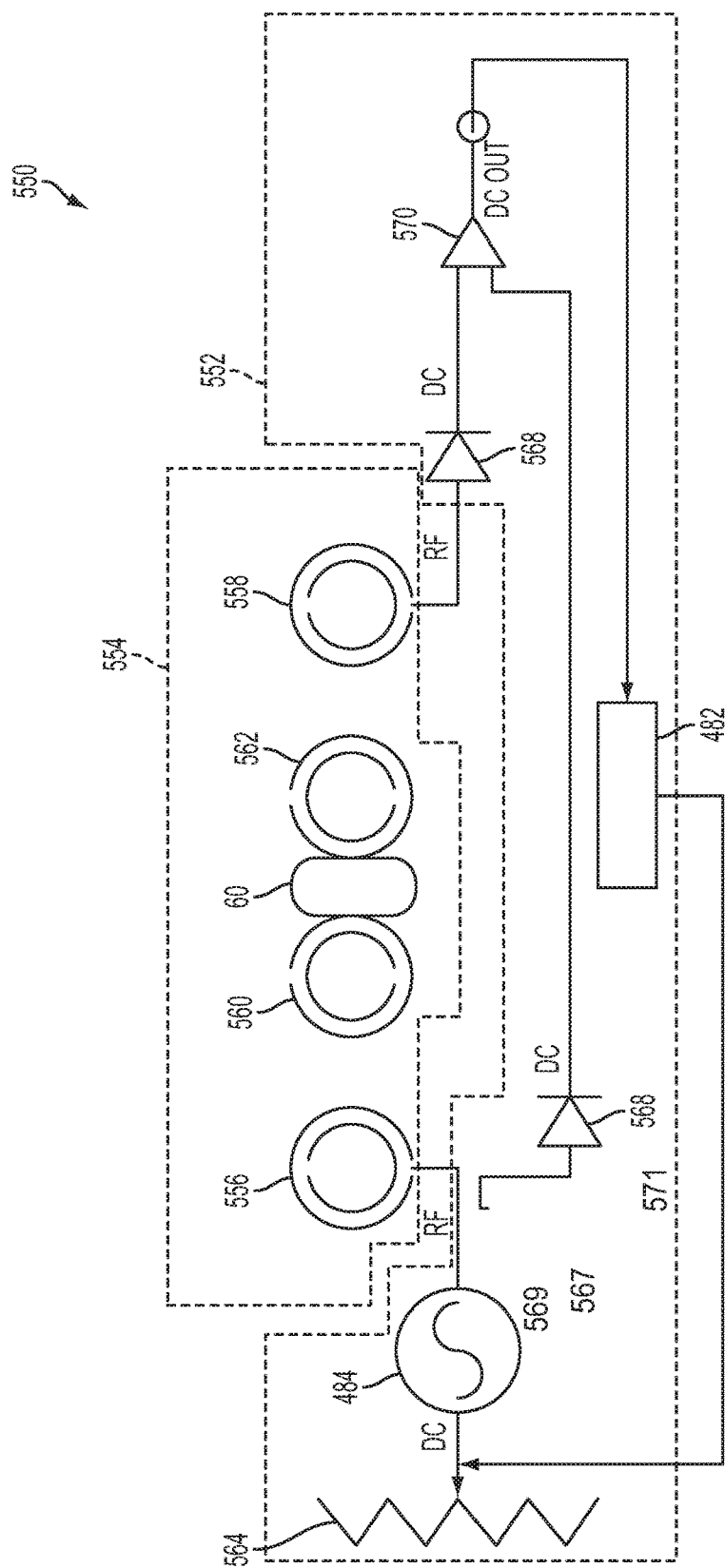
FIG. 30 shows another example schematic diagram of a system for detecting a bubble within a fluid line in accordance with an embodiment of the present disclosure.

FIG. 30 shows a diagram of a system 550 for detecting a bubble within a fluid line 60 in accordance with an embodiment of the present disclosure. The system 550 includes circuitry 552 which may perform the function of a bubble detection component. The system 550 additionally includes a split ring resonator component 554. The split ring resonator component 554 may include or be included in a housing, such as one of the housing embodiments depicted in FIGS. 16-19.

The split ring resonator component 554 in FIG. 30 includes a transmitting loop antenna 556 and a receiving loop antenna 558. As shown the, transmitting loop antenna 556 and receiving loop antenna 558 each include two concentric conductive rings with a split. The split ring resonator component 554 in FIG. 30 includes two SRRs 560, 562. The SRRs 560, 562 may, for example, be any of the SRR embodiments described herein (e.g., FIGS. 6-14). The SRRs 560, 562 depicted are similar to the SRR 230 shown in FIG. 9.

The circuitry 552 includes a processor 482. The processor 482 may be coupled to a potentiometer 564. The processor 482 selects one or more frequencies for the VCO 484 and controls operation of the VCO 484 via the potentiometer 564. The processor 482 may, for example, control the potentiometer 564 to create a voltage ramp. This may be done in embodiments where it is desirable to measure some parameters, such as a frequency response or a phase response.

The VCO 484 in FIG. 30 is coupled to the transmitting loop antenna 556 and an incident detector 567 (e.g. a microwave coupler 569 and a diode 571). The circuitry 552 receives the microwave energy via a receiving loop antenna 558. The receiving loop antenna 558 is coupled to a diode 568. The signals received from the diodes 571 and 568 are compared by a difference amplifier 570. The output signal of the difference amplifier 570 is then fed into the processor 482. The processor 482 measures or estimates one or more parameters corresponding to the SRRs 560 and 562 in order to detect a condition of interest, e.g. an air bubble in the tube 60.

Figure 31:
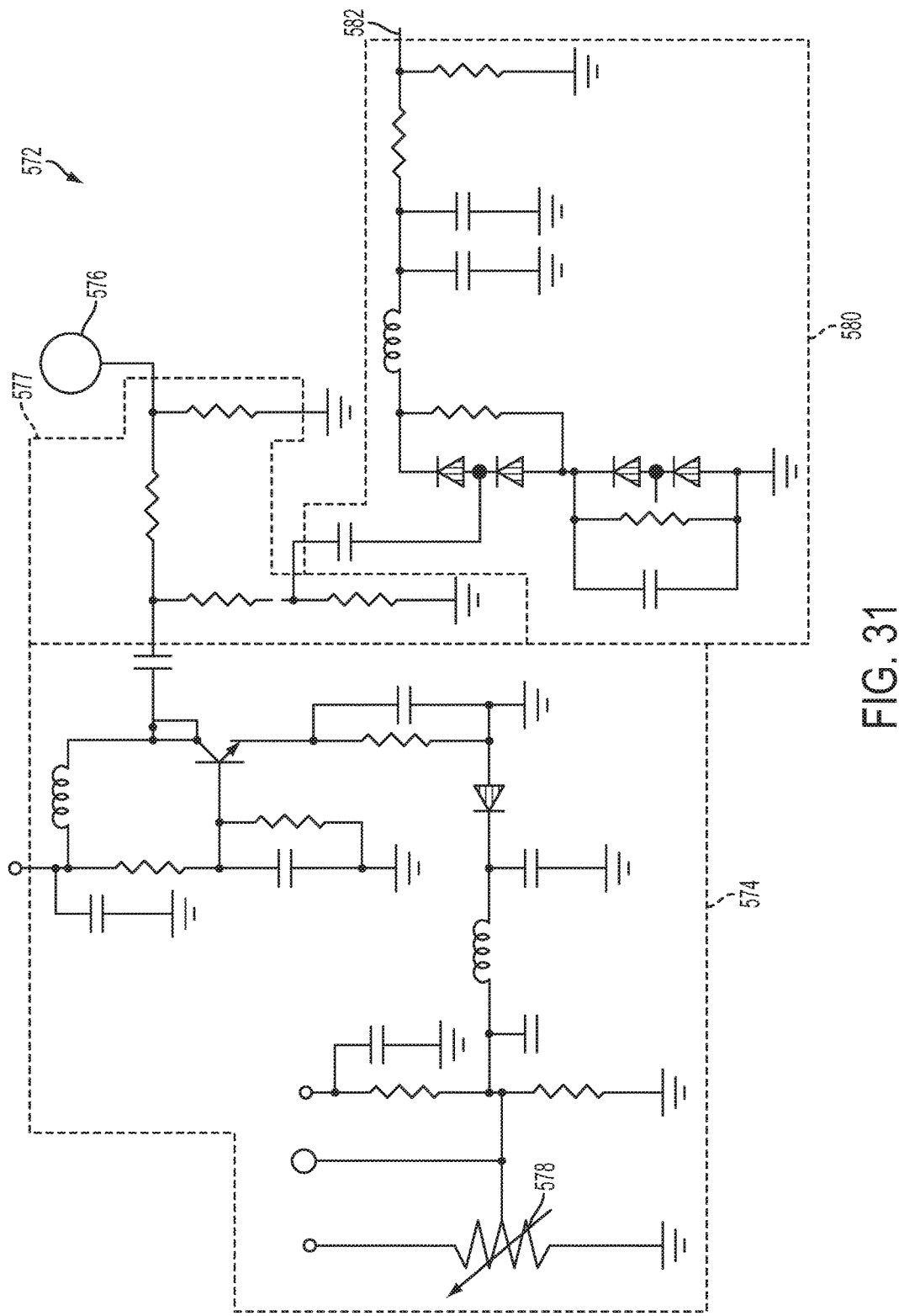
FIGS. 31-35 show a specific detailed example of the system of FIG. 34 in accordance with an embodiment of the present disclosure.
Figure 32:
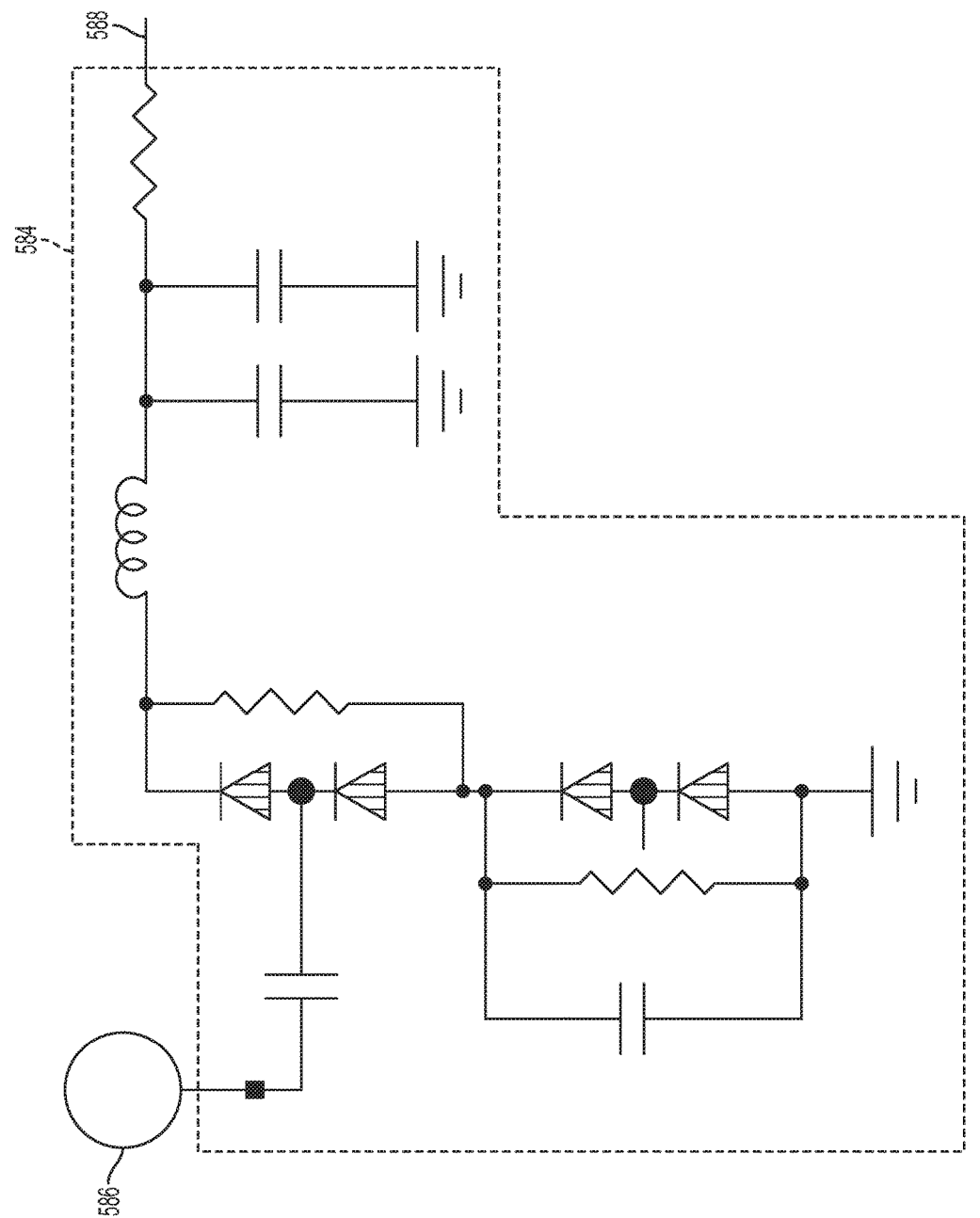
Figure 33:
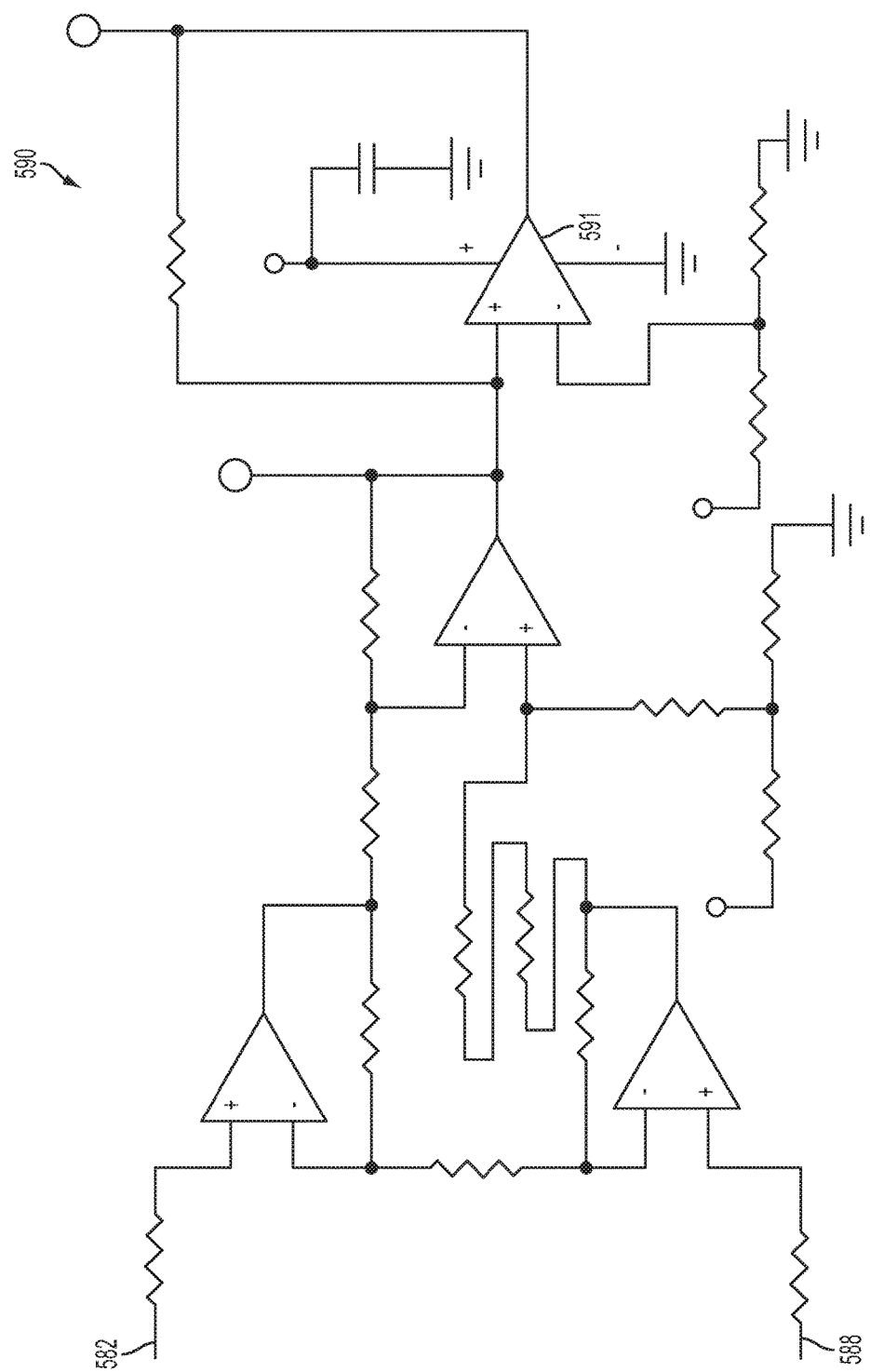

FIGS. 31-33 show a detailed specific example embodiment of a bubble detector circuit similar to that shown in FIG. 30. FIG. 31 shows a circuit 572 for use in a bubble detector including a voltage controlled oscillator component 574 coupled to a transmitting antenna 576 in accordance with an embodiment of the present disclosure. A processor (e.g., the processor 482 of FIG. 30) is coupled to a potentiometer 578 may control the frequency by selectively varying the position of the wiper on the resistive element of the potentiometer 578. In some embodiments, the position may instead be manually manipulated or set. The VCO component 574 may transmit a signal via a transmitting antenna 576. As in the example embodiment, the VCO 574 and the transmitting antenna 576 may be separated by an isolation attenuator 577. The circuit also includes a rectifier 580. The output of the rectifier 580 is a power detected voltage out 582.

FIG. 32 shows another circuit 584 coupled to a receiving antenna 586 for use in a bubble detector in accordance with an embodiment of the present disclosure. The receiving antenna 586 receives the signal from the transmitting antenna 576 in FIG. 31. An SRR (not shown) may be placed between the receiving antenna 586 and the transmitting antenna 576 (see FIG. 31). In such embodiments the SRR may be placed in close proximity to a tube. The circuit 584 serves as a rectifier for the signal received by the receiving antenna 586 and may have the same layout as the rectifier 580 shown in FIG. 31. The circuit 584 outputs a detect voltage out 588. The detect voltage out 588 will be dependent upon a number of features such as the state of a tube near the SRR.

FIG. 33 shows a difference amplifier circuit 590 for use in a bubble detector in accordance with an embodiment of the present disclosure. The difference amplifier circuit 590 receives the output 582 and 588 respectively from the rectifier 580 of FIG. 31 and the circuit 584 of FIG. 32. The difference amplifier circuit 590 amplifies the difference between the two received outputs 582 and 588. The amplified signal may then be passed to a processor (e.g., the processor 482 of FIG. 30). The processor may utilize this signal to determine if a condition of interest exists. The condition of interest, in some embodiments, may be related to the state of a tube.

In some embodiments, such as the embodiment shown in FIG. 33, a threshold detector 591 may also be included in the circuit 590. The threshold detector 591 may be included such that it may trigger an alarm if the voltage applied to the threshold detector 591 strays from an expected value. In some embodiments, the alarm may be triggered if the voltage deviates outside of a predefined threshold. In some additional embodiments, the threshold detector 591 may be configured to trigger an alarm if the output voltage crosses over a predefined threshold.

In other embodiments, the circuit 590 may be modified such that a window comparator is used in place of the threshold detector 591. In such embodiments, an alarm may be triggered if the voltage deviates out of a predefined window. In some embodiments including a window comparator, an alarm may be triggered if the output voltage enters a predefined window.

The alarm may be any of a variety of alarms. For example, the alarm may be a light or a number of lights which are illuminated in response to an alarm state. In some embodiments, the alarm may be an audible noise emitted from a speaker. In other embodiments, the alarm state may turn on a vibratory motor to produce vibrations. In some embodiments, a message declaring the alarm, e.g. a text message, may be displayed on the GUI of a larger device. Any other suitable alarm may also be used. In some embodiments, multiple alarms may be triggered in the alarm state, for example, a light and audible noise may be produced.

Figure 34:
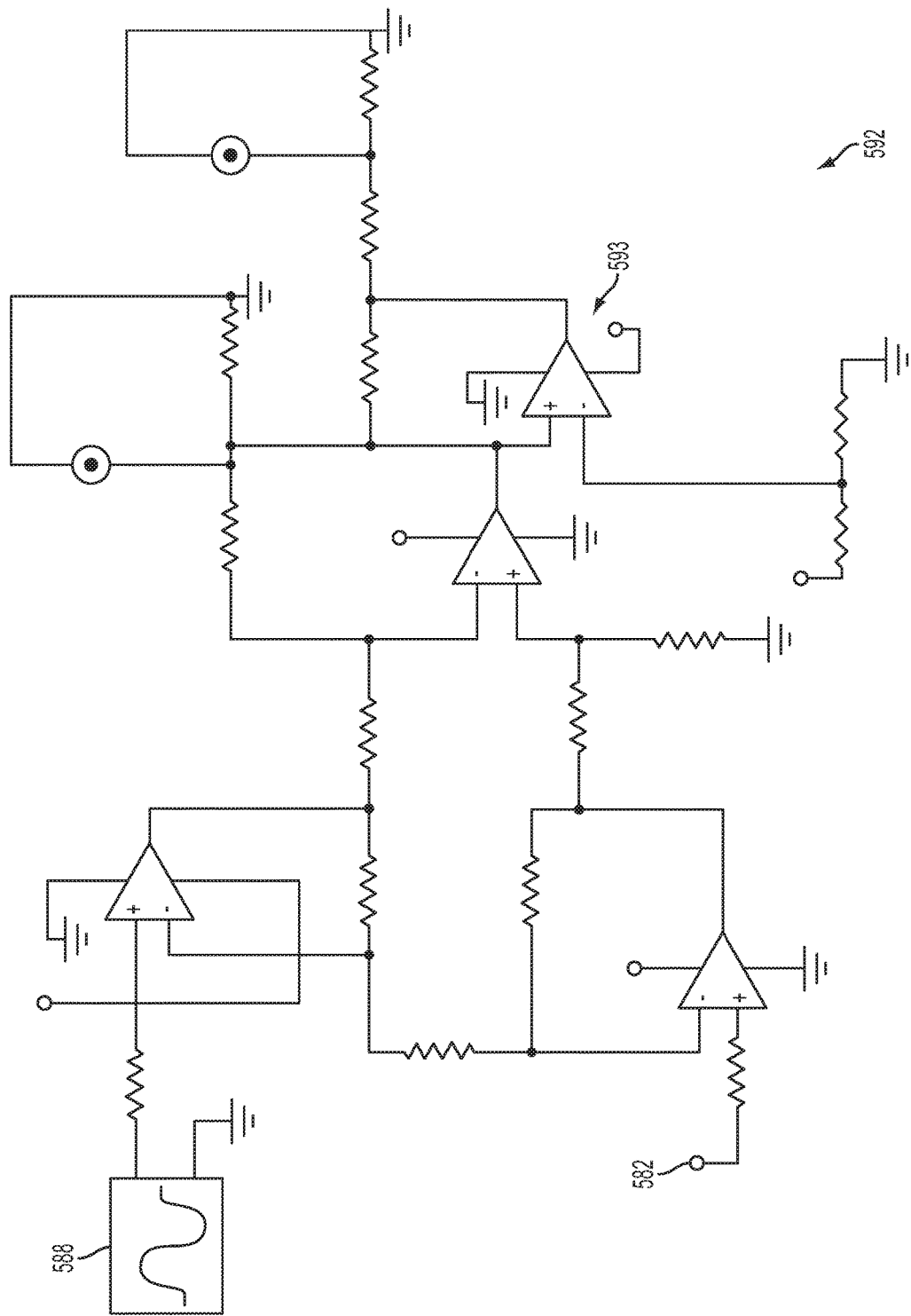

FIG. 34 shows an amplifier circuit 592 similar to the circuit 590 shown in FIG. 33. The difference amplifier circuit 592 receives the outputs 582 and 588 respectively from the rectifier 580 of FIG. 31 and the circuit 584 of FIG. 32. The difference amplifier circuit 592 amplifies the difference between the two received outputs 582 and 588. The amplified signal may then be passed to a processor (e.g., the processor 482 of FIG. 30). The processor may utilize this signal to determine if a condition of interest exists. The condition of interest, in some embodiments, may be related to the state of a tube.

The amplifier circuit 592 in FIG. 34 also includes a threshold detector 593. In other embodiments, the circuit 592 may instead include a window comparator. The threshold detector 593 may be included such that it may trigger an alarm if the voltage applied to the threshold detector 593 strays from an expected value. In some embodiments, the alarm may be triggered if the voltage deviates outside of a predefined threshold. In some additional embodiments, the threshold detector 593 may be configured to trigger an alarm if the output voltage crosses over a predefined threshold. The alarm may be any type or combination of types of suitable alarms such as, but not limited to those described above.

Figure 35:
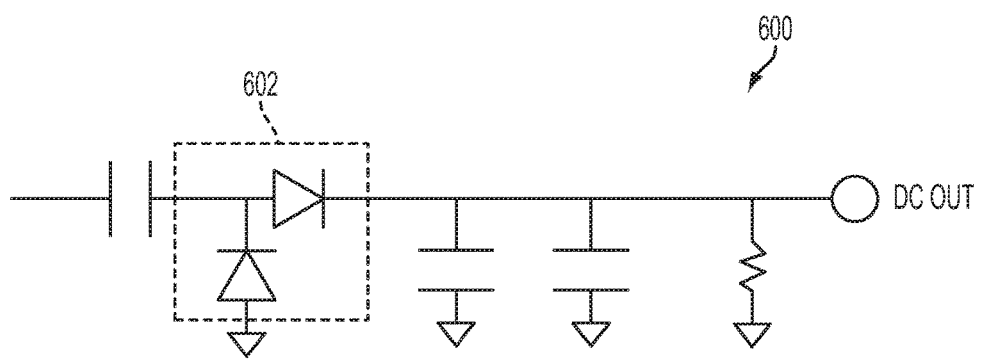

FIG. 35 shows example embodiment of a rectifier circuit 600 including a schottky diode pair 602. The example rectifier circuit 600 may be used to rectify the signal received by one of the receiving antenna embodiments disclosed herein into a DC output. The DC output may then be forwarded to a processor, a differential amplifier, or other component. In a preferred embodiment, the rectifier circuit 600 may be designed such that it mitigates or compensates for the temperature dependency of the voltage drop across the schottky diode pair 602.

Figure 36:
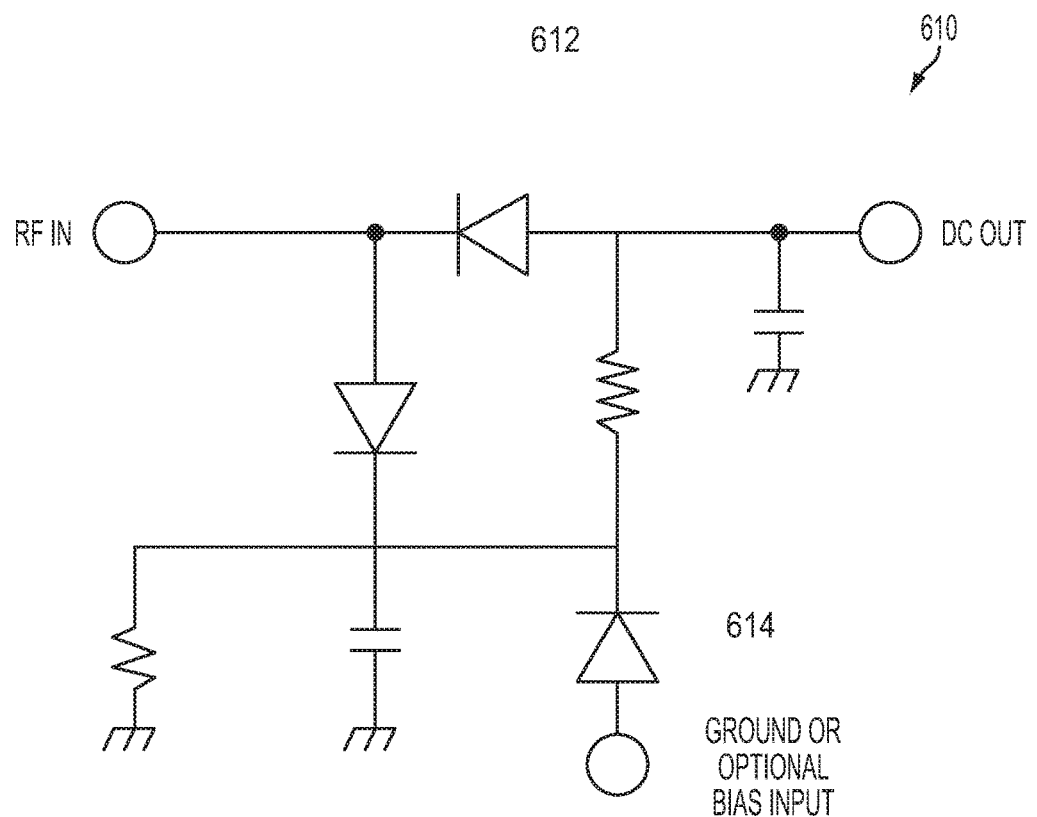
FIG. 36 shows an example rectifier circuit with temperature compensation for use in a system for detecting a bubble in accordance with an embodiment of the present disclosure.

FIG. 36 shows another example embodiment of a rectifier circuit 610. The rectifier circuit 610 may be coupled to, for example, any receiving antenna disclosure herein for providing a DC output to a processor, differential amplifier, or other component. The rectifier circuit 610 is constructed such that it has built in temperature compensation. As shown, the rectifier circuit 610 is designed such that it mitigates or compensates for the temperature dependency of the voltage drop across the schottky diode pair 612 with a nearly equal and opposite temperature change in a silicon diode 614.

Figure 37:
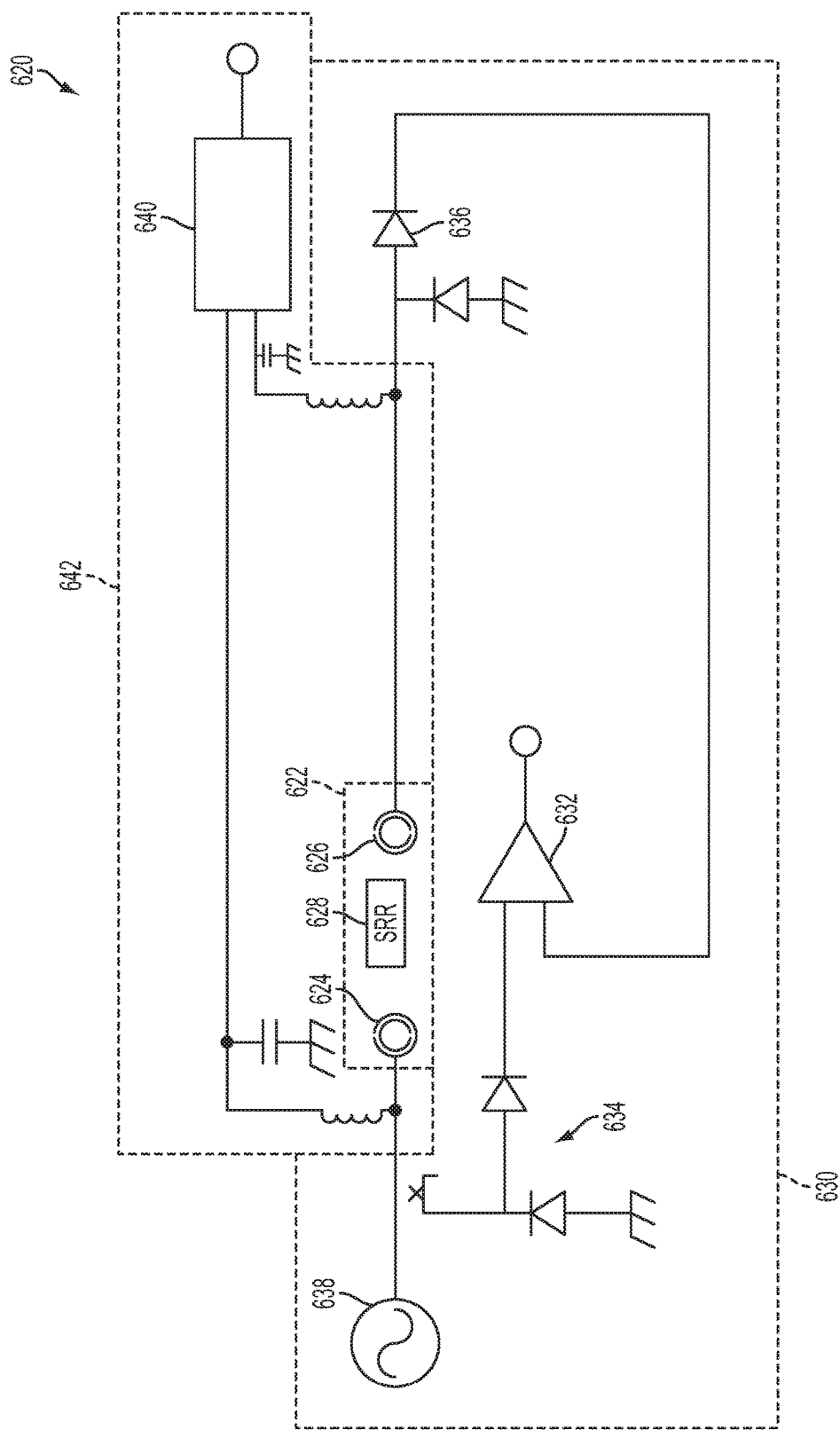
FIG. 37 shows an example schematic diagram of a ratio detector and moisture sensor for use in a system for detecting a bubble in accordance with an embodiment of the present disclosure.

FIG. 37 shows an example embodiment of a system 620 for detecting a bubble. As shown, the system 620 includes a split-ring resonator component 622. The split-ring resonator component 622 includes a transmitting antenna 624, a receiving antenna 626 and an SRR 628. The system 620 also includes a bubble detector component 630 with a ratio detector 632. Use of a ratio detector 632 in the bubble detector component 630 provides temperature compensation. As shown, the ratio detector 632 receives a DC output from two rectifiers 634, 636. The rectifier 634 creates a DC voltage representative of the output signal of the VCO 638. The second rectifier 636 creates a DC voltage representative of the signal received by the receiving antenna 626 of the split-ring resonator component 622. The ratio detector 632 outputs a signal relative to the ratio between the two voltages. This signal may then be forwarded to, for example, a processor (e.g., the processor 482 of FIG. 30).

Also shown in FIG. 37 is a moisture sensor 640 included as part of a moisture sensor component 642. Use of a moisture sensor 640 may be desirable because it allows the detection of liquid ingress or humidity. Both liquid ingress and humidity may change the dielectric loading of an SRR and thereby introduce output error. In some embodiments, the moisture sensor 640 may be a conductivity sensor. The moisture sensor 640 may be configured to generate a pass/fail signal to indicate whether or not moisture is present. Depending on the sensitivity of the moisture sensor 640, some embodiments may provide a more nuanced output. For example, some embodiments may be able to discriminate between the presence of a large volume of moisture and a small volume of moisture.

Figure 38:
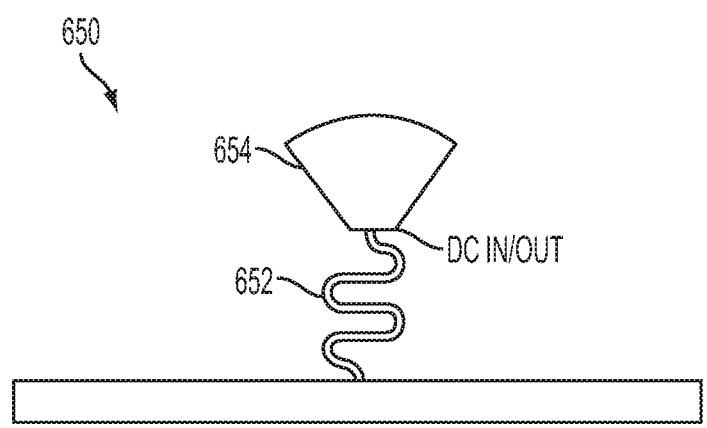
FIG. 38 shows an example microstrip radial stub in accordance with an embodiment of the present disclosure.

FIG. 38 shows an example of a microstrip radial stub 650 in accordance with an embodiment of the present disclosure. The example microstrip radial stub 650 includes an inductor portion 652 and a capacitor portion 654. The microstrip radial stub 650 allows DC to flow in and out without affecting RF performance at a particular frequency range. In some embodiments, the frequency range may be approximately 4-5 GHz. Additionally, the microstrip radial stub 650 shown in FIG. 38 is designed to reject any ingress from signals of devices operating at the ISM band (Wireless LANs, cordless phones, etc.). In order to allow DC in or out with minimal effect on signals at the desired frequency or frequencies, the microstrip radial stub 650 may be designed to have high impedance at those frequencies.

Figure 39:
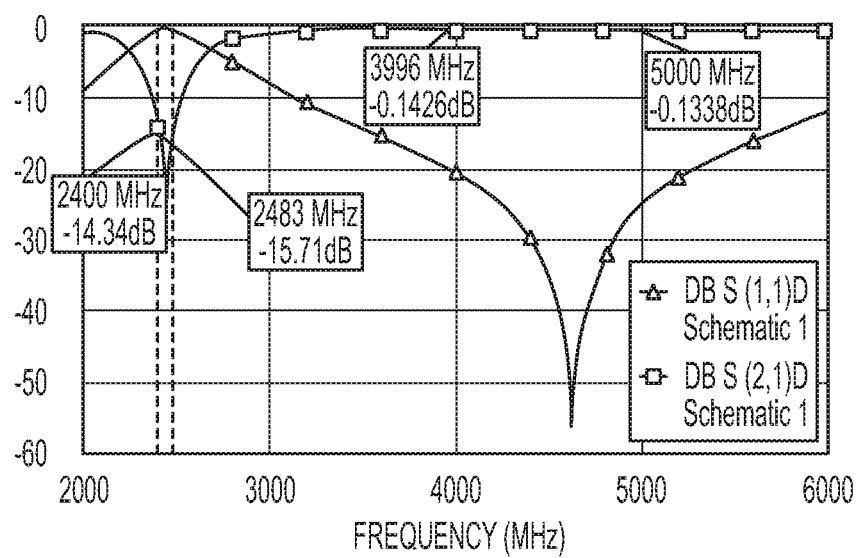
FIG. 39 shows an example graph depicting the impedance over a range of frequencies for the microstrip radial stub of FIG. 38 in accordance with an embodiment of the present disclosure.
Figure 40:
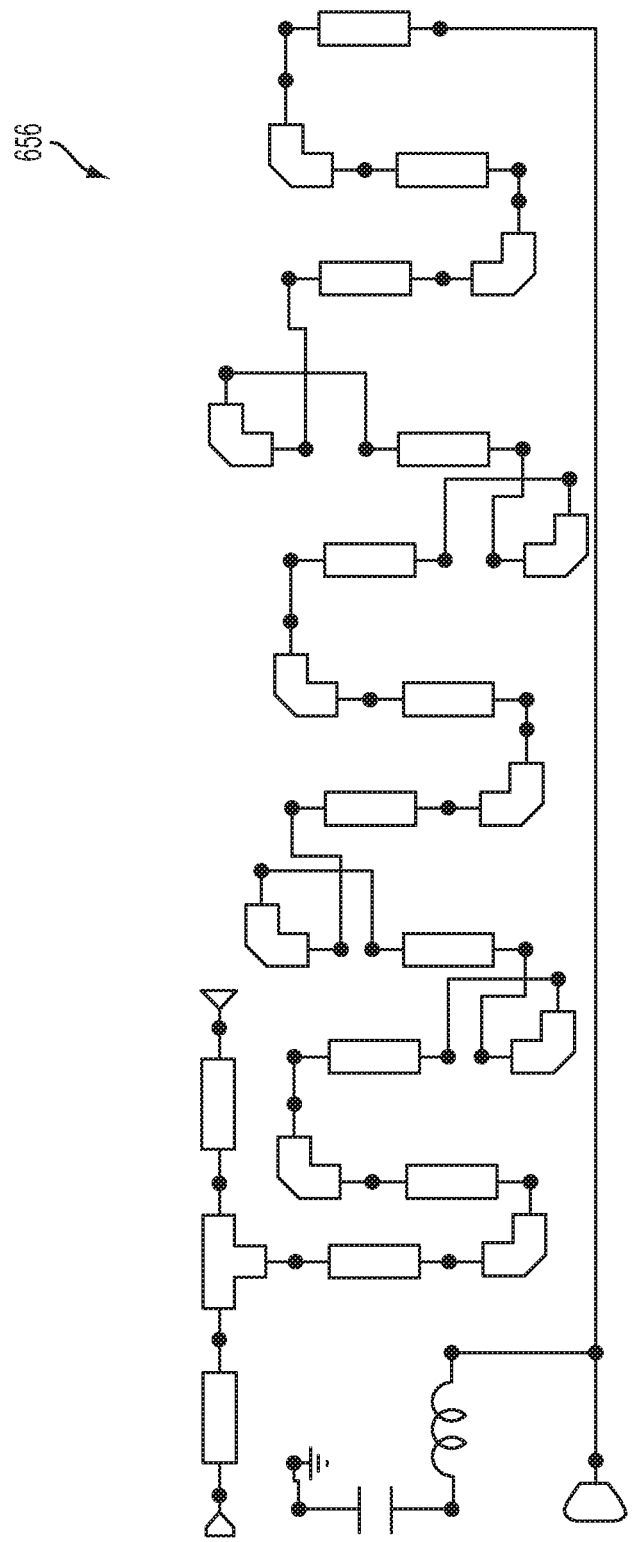
FIG. 40 shows a specific detailed example of the microstrip radial stub shown in FIG. 38 in accordance with an embodiment of the present disclosure.

The performance of the example microstrip radial stub 650 over a range of 2000-6000 MHz is shown in the graph in FIG. 39. FIG. 40 depicts a specific detailed example of a microstrip circuit 656 which may perform the function of the microstrip radial stub 650 shown in FIG. 38. The example microstrip radial stub 650 may be used as the decouplers between the bubble detector component 630 and the moisture sensor component 642 in FIG. 37.

Figure 41:
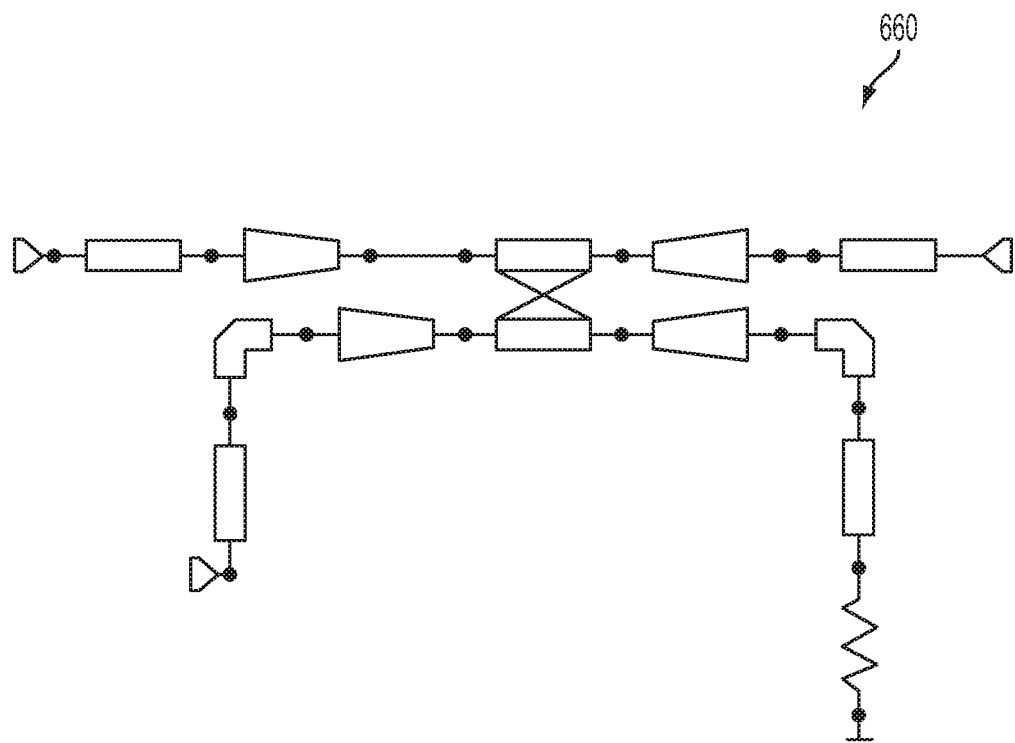
FIG. 41 shows an example schematic microstrip coupler in accordance with an embodiment of the present disclosure.
Figure 42:
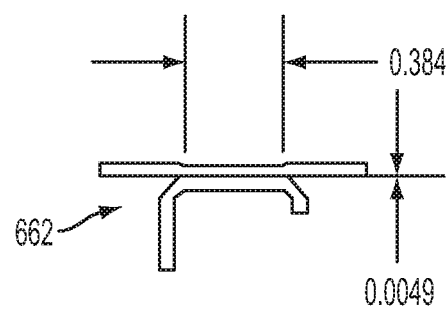
FIG. 42 shows a specific example of a microstrip coupler and its specific geometry in accordance with an embodiment of the present disclosure.
Figure 43:
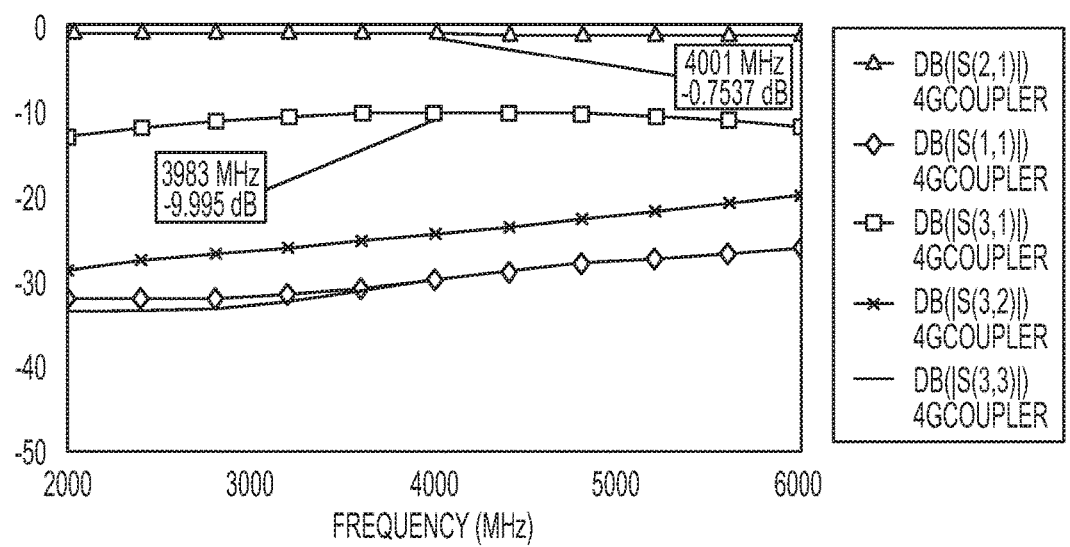
FIG. 43 shows an example graph detailing the performance of the microstrip coupler of FIG. 42 in accordance with an embodiment of the present disclosure.

FIG. 41 shows an example embodiment of a microstrip coupler 660 in accordance with an embodiment of the present disclosure. The microstrip coupler 660 embodiment shown may be used in any suitable embodiment described herein utilizing a directional coupler. A specific example embodiment detailing the specific geometry of an example microstrip coupler 662 is shown in FIG. 42. FIG. 43 shows an example graph of the coupling characteristics of the example microstrip coupler 662 illustrated in FIG. 42.

Figure 44:
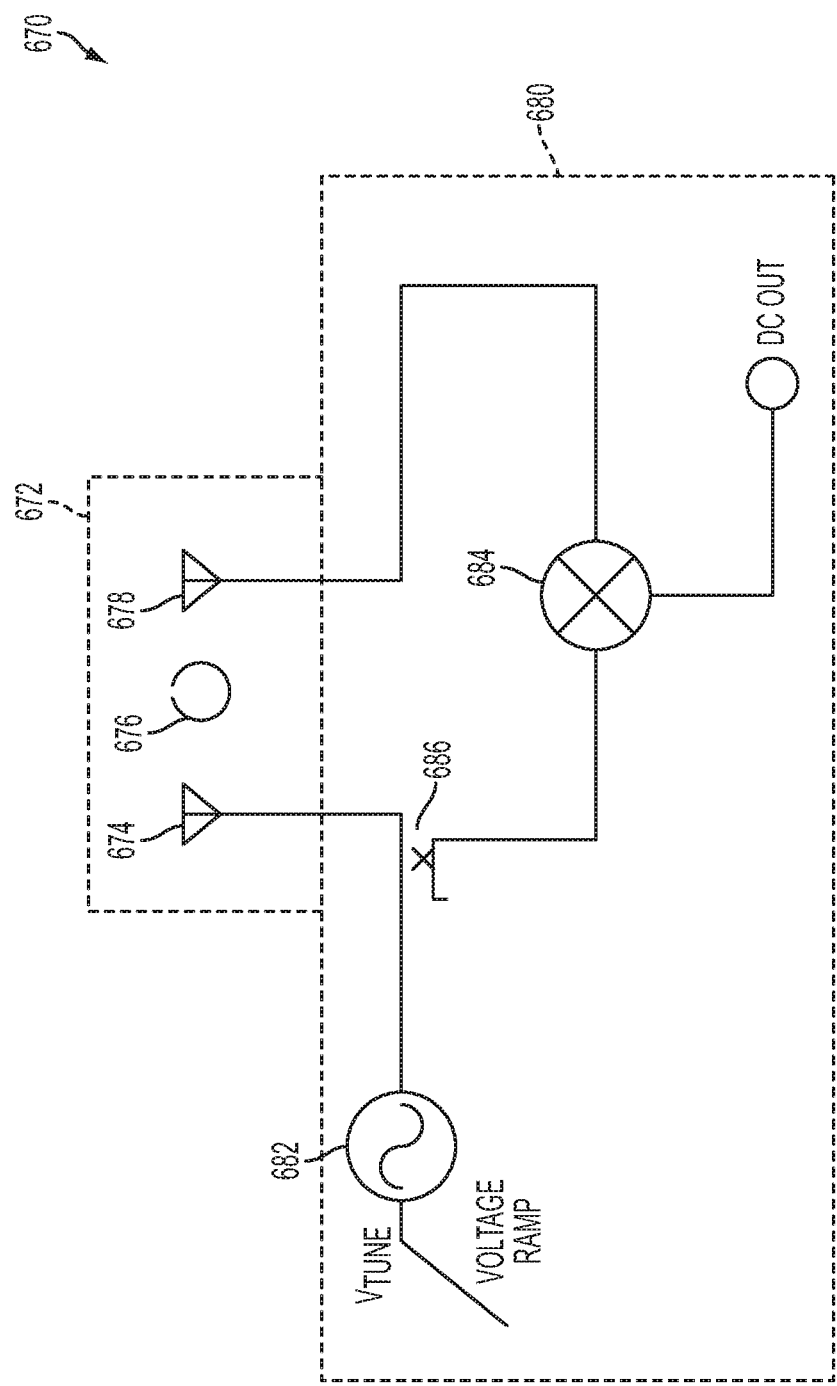
FIG. 44 shows an example of part of a system for detecting a bubble which is configured to measure phase change in accordance with an embodiment of the present disclosure.

FIG. 44 shows another example embodiment of a system 670 for detecting a bubble. As shown, the system 670 includes a split-ring resonator component 672. The split-ring resonator component 672 includes a transmitting antenna 674, an SRR 676, and a receiving antenna 678. The system 670 also includes a bubble detection component 680. The bubble detector component 680 in FIG. 44 is designed to measure a parameter such as the phase shift or phase response of the SRR 676. As shown, the output of a VCO 682 is transmitted via the transmitting antenna 674 of the split-ring resonator component 672. The bubble detector component 680 includes a mixer 684 which receives a signal from the output of the VCO 682 via a directional coupler 686. The mixer 684 also receives an output from the receiving antenna 678 of the split-ring resonator component 672. The bubble detector component 680 may include an adjustment means to allow the signal from the receiving antenna 678 to be tailored to the same amplitude as the signal traveling to the mixer 684 from the directional coupler 686. As is well known in the art, two identical frequency, constant-amplitude signals that are sent to a mixer 684 will result in a DC output which is proportional to the phase difference between the two signals. The DC output may be used by a processor (e.g., the processor 482 of FIG. 30) to determine the existence of a condition of interest, for example, the presence of a bubble in a fluid line. This is due to the fact that the phase shift of the signal which passes through the SRR 676 will depend on the resonant properties of the SRR 676. Since the resonant properties of the SRR 676 will change depending on the dielectric loading of the SRR 676, the phase shift of a specific frequency introduced by a full tube will be different than that introduced by a tube including an air bubble.

Figure 45:
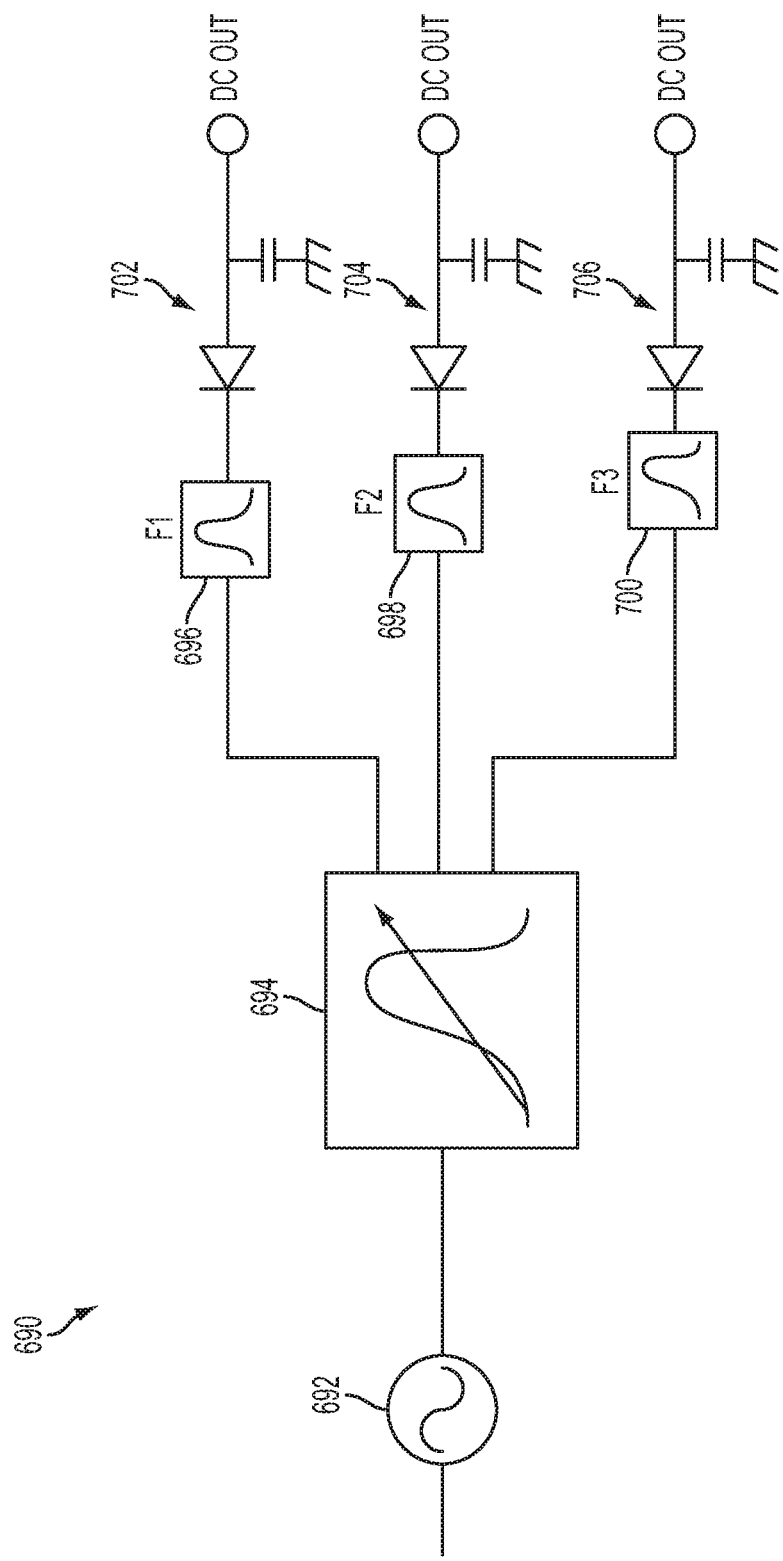
FIG. 45 shows another example of part of a system for detecting a bubble in accordance with an embodiment of the present disclosure.

FIG. 45 shows another example embodiment of part of a circuit 690 for an air bubble sensor. As shown, the circuit 690 includes a VCO 692. The VCO 692 may produce a modulated transmission with subcarriers or a modulated spectrum. This signal may be transmitted by a transmitting antenna (not explicitly shown). The signal may pass through an SRR 694 (shown here as a variable passband filter) and be received by a receiving antenna (not explicitly shown). The received modulated transmission may then be fed, for example, to a number of passband filters 696, 698, 700 which are tuned to recover information about the transmission of particular frequencies.

In the part of the circuit 690 shown, the passband filter 696 is included for a first center frequency, F1, the passband filter 698 is included for a second center frequency, F2, and the passband filter 700 is included for a third center frequency, F3. The signal from each passband filter 696, 698, 700 may then be rectified into a DC output voltage by respective rectifiers 702, 704, 706. The DC output voltages may be used by a processor (not shown) to determine where the passband of the SRR 694 is located in the frequency spectrum. In turn, this information may be used to determine a condition of interest, e.g. tube full, tube empty, air bubble, etc.

Figure 46:
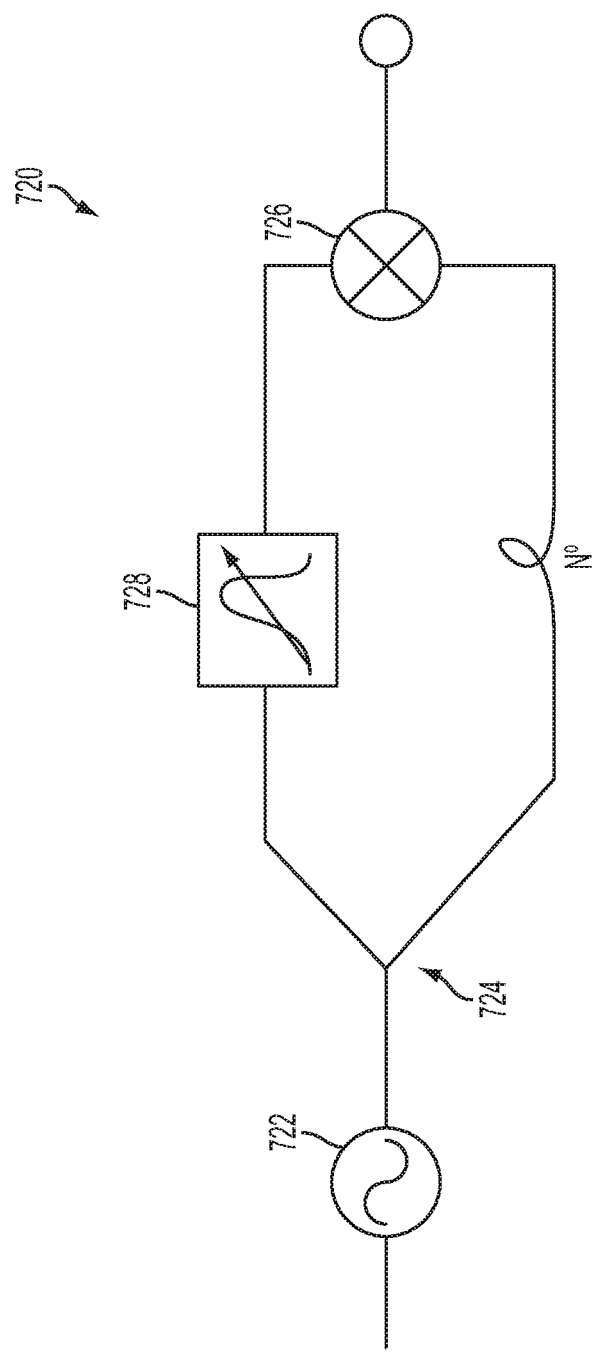
FIG. 46 shows another example of part of a system for detecting a bubble in accordance with an embodiment of the present disclosure.

FIG. 46 depicts an example embodiment of part of a circuit 720 which may be used to detect a condition of interest using phase shift or propagation delay. As shown, a VCO 722 generates a signal. The signal travels to a power splitter 724 and is split into parts. One part of the signal travels through the SRR 728 and to a frequency mixer 726, and another part is delay delayed by a predefined amount. The split ring resonator 728 may be part of a split ring resonator component such as any of the split ring resonator components described herein. Depending on the status of, for example, a tube near the split-ring resonator 728 the received signal from the SRR 728 will be phase shifted a specific amount. By sending this signals to the frequency mixer 726 a DC output can be created which is proportional to the phase difference between both parts of the signal. This signal may then be sent to another component such as a processor in order to determine if a particular condition of interest exists.

Figure 47:
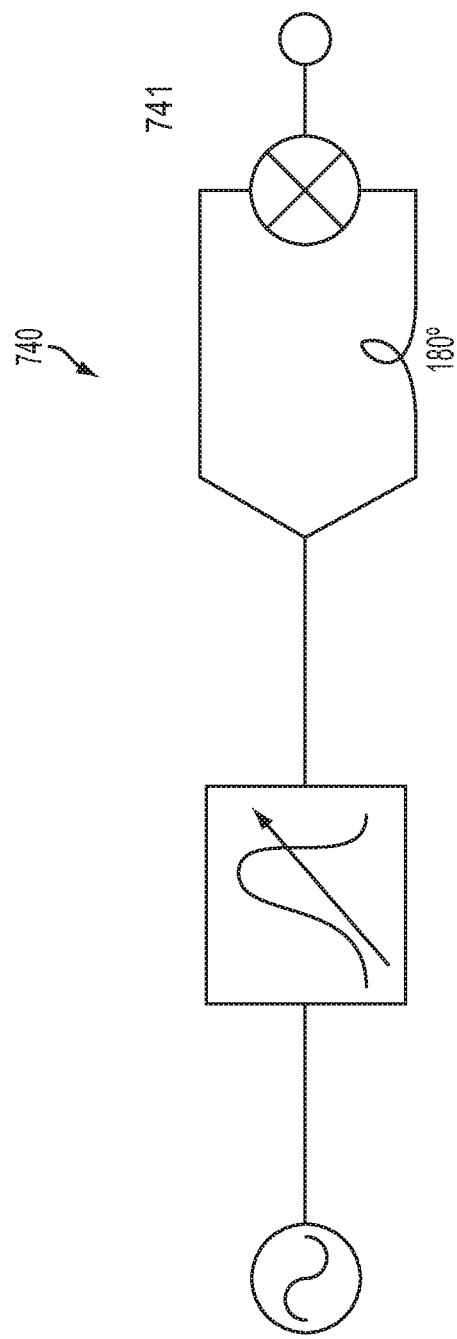
FIG. 47 shows another example of part of a system for detecting a bubble in accordance with an embodiment of the present disclosure.

FIG. 47 illustrates another example part of a circuit 740 which may be used to measure a phase shift or a group delay to determine the existence of a condition of interest. The VCO 722 applies a signal (via a transmitting antenna that is not shown) into a SRR 728, which is then sent through an IQ mixer 741. The results of the IQ mixer 741 may be used to estimate whether a condition exists, e.g., a bubble within a tube, using a processor (e.g., the processor 482 of FIG. 30).

Figure 48:
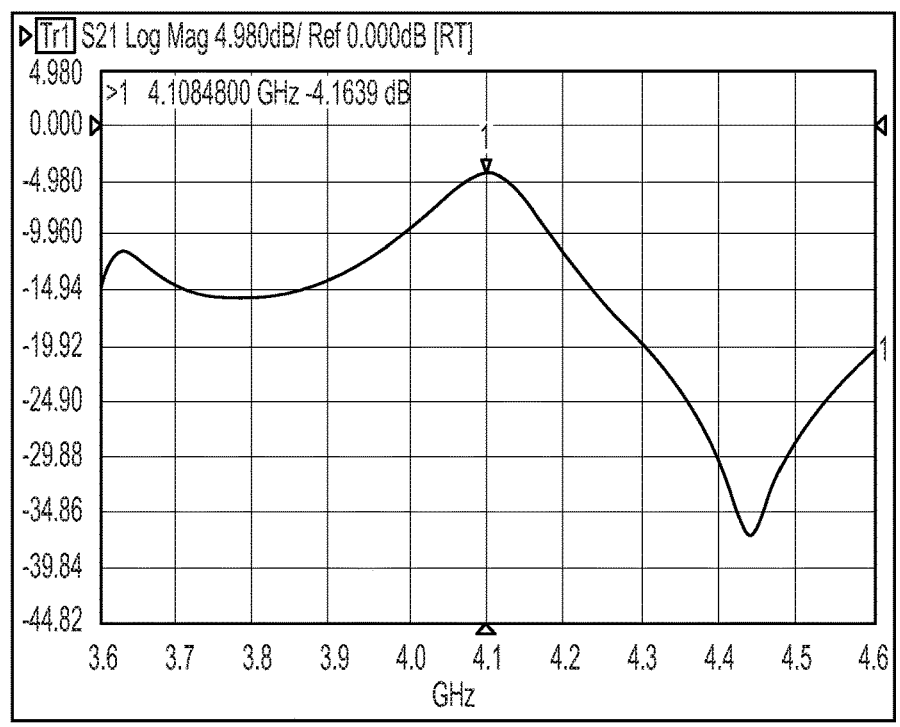
FIG. 48 shows an example graph of the S21 parameter of an example split ring resonator component over a sweep of frequencies with an empty tube in the split ring resonator component in accordance with an embodiment of the present disclosure.
Figure 49:
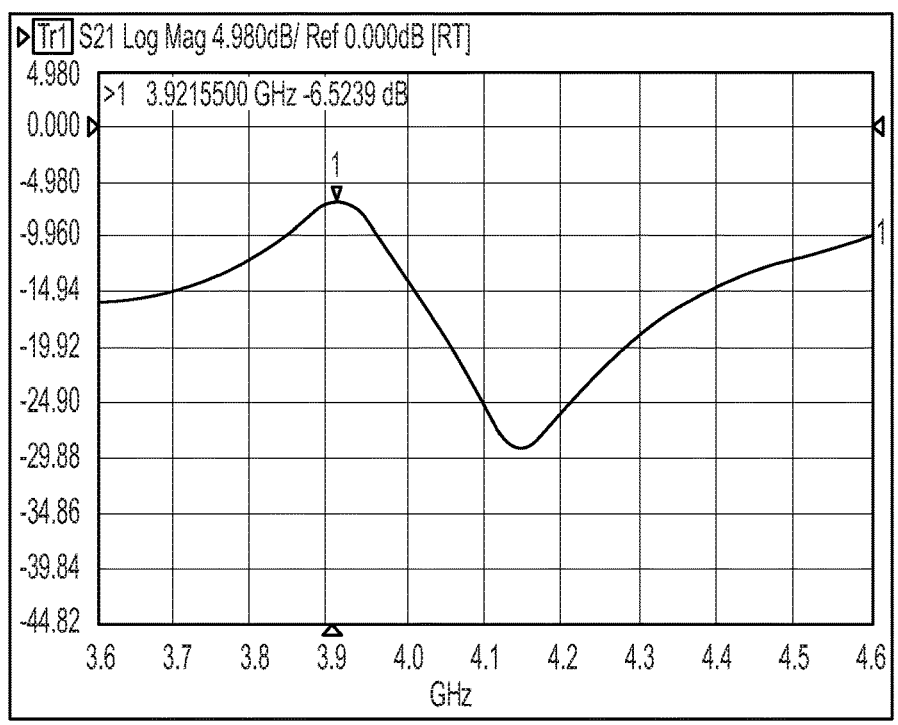
FIG. 49 shows an example graph of the S21 parameter of the example split ring resonator component of FIG. 48 over a sweep of frequencies with a full tube in the split ring resonator component in accordance with an embodiment of the present disclosure.

FIG. 48 and FIG. 49 show a graph of the S21 parameter of an example SRR component over a sweep from 3.6 GHz to 4.6 GHz as measured by a network analyzer. Each test was performed by controlling the dielectric loading of an SRR in the example SRR component. The graph in FIG. 48 measured the S21 parameter of a tube which was completely empty (air filled). The graph in FIG. 49 measured the S21 parameter of a tube which was completely filled with fluid thereby increasing the dielectric loading of the SRR. As shown, the lowest amount of loss seen with the empty tube occurred at approximately 4.1 GHz. With a tube full of fluid, the lowest amount of loss seen occurred at approximately 3.92 GHz. A processor may be used to monitor for such a shift in the S21 parameter in order to determine if an air bubble exists in a tested fluid line. In some embodiments, a processor may monitor for a deviation from an initial measurement. The initial measurement may be taken during a calibration procedure on a tube know to be empty or full and then stored in memory.

Figure 50:
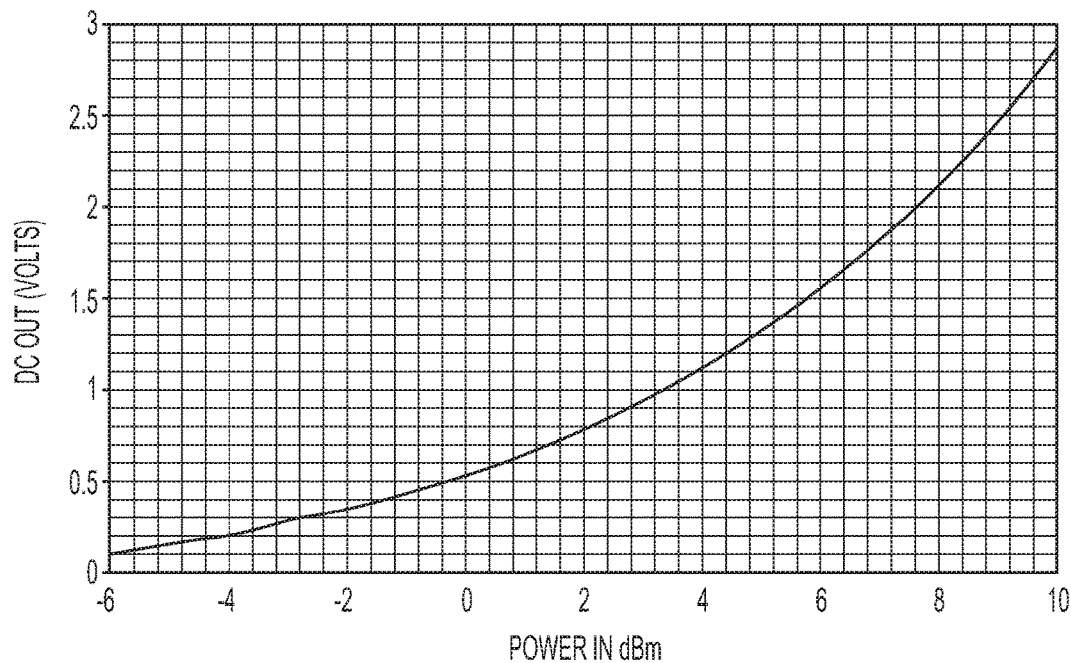
FIG. 50 shows an example graph illustrating the change in output voltage of an example rectifier in relation to the power of a signal received by a receiving antenna in accordance with an embodiment of the present disclosure.

FIG. 50 shows an example graph illustrating the change in output voltage of an example rectifier in relation to the power of a signal received by a receiving antenna. As shown, the greater the power of the signal at the receiving antenna, the greater the voltage. Thus, a processor may use the voltage from an example rectifier to determine the loss or gain of a transmitted signal which reaches a receiving antenna.

Figure 51:
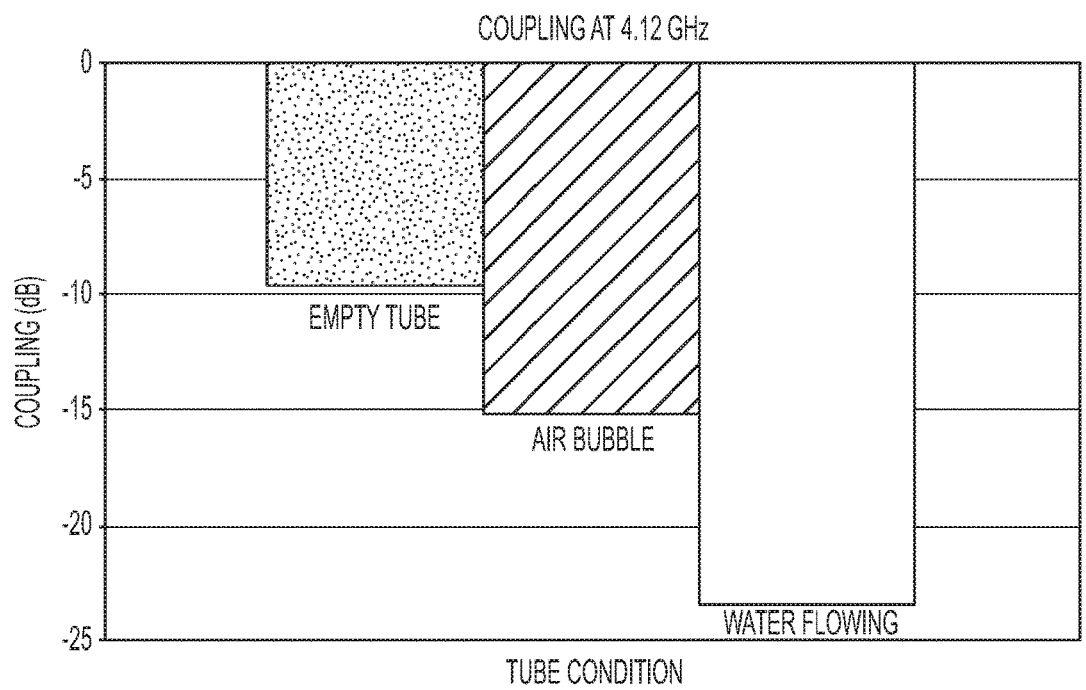
FIG. 51 shows an example graph illustrating the power coupling at 4.12 GHz across an example SRR component with varying tube conditions in accordance with an embodiment of the present disclosure.

FIG. 51 shows an example graph illustrating the power coupling at 4.12 GHz across an example SRR component with varying tube conditions. As shown, the coupling is best when the tube is empty. When the tube includes an air bubble, that is when the tube is partially filled with fluid, more loss is experienced. When the tube is completely full of fluid, for example when water is flowing through the tube, loss is greatest. This suggests that the resonant frequency of the SRR in the example SRR component is nearest 4.12 GHz when the capacitance value of the SRR is being influenced by an empty tube. A processor may monitor a signal being transmitted at a constant frequency for such deviations to determine if a condition of interest exists. In some embodiments, the frequency of the transmitted signal may be chosen such that it is at the resonant frequency of the SRR in the example SRR component when the tube is full or alternatively when the tube is empty.

Figure 52:
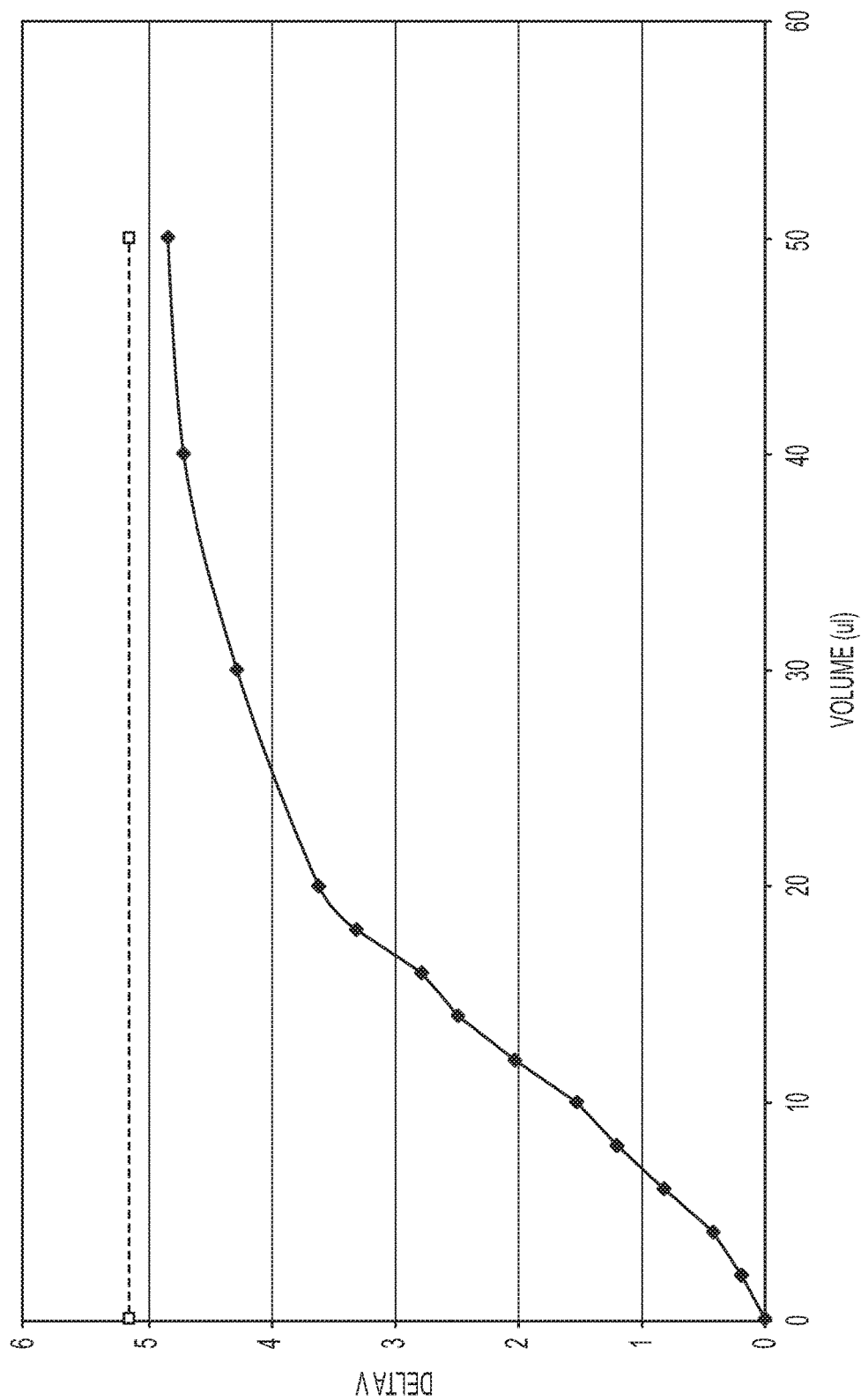
FIG. 52 shows an example graph illustrating the difference in output voltage of an air bubble sensor over bubble volume in accordance with an embodiment of the present disclosure.

FIG. 52 shows another example graph. The example graph in FIG. 52 shows the difference in output voltage of an air bubble sensor over bubble volume. The example graph was created by transmitting a signal at a constant frequency. The graph plots two tests. One test was performed by introducing specific volumes of air into a tube and measuring the change in voltage of the rectified signal from a receiving antenna of a split-ring resonator component. As is shown, no bubble, i.e. the tube is full, is the voltage reference point. The output of the sensor was tested with bubbles having volumes of as little as 2 µl and as large as 50 µl. As shown, the difference in output voltage grows in step with the volume of the bubble. This is so because the power coupling is altered by bubble volume. Additionally as shown, the sensor is capable of detecting a bubble at the smallest test bubble volume of 2 µl. For reference, the graph also includes a second test on a fluid line which was completely empty. This test was performed over a period of time. As shown, the output voltage is generally static at just over a 5V difference from the measured output voltage of a tube full of fluid. Thus the output voltage provides information on the status of a tube. The output voltage may therefore be monitored for changes from, for example, an initial amount to determine the existence of an air bubble as well as its approximate size.

Figure 53:
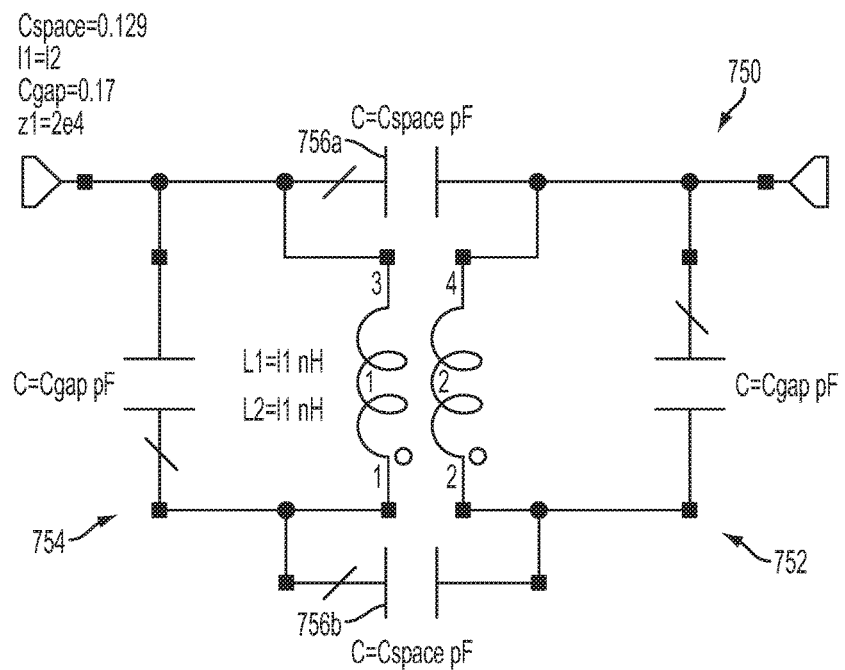
FIG. 53 shows an approximate equivalent circuit of two example split ring resonators with specific capacitance and inductance values given reflecting those which would be generated in the presence of an empty tube in accordance with an embodiment of the present disclosure.

FIG. 53 depicts an approximate equivalent circuit 750 representing two example SRRs positioned near an empty tube. As shown, the circuit 750 includes a first LC circuit 752 and a second LC circuit 754. The first LC circuit 752 and second LC circuit 754 represent the two SRRs. In the embodiment shown, capacitors 756a and 756b represent the capacitance between the two SRRs. The capacitance values given are in picofarads and, as mentioned above, are those generated in the presence of an empty tube.

Figure 54:
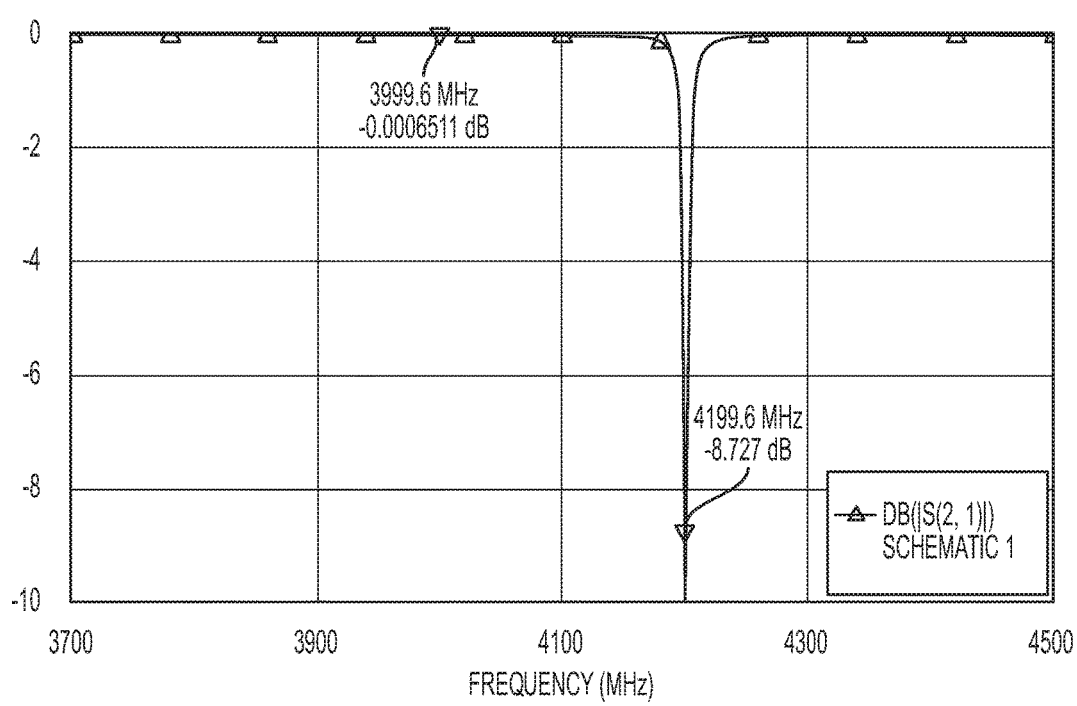
FIG. 54 shows an example graph illustrating the S21 parameter of the example circuit shown in FIG. 53 in accordance with an embodiment of the present disclosure.

FIG. 54 shows a graph of the S21 parameter of the SRRs represented by the circuit 750 of FIG. 53 with the capacitance values given in FIG. 53. The S21 parameter is plotted over a sweep from a frequency of 3700 MHz to 4500 MHz. As shown, a notch occurs at approximately 4200 MHz with the capacitance values created by the dielectric properties of the empty tube. This notch occurs at the anti-resonant frequency of the SRRs. The frequency at which the notch occurs will change depending on the dielectric constant of the tube. This is shown in FIGS. 55 and 56.

Figure 55:
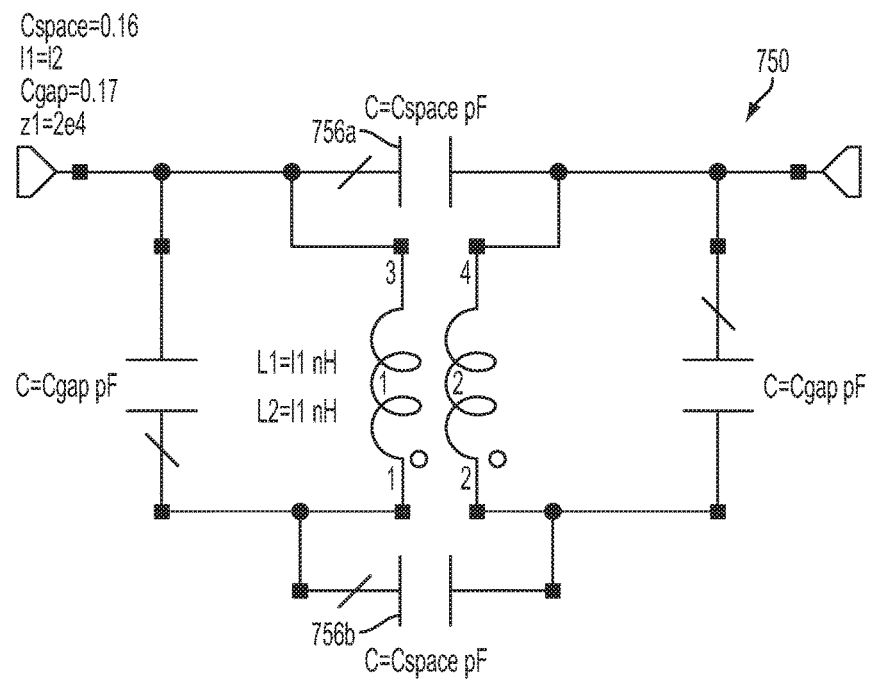
FIG. 55 shows an approximate equivalent circuit of two example split ring resonators with specific capacitance and inductance values given reflecting those which would be generated in the presence of a full tube in accordance with an embodiment of the present disclosure.

FIG. 55 shows a second drawing of the circuit 750 of the same two SRRs drawn in FIG. 53. The capacitance values given are in pF and are those generated when in the presence of a full tube. As shown, the capacitance difference between the circuit in FIG. 53 and the circuit in FIG. 55 is ~0.03 pF with the circuit in FIG. 55 having the higher capacitance value due to the higher dielectric constant of the fluid within the tube.

Figure 56:
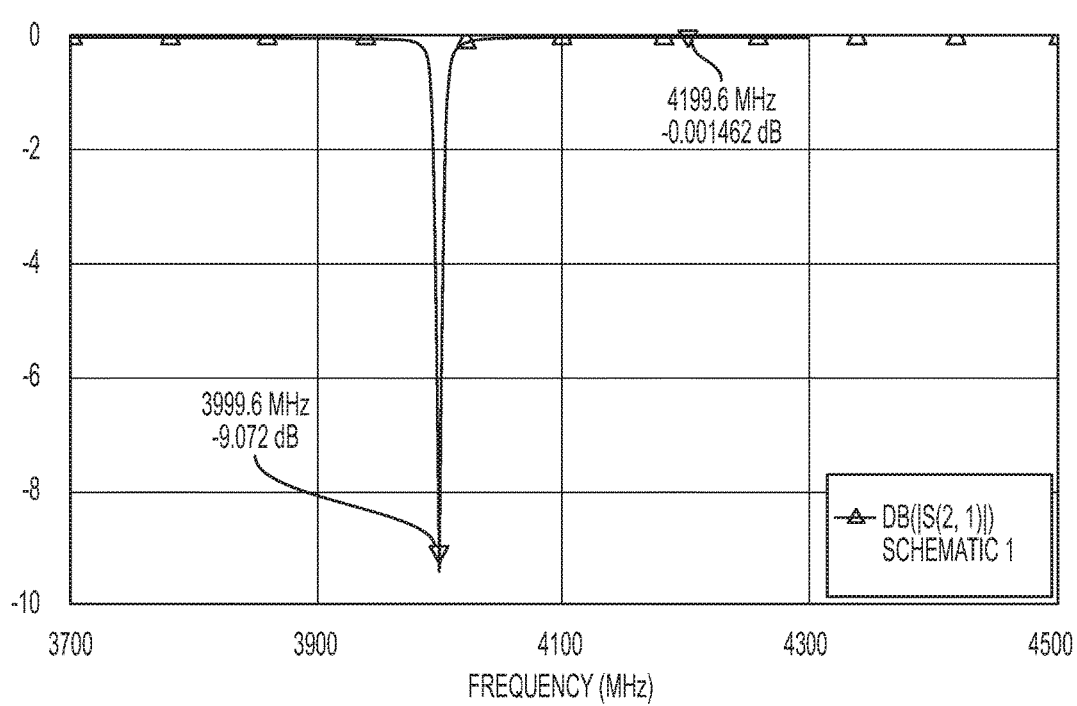
FIG. 56 shows an example graph illustrating the S21 parameter of the example circuit shown in FIG. 55 in accordance with an embodiment of the present disclosure.

FIG. 56 shows a graph of the S21 parameter of the SRRs represented by the circuit 750 in FIG. 55 with the capacitance values given in FIG. 55. The S21 parameter is plotted over a sweep from a frequency of 3700 MHz to 4500 MHz. As shown, a notch at the anti-resonant frequency also occurs in this graph. The notch, however, occurs at a different frequency. While the notch in FIG. 54 occurs at approximately 4200 MHz, the notch in FIG. 56 occurs at approximately 4000 MHz. This shift in anti-resonant frequency caused by the dielectric properties of the surrounding material may be used by a processor to determine if the tube is empty or full.

When an air bubble is present in the tube the capacitance value will be somewhere between that given in FIG. 53 and FIG. 55. Thus, in such an event, the notch would be somewhere between the 4000 MHz value and the 4200 MHz value. The location of the notch would be dependent on the size of the air bubble in the tube. Consequentially, the location of the notch in the frequency sweep may be used to detect the presence of an air bubble. Additionally, the notch may also be informative as to the size of the air bubble present.

Figure 57:
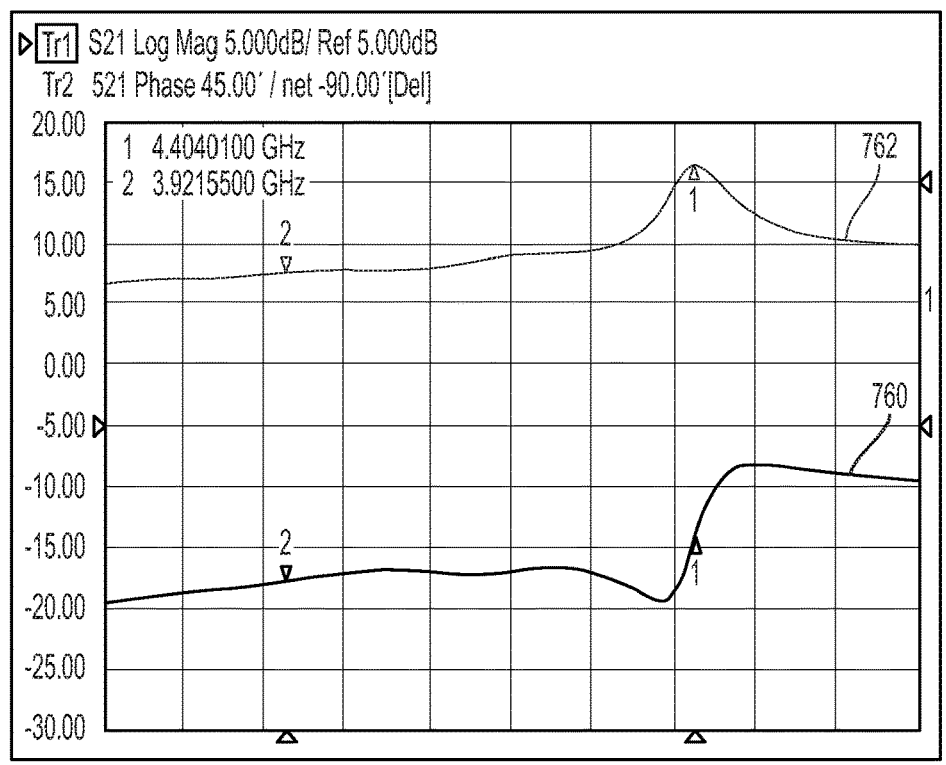
FIG. 57 shows an example graph depicting the amplitude and phase shift of received energy which was transmitted through an example split ring resonator component with an empty tube in accordance with an embodiment of the present disclosure.

FIG. 57 shows an example graph, as measured by a network analyzer, of the transmission characteristics of energy through a split ring resonator component. The graph in FIG. 57 measured transmission with an empty tube in place in the split ring resonator component. Two parameters are plotted in the graph. Line 760 plots the amplitude of the transmission over the swept frequencies. Line 762 plots the phase shift of the transmission over the frequency swept. As shown by line 760, a rise in transmission occurs at approximate 4.4 GHz. Likewise, a change in the phase shift also occurs and is centered around the 4.4 GHz frequency.

Figure 58:
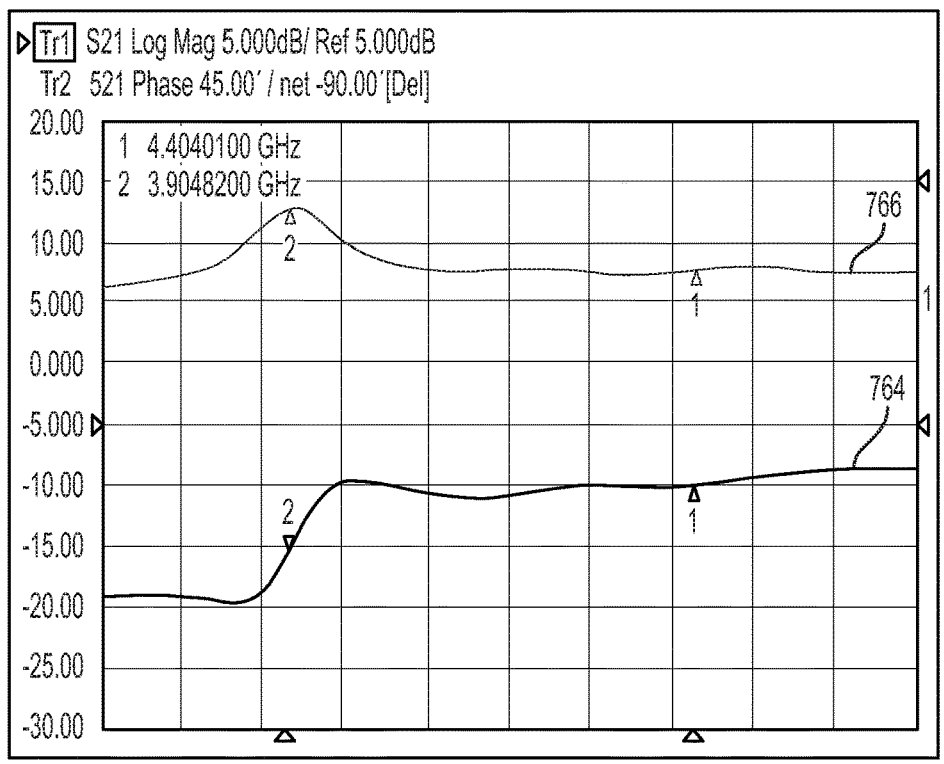
FIG. 58 shows an example graph plotting the amplitude and phase shift of received energy which was transmitted through the same split ring resonator component in FIG. 57 with the tube full of fluid in accordance with an embodiment of the present disclosure.

FIG. 58 shows another graph, as measured by a network analyzer, of the transmission characteristics of energy through the same split ring resonator component in FIG. 57. The graph in FIG. 58 measured transmission with a tube which was full of water. The same two parameters are plotted in the graph. Line 764 plots the amplitude of the transmission over the swept frequencies. Line 766 plots the phase shift of the transmission over the frequencies swept. As shown, the transmission behaves differently when the tube is full of water. As shown by line 764, a rise in transmission amplitude occurs at approximately 3.9 GHz. A change in the phase shift also occurs and is centered around the 3.9 GHz frequency. As above, these shifts may be used by a processor of an air bubble detection component (see FIG. 4) to determine whether tube is full of water or if air exists within the tube. Among other applications, this may be used for automatic priming of a tube. The shifts may also be used to determine whether an air bubble is in the tube. For example, if the rise in amplitude and change in phase shift occurred at approximately 4.1 GHz, it would be indicative that the tube included both water and some air.

Figure 59:
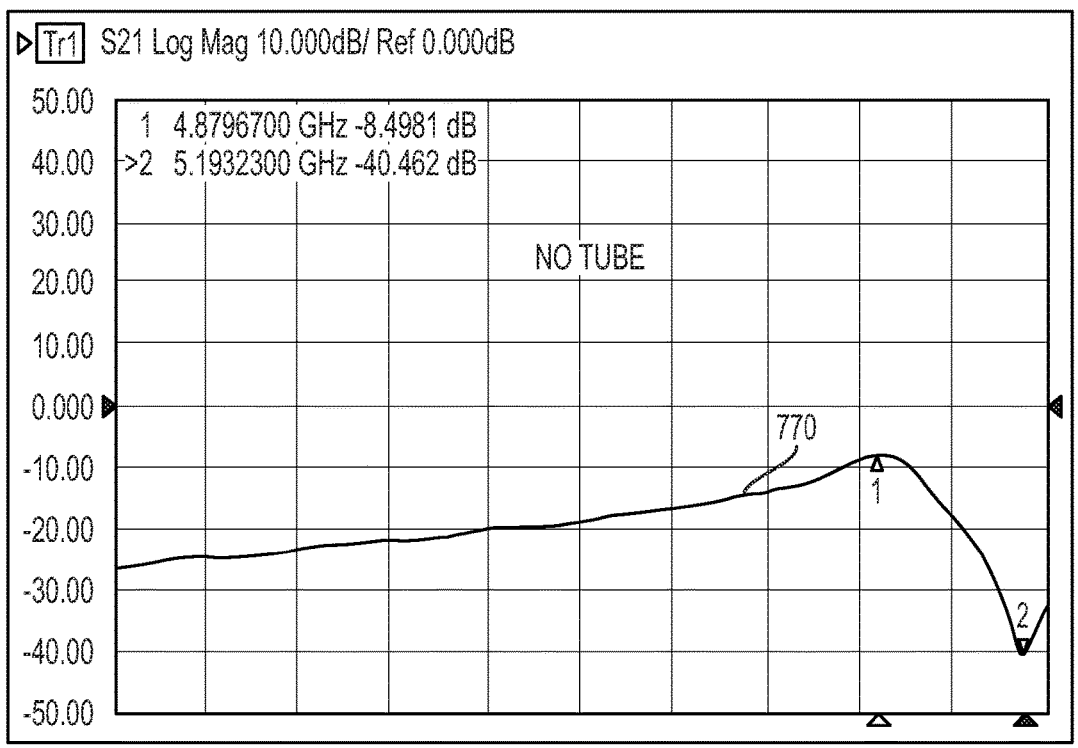
FIG. 59 shows another example graph illustrating the amplitude of received energy which was transmitted through another example split ring resonator component when no tube was in place in the split ring resonator component in accordance with an embodiment of the present disclosure.

FIGS. 59-62 depict another series of graphs as measured by a network analyzer. These graphs measure the transmission of energy through another example split ring resonator component. The graph in FIG. 59 shows the power of the received transmission over a frequency sweep with no tube present in the split ring resonator component. As shown by line 770, the power of the transmission experiences the smallest amount of loss at approximately 4.9 GHz. The amplitude of the transmission thereafter experiences an increase in loss until approximately 5.2 GHz.

Figure 60:
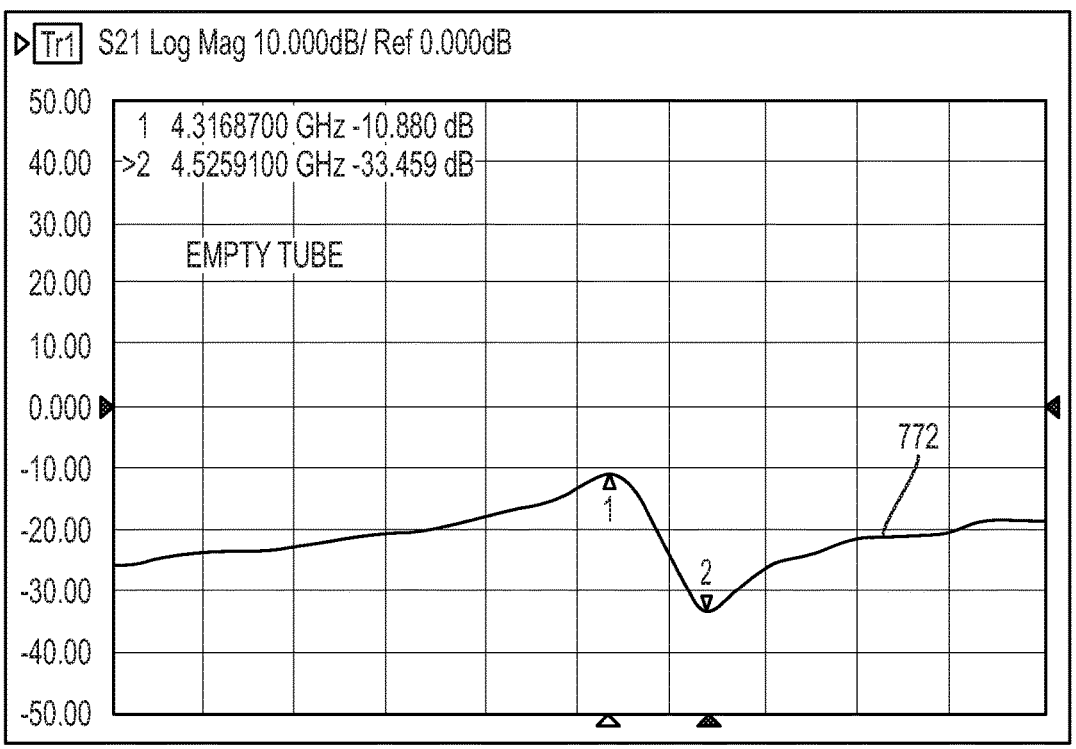
FIG. 60 shows an example graph illustrating the amplitude of received energy which was transmitted through the example split ring resonator component of FIG. 59 when an empty tube was in place in the split ring resonator component in accordance with an embodiment of the present disclosure.

FIG. 60 depicts the power of the received transmission over the same frequency sweep with an empty tube present in the split ring resonator component. As shown by line 772, a similar low point followed thereafter by a high point in loss occurs. The low loss point in the transmission occurs at approximately 4.3 GHz, a shift of approximately 0.6 GHz from FIG. 59. The largest amount of loss occurs at approximately 4.5 GHz, a shift of approximately 0.7 GHz from FIG. 59. Thus the transmission of energy through a split ring resonator component may be used to determine whether or not a tube is present in the split ring resonator component.

Figure 61:
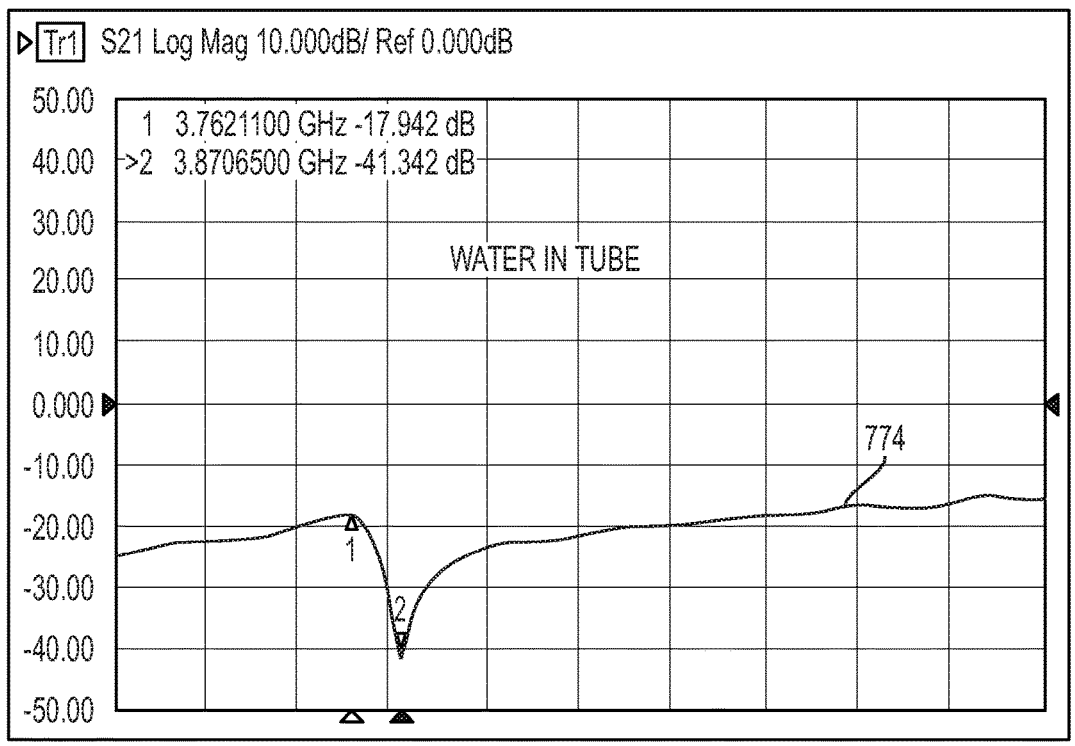
FIG. 61 shows an example graph illustrating the amplitude of received energy which was transmitted through the example split ring resonator component in FIG. 59 when a full tube was in place in the split ring resonator component in accordance with an embodiment of the present disclosure.

FIG. 61 depicts the power of the received transmission for the same frequency sweep with a full tube present in the split ring resonator. As shown by line 774, a similar low point followed thereafter by a high point in loss occurs. The low loss point in the transmission occurs at approximately 3.75 GHz. The high loss point thereafter occurs at approximately 3.9 GHz. Again, both of these points are at a lower frequency then those that occur when no tube is present and when an empty tube is present. Thus, the transmission of energy through the split-ring resonator component may be used to determine if a tube is present and if so the contents of the tube.

Figure 62:
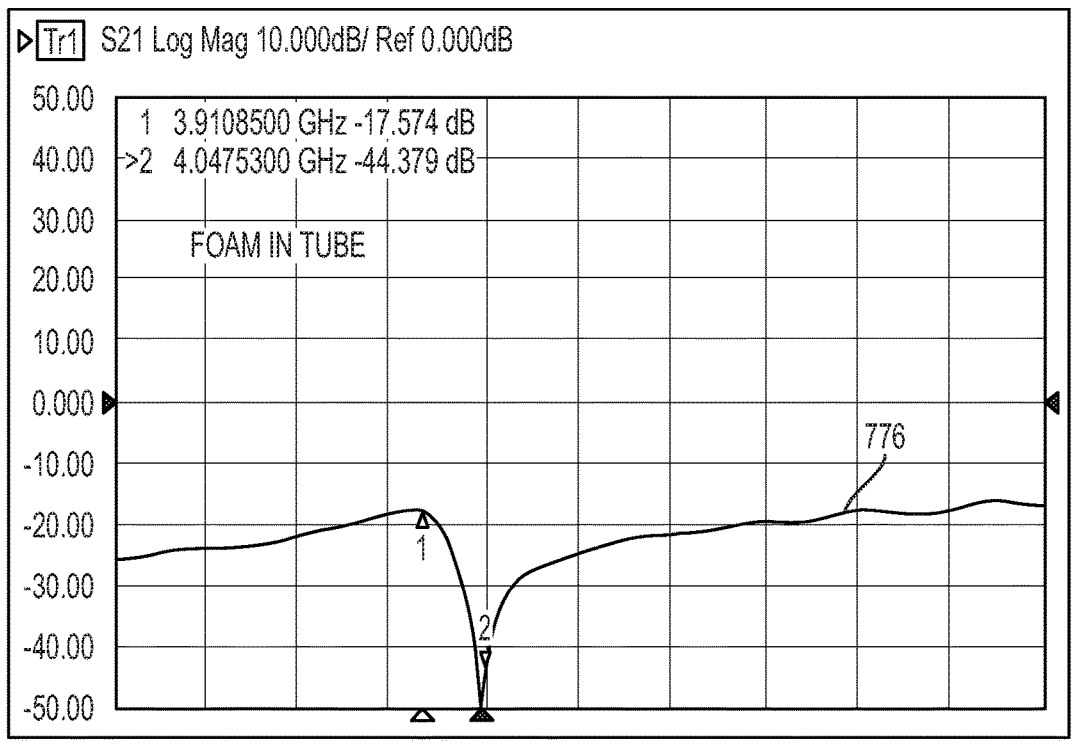
FIG. 62 shows an example graph illustrating the amplitude of received energy which was transmitted through the example split ring resonator component in FIG. 59 when a tube full of foam with dielectric properties mimicking those of a fluid with an air bubble was in place in the split ring resonator component in accordance with an embodiment of the present disclosure.

FIG. 62 depicts another graph of the power of the transmission over the same frequency sweep with a tube present in the split-ring resonator component. The tube used to create the graph in FIG. 62 was filled with foam. The foam was chosen such that its dielectric properties would be similar to those which would be created when an air bubble was in place in the tube. As shown by line 776, a similar low loss point followed thereafter by a high loss point occurs. The low loss point occurs at approximately 3.9 GHz. The high loss point occurs at approximately 4 GHz. These values are both different from the values created with an empty tube and those created with a full tube. Thus, using the transmission of energy through a split-ring resonator component it may be determined if an air bubble is present in a fluid line.

Figure 63:
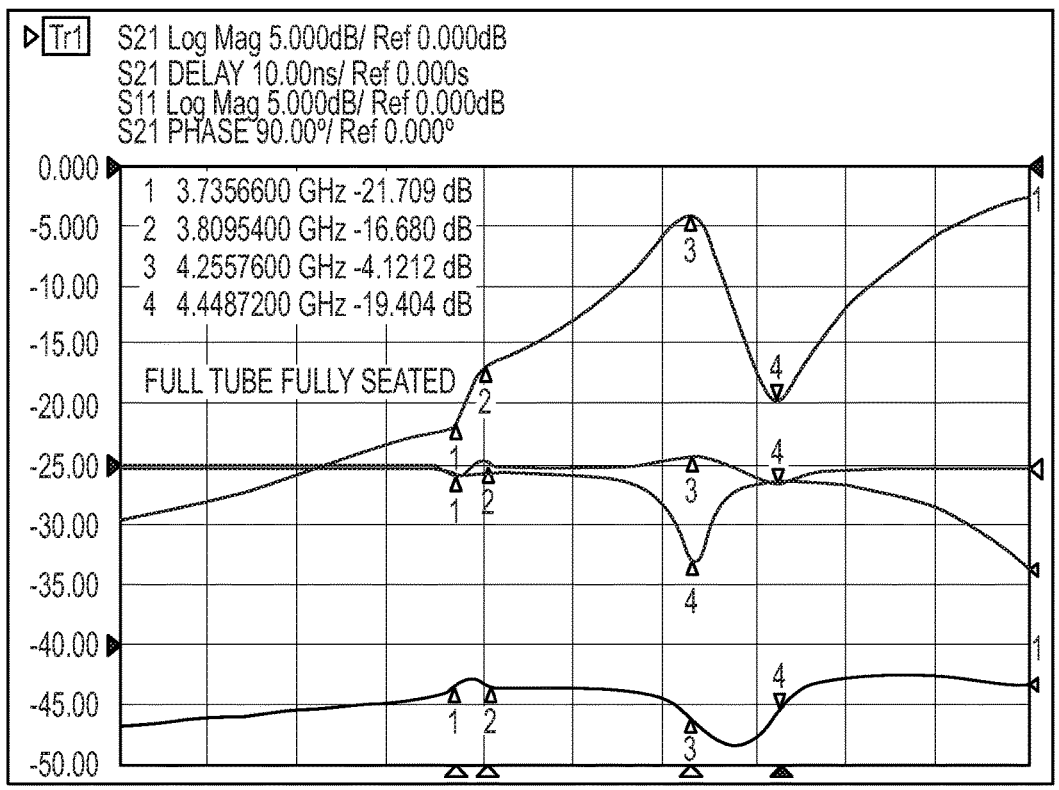
FIG. 63 shows an example graph of energy transmission through an example split ring resonator component when a tube full of fluid was incorrectly seated in the split ring resonator component in accordance with an embodiment of the present disclosure.
Figure 64:
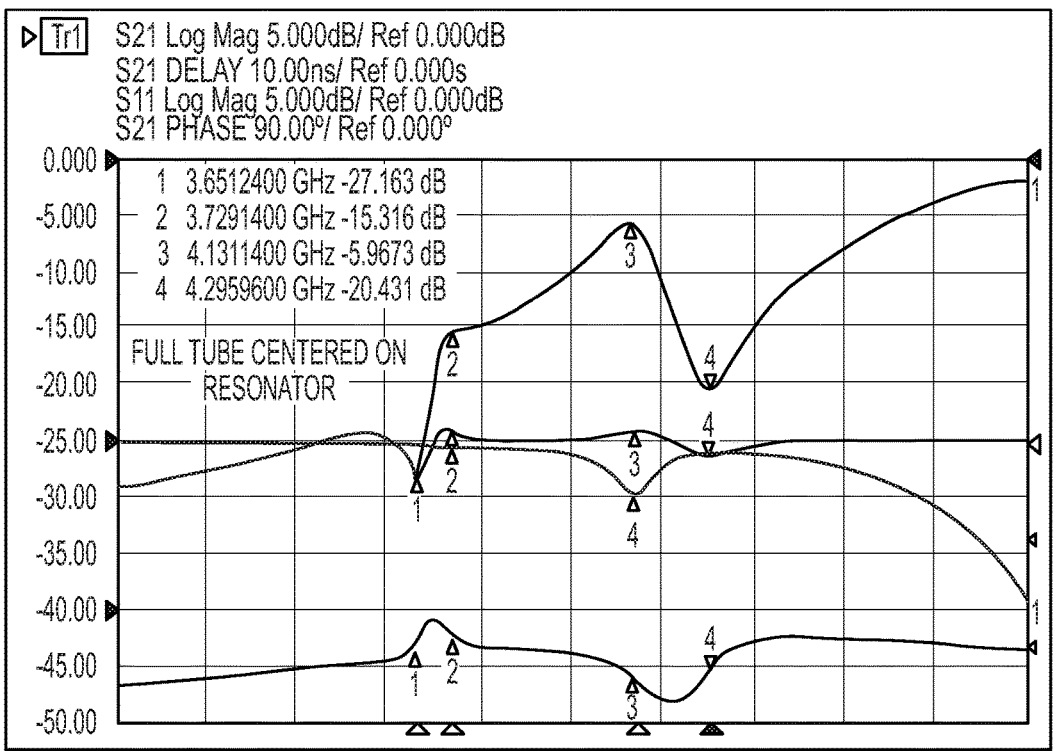
FIG. 64 shows an example graph of energy transmission through an the example split ring resonator component in FIG. 63 when a tube full of fluid was correctly seated in the split ring resonator component in accordance with an embodiment of the present disclosure.

Another two example graphs depicting the transmission of energy through an example split ring resonator component are shown in FIGS. 63-64. The graph in FIG. 63 depicts the transmission of energy when a full tube is incorrectly placed in the split-ring resonator component. The graph in FIG. 64 depicts the transmission of energy when a full tube is correctly seated in a split ring resonator component.

Figure 65:
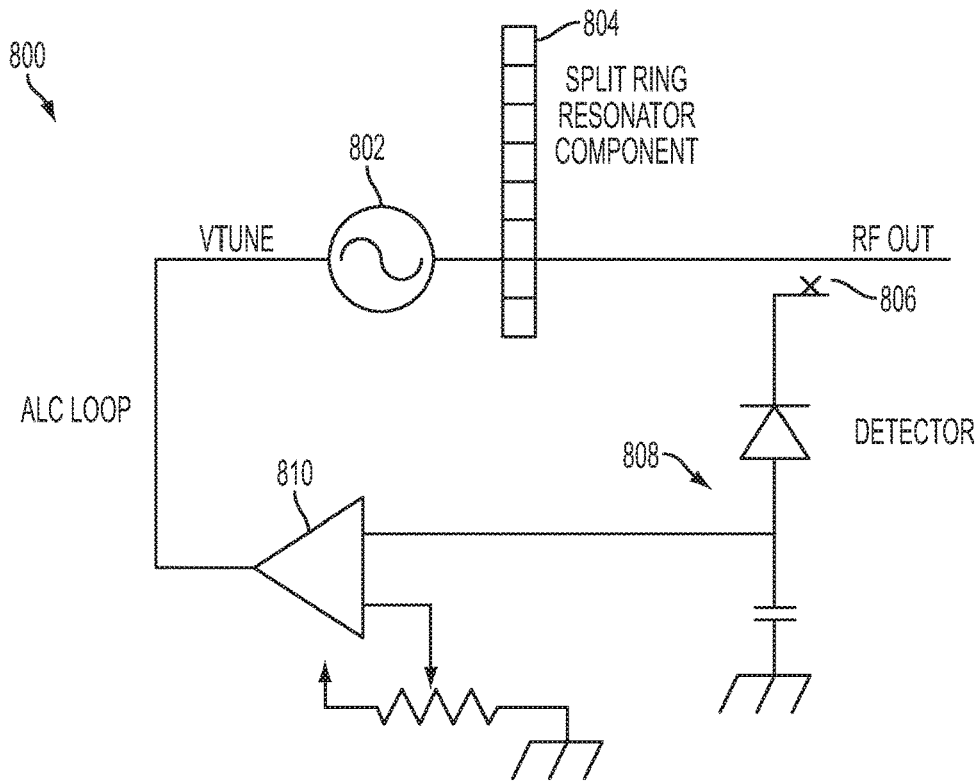
FIG. 65 shows an example of part of circuit which may be used for calibration purposes in a system for detecting a bubble in accordance with an embodiment of the present disclosure.

FIG. 65 shows an example embodiment of a circuit 800 which may be used for calibration purposes in a system for detecting a bubble. The circuit 800 may become active when, for example, a "push to calibrate" button is depressed. As shown, the circuit 800 includes a VCO 802. A voltage is supplied to the VCO 802 via a $V_{TUNE}$ line. This voltage causes the VCO 802 to generate a signal to be transmitted through a split-ring-resonator component 804. The RF OUT signal from the receiving antenna (not shown) of the split-ring resonator component 804 may travel out to additional circuitry or components (not shown) for processing, rectification, storage in memory, etc. In the example embodiment the signal received by the receiving antenna is also looped back to the VCO 804.

The signal travels to a directional coupler 806 from the receiving antenna. The signal is then rectified into a DC voltage by a rectifier 808. After rectification, the DC voltage provides an input voltage to a summing amplifier 810. The summing amplifier 810 is also provided with a reference voltage. The reference voltage may be selected such that it is sufficient to drive the VCO 802. Due to the summing of the input voltage and reference voltage by the summing amplifier 810, the circuit will end up locking to the $V_{TUNE}$ voltage which generates a frequency creating the maximum RF OUT signal. Thus the circuit 800 works as an automatic peak detector and effectively find the resonant frequency of the SRR.

By calibrating the system when a tube known to be full of fluid is in place in the split ring resonator component 804, the frequency which creates the maximum RF OUT signal may be determined. In operation, when the circuit 800 transmits at this frequency it should expect to see this same RF OUT signal if the tube is full of fluid. A processor (not shown) may make use of this information by instructing the VCO 802 to generate this frequency. The processor may monitor the signal received by the receiving antenna of the split-ring resonator 804 to determine if it deviates from the expected RF OUT signal. Deviation beyond, for example, a predefined threshold may indicate the presence of an air bubble. In some alternate embodiments, the circuit 800 may be configured to be calibrated with a tube which is known to be empty.

Figure 66:
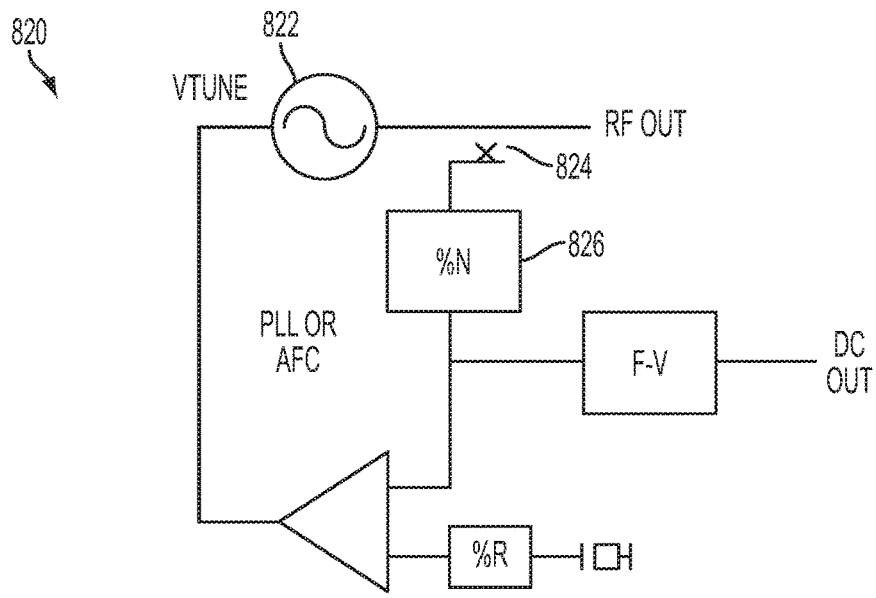
FIG. 66 shows an example of part of a circuit which may be used for calibration purposes in a system for detecting a bubble in accordance with an embodiment of the present disclosure.

FIG. 66 shows example embodiment of a circuit 820 which may be used to create a phase locked loop or automatic frequency control. The circuit 820 shown in FIG. 66 may be used to automatically control for any drift of a VCO 822 due to temperature etc. The circuit 820 shown includes a VCO 822 which produces a signal. The circuit 820 includes a directional coupler 824 to sample a proportion of the signal produced by the VCO 822. This signal then travels to a prescaler 826 which scales the signal down to a lower frequency. A crystal 828 is also included in the circuit 820 to provide a reference frequency which may also be scaled to a lower frequency. The reference and the VCO 822 signal may be compared to produce a VTUNE voltage. This VTUNE voltage is then fed to the VCO 802 thus locking the VCO 802 frequency to the reference frequency.

Figure 67:
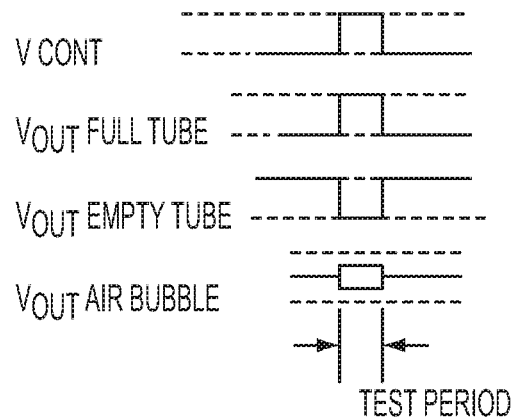
FIG. 67 shows an example graph of a self test which may be performed by a system for detecting a bubble in accordance with an embodiment of the present disclosure.
Figure 68:
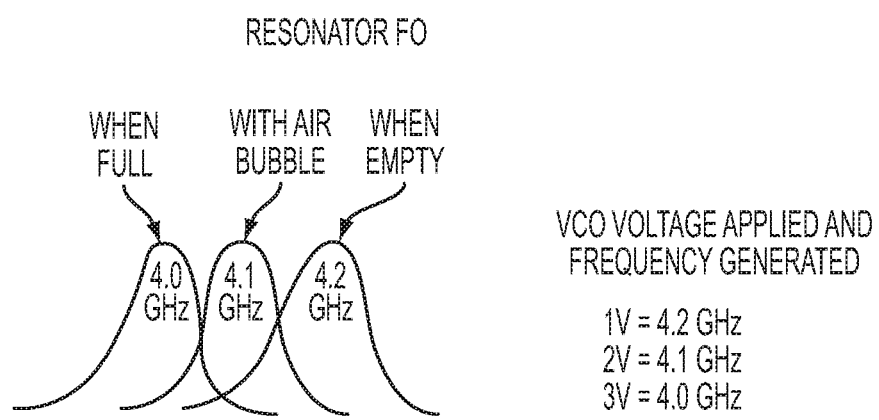
FIG. 68 shows an example graph illustrating the resonant frequencies of a tube which is filled with materials of varying dielectric properties in accordance with an embodiment of the present disclosure.

Referring now both to FIG. 67 and FIG. 68, an example of a self test which may be performed by a system for detecting a bubble is shown. The example self test may be performed by any system described herein. In FIG. 67 four lines which each depict voltage over time are shown. The top line, VCONT, shows the control voltage supplied to a VCO over a period of time. The VOUT Full Tube line shows the output voltage of an air bubble sensor when the tube in the sensor is full of fluid. The VOUT Empty Tube line shows the output voltage of an air bubble sensor when the tube in the sensor is empty. The VOUT Air Bubble line shows the output voltage of an air bubble sensor when the tube in the sensor contains an air bubble.

As shown in FIG. 68, the normal operating voltage supplied to the VCO (when VCONT is low) causes the VCO to generate a signal to be supplied to a split-ring resonator component at the resonant frequency of an SRR which is in proximity to an empty tube. The VCONT low voltage is given as 1 volt for exemplary purposes. As is shown in FIG. 67, when VCONT is low, VOUT Empty Tube is high and VOUT Full Tube is low.

As a check, the VCONT may be periodically intentionally shifted to a LOOK HIGH voltage. The LOOK HIGH voltage may, for example, be chosen to cause the VCO generate a signal at the resonant frequency of an SRR in proximity to a full tube. The LOOK HIGH voltage is shown in FIG. 72 as 3 volts for exemplary purposes. As shown in FIG. 67, when VCONT is high, VOUT Empty Tube should drop low because the SRR is no longer receiving a signal at its resonant frequency. Additionally, when VCONT is high VOUT Full Tube should also be high because the SRR is now receiving a signal at its resonant frequency. If the correct behavior is not observed for a tube thought to be empty or full, the self test may be deemed to have been failed. In such an event, an alarm or alert may be initiated.

Figure 69:
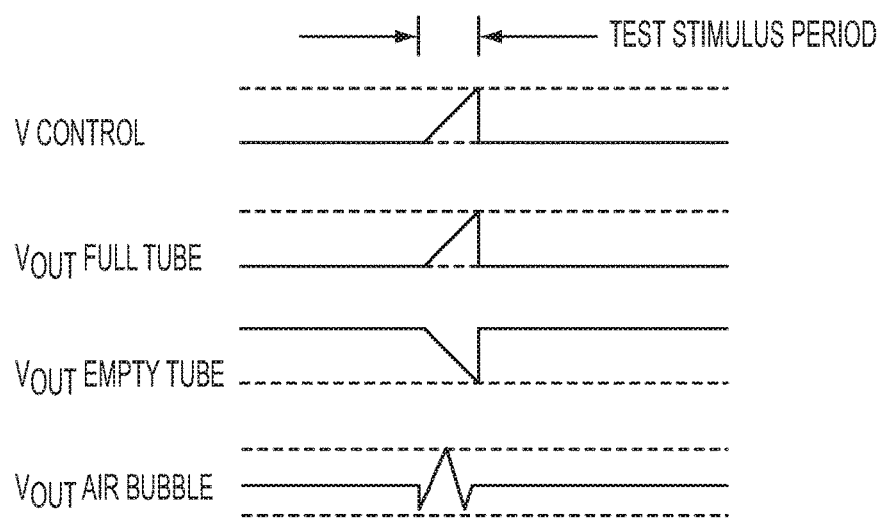
FIG. 69 shows another example graph illustrating a self test which may be performed by a system for detecting a bubble in accordance with an embodiment of the present disclosure.

FIG. 69 shows another example of a self test which may be used to ensure proper function of a system for detecting a bubble. Four lines are shown which depict voltage over time. The first line, VCONTROL, plots the control voltage which is supplied to a VCO to generate a signal. The VOUT Full Tube line plots an example output voltage of an air bubble sensor when the tube in the sensor is full of fluid. The VOUT Empty Tube line shows an example output voltage of an air bubble sensor when the tube in the sensor is empty. The VOUT Air Bubble line shows an example output voltage of an air bubble sensor when the tube in the sensor contains an air bubble.

The self test in FIG. 69 is similar to the self test described in relation to FIG. 67, however, in FIG. 69, the voltage is swept high during the test period. In other embodiments, the voltage may be stepped high. Again, in the example, the normal operating voltage, VCONTROL low, is the voltage which would cause a VCO to generate a signal at the resonant frequency of the SRR with an empty tube present. In alternate embodiments, the normal operating voltage may cause a VCO to generate a signal at the resonant frequency of a full tube. In such embodiments, the voltage may be swept low.

As shown, when VCONTROL is low VOUT Empty Tube is high and VOUT Full Tube is low. As VCONTROL is swept high the VCO's output signal may approach the resonant frequency of the SRR with a full tube in close proximity. This should cause VOUT Empty Tube to drop low and will cause VOUT Full Tube to go high. If correct behavior is not observed for a tube though to be full or empty, the self test may be deemed to have been failed. In such an event, an alarm or alert may be initiated.

When an air bubble is present, the resonant frequency of the SRR will be somewhere between the resonant frequency of the empty tube and the full tube. This should cause the VOUT Air Bubble voltage to rise from rise from low to high and then drop from high to low over a single sweep. If such behavior is observed, an alarm may be triggered.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A system for detecting an at least one condition of interest relating to a tube comprising:
    a split-ring resonator component configured to interface with the tube, wherein the split-ring resonator component comprises:
        a transmitting antenna configured to transmit microwave energy;
        a receiving antenna configured to receive the microwave energy; and
        a split-ring resonator positioned between the transmitting and receiving antennas and positioned adjacent to the tube, wherein the split-ring resonator is adapted to vary at least one parameter of the microwave energy in response to an existence of the at least one condition of interest; and
    a detection component operatively coupled to the split-ring resonator component, the detection component configured to detect the at least one condition of interest.

2. The system according to claim 1, wherein the detection component detects the at least one condition of interest by estimating at least one parameter corresponding to the split-ring resonator.

3. The system according to claim 2, wherein the at least one parameter is selected from the group consisting of a group delay caused by an inner volume of the tube, a propagation delay caused by the inner volume of the tube, a group delay caused by the split-ring resonator, a phase shift caused by the split-ring resonator, a resonance frequency of the split-ring resonator, a phase angle of a test signal applied the split-ring resonator, an amplitude of the test signal applied to the split-ring resonator, a frequency response of the split-ring resonator, a frequency response within a predetermined frequency range of the split-ring resonator, a Q of the split-ring resonator, a bandwidth of the split-ring resonator, a peak of a bandwidth response of the split-ring resonator, an anti-resonance of the split-ring resonator, a phase response of the split-ring resonator, an impedance of the split-ring resonator, a propagation delay of split-ring resonant, an S11 parameter of the split-ring resonator, an S12 parameter of the split-ring resonator, an S21 parameter of the split-ring resonator, and an S22 parameter of the split-ring resonator.

4. The system according to claim 2, wherein the detection component applies a test signal to the split-ring resonator to estimate the at least one parameter.

5. The system according to claim 2, wherein the split-ring resonator includes at least one gap disposed adjacent to the tube, wherein the at least one parameter corresponds to an impedance of the at least one gap.

6. The system according to claim 2, wherein the split-ring resonator includes at least one gap, and the at least one parameter corresponds to dielectric loading of the at least one gap.

7. The system according to claim 2, wherein the detection component detects the at least one condition of interest by detecting a change in the at least one parameter.

8. The system according to claim 1, wherein the split-ring resonator comprises a conductor ring with a gap defined therein.

9. The system according to claim 8, wherein the conductor ring is disposed on a dielectric backing.

10. The system according to claim 1, wherein the split-ring resonator component includes a split ring resonator comprising:
    at least one conductor defining at least one gap, the at least one conductor including one or more capacitive extensions.

11. The system according to claim 1, wherein the split-ring resonator comprises:
    a first conductor defining a first gap; and
    a second conductor disposed adjacent to an inner periphery of the first conductor, the second conductor defining a second gap, wherein said first conductor and said second conductor are concentric and define a common center point.

12. The system according to claim 11, wherein a first center of the first gap is at a radial angle from the common center that is about 180 degrees from a second center of the second gap.

13. The system according to claim 1, wherein at least one of the at least one condition of interest is selected from a group consisting of: the tube is full, the tube is empty, an air bubble exists in the tube, an air bubble of an estimated volume exists in the tube, the tube is not present, the tube is improperly inserted, the tube is properly inserted, the tube is primed, and the tube is unprimed.

14. The system according to claim 1, wherein the transmitting antenna, the receiving antenna, and the split-ring resonator are adapted to encourage a tunneling effect between the transmitting and receiving antennas when the microwave energy is transmitted from the transmitting antenna to the receiving antenna.

15. The system according to claim 1, wherein at least one of the transmitting antenna and the receiving antenna is a loop antenna.

* * * * *